US011535667B2

(12) United States Patent
Olsen et al.

(10) Patent No.: US 11,535,667 B2
(45) Date of Patent: *Dec. 27, 2022

(54) ANTI-CD3 ANTIBODIES AND METHODS OF MAKING AND USING THEREOF

(71) Applicants: SYSTIMMUNE, INC., Redmond, WA (US); SICHUAN BAILI PHARMACEUTICAL CO. LTD., Chengdu (CN)

(72) Inventors: Ole Olsen, Everett, WA (US); Phil Tan, Edmonds, WA (US); Dong Xia, Redmond, WA (US); David Jellyman, Duvall, WA (US); Brian Kovacevich, Snohomish, WA (US); Bill Brady, Bothell, MA (US); Blair Renshaw, Renton, WA (US); Zeren Gao, Redmond, WA (US); Yi Zhu, Chengdu (CN)

(73) Assignees: SYSTIMMUNE, INC., Redmond, WA (US); BAILI-BIO (CHENGDU) PHARMACEUTICAL CO., LTD., Sichuan (CN)

(*) Notice: Subject to any disclaimer, the term of this patent is extended or adjusted under 35 U.S.C. 154(b) by 71 days.

This patent is subject to a terminal disclaimer.

(21) Appl. No.: 16/615,109

(22) PCT Filed: Jun. 22, 2018

(86) PCT No.: PCT/US2018/039143
§ 371 (c)(1),
(2) Date: Nov. 19, 2019

(87) PCT Pub. No.: WO2019/045856
PCT Pub. Date: Mar. 7, 2019

(65) Prior Publication Data
US 2020/0157217 A1    May 21, 2020

Related U.S. Application Data

(60) Provisional application No. 62/551,032, filed on Aug. 28, 2017.

(51) Int. Cl.
| C07K 16/28 | (2006.01) |
| A61K 47/68 | (2017.01) |
| C12N 15/85 | (2006.01) |
| A61K 9/08 | (2006.01) |
| A61K 45/06 | (2006.01) |

(52) U.S. Cl.
CPC ...... *C07K 16/2809* (2013.01); *A61K 47/6801* (2017.08); *C12N 15/85* (2013.01); *A61K 9/08* (2013.01); *A61K 45/06* (2013.01); *C07K 2317/24* (2013.01); *C07K 2317/33* (2013.01); *C07K 2317/76* (2013.01); *C12N 2015/8518* (2013.01)

(58) Field of Classification Search
None
See application file for complete search history.

(56) References Cited

U.S. PATENT DOCUMENTS 5,859,205 A * 1/1999 Adair ............... C07K 16/465
530/387.3
7,728,114 B2 * 6/2010 Mach ................. A61P 5/16
530/388.22

OTHER PUBLICATIONS

Harlow et al. (Antibodies, A Laboratory Manual, Cold Spring Harbor laboratory, 1988, pp. 37-47). (Year: 1988).*
Edwards et al. (J. Mol. Biol. (2003) 334, 103-118). (Year: 2003).*
Lloyd et al., Protein Engineering, Design & Selection vol. 22 No. 3 pp. 159-168, 2009. (Year: 2009).*
Vajdos et al. (J Mol Biol. Jul. 5, 2002;320(2):415-28). (Year: 2002).*
Bedouelle et al. (FEBS J. Jan. 2006;273(1):34-46). (Year: 2006).*
Brown et al. (J Immunol. May 1, 1996;156(9):3285-91). (Year: 1996).*
Colman (Research in Immunology, 145:33-36, 1994). (Year: 1994).*
Rudikoff et al. (Proc. Natl. Acad. Sci. USA, 79: 1979-1983, Mar. 1982). (Year: 1982).*
Reuschenbach et al., Cancer immunology, immunotherapy: CII, 58(10), 1535-1544 (2009). (Year: 2009).*
Ukena et al. (Experimental Hematology 2011;39:1152-1160). (Year: 2011).*
Shou et al., BMC Cancer (2016) 16:687. (Year: 2016).*
Curiel et al., Nature medicine, 10(9), 942-949 (2004). (Year: 2004).*
Eduardo Padlan, Mol Immunol. Feb. 1994;31(3):169-217. (Year: 1994).*
Portolano et al., J Immunol. Feb. 1, 1993;150(3):880-7. (Year: 1993).*

* cited by examiner

*Primary Examiner* — Zachary S Skelding
(74) *Attorney, Agent, or Firm* — Zhihua Han

(57) ABSTRACT

The applications provides the anti-CD3 monoclonal antibodies, antigen-binding portions thereof, therapeutic compositions thereof and/or nucleic acid encoding the same, and their use to active CD3+ T-cells to enhance cell-mediated immune responses in the treatment of cancer and other T-cell dysfunctional disorders.

17 Claims, 15 Drawing Sheets

Specification includes a Sequence Listing.

| Day | Cohort | Antigen | Adjuvant |
|---|---|---|---|
| 0 | 1 | Human CD3 Delta-Epsilon Fc (KnH) and Gamma-Epsilon Fc (KnH) | Freund's |
| 7 | 1 | Human CD3 TcR transfected cells | Alyhrodgel 2% + CpG 2007 |
| 14 | 1 | Cynomolgous CD3 Delta-Epsilon Fc and (KnH) Gamma-Epsilon Fc (KnH) | Incomplete Fruend's |
| 21 | 1 | Cynomolgous CD3 TcR transfected cells | Alyhrodgel 2% + CpG 2007 |
| 28 | 1 | Human CD3 Delta-Epsilon Fc (KnH) and Gamma-Epsilon Fc (KnH) | Incomplete Fruend's |
| 35 | 1 | Human CD3 TcR transfected cells | Alyhrodgel 2% + CpG 2007 |
| 42 | 1 | Human CD3 TcR transfected cells | Alyhrodgel 2% + CpG 2007 |
| 51 | 1 | Cynomolgous CD3 TcR transfected cells | Alyhrodgel 2% + CpG 2007 |
| 55 | | Harvest | NA |

FIGURE 1A

| Day | Cohort | Antigen | Adjuvant |
|---|---|---|---|
| 0 | 2 | Human CD3 TcR transfected cells | Titermax |
| 7 | 2 | Cynomolgous CD3 TcR transfected cells | Alyhrodgel 2% + CpG 2007 |
| 14 | 2 | Human CD3 TcR transfected cells | Titermax |
| 21 | 2 | Cynomolgous CD3 TcR transfected cells | Alyhrodgel 2% + CpG 2007 |
| 28 | 2 | Human CD3 TcR transfected cells | Titermax |
| 37 | 2 | Cynomolgous CD3 TcR transfected cells | Alyhrodgel 2% + CpG 2007 |
| 47 | 2 | Human CD3 TcR transfected cells | Titermax |
| 54 | 2 | Cynomolgous CD3 TcR transfected cells | Alyhrodgel 2% + CpG 2007 |
| 61 | 2 | Cynomolgous CD3 TcR transfected cells | Titermax |
| 68 | 2 | Cynomolgous CD3 TcR transfected cells | Alyhrodgel 2% + CpG 2007 |
| 72 | 2 | Harvest | NA |

FIGURE 1B

FIGURE 2 shows the analysis of rabbit serum analyzed by ELISA human or cynomolgus CD3 gamma-epsilon or delta-epsilon Fc-specific IgG before and after immunization. 2A: Analysis of rabbit serum analyzed by ELISA for human CD3 delta-epsilon Fc specific IgG before and after immunization; 2B: Analysis of rabbit serum analyzed by ELISA for human gamma-epsilon Fc-specific IgG before and after immunization; 2C: Analysis of rabbit serum analyzed by ELISA for cynomolgus CD3 delta-epsilon Fc-specific IgG before and after immunization; and 2D: Analysis of rabbit serum analyzed by ELISA for cynomolgus CD3 gamma-epsilon Fc-specific IgG before and after immunization.

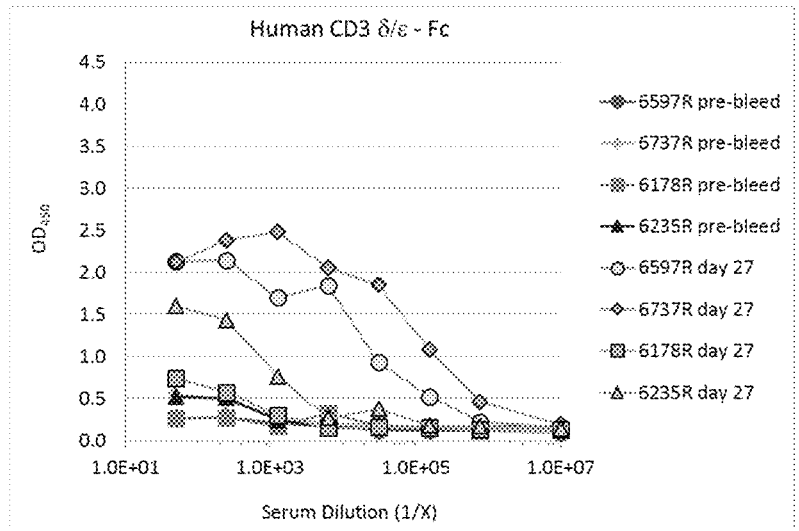

FIGURE 2A

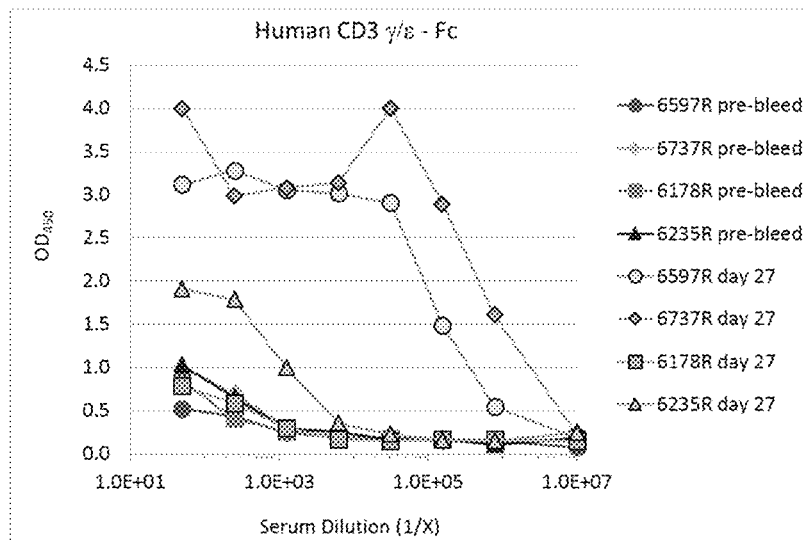

FIGURE 2B

FIGURE 3 provides a summary of screening BCC supernatants for rabbit IgG binding human and cynomolgus T cells by FACS and activation of human CD3+ T cells

| | | Antibody in B cell culture well | | | |
|---|---|---|---|---|---|
| | BCC well ID | T activate IL-2 (OD) | Parental HEK 293's (MFI) | Cyno T cell line (MFI) | Human CD3+ T cells (MFI) |
| 1 | 284A10 | 4.0 | 15 | 615 | 413 |
| 2 | 284C10 | 4.0 | 16 | 432 | 402 |
| 3 | 293G4 | 4.0 | 22 | 219 | 359 |
| 4 | 299C5 | 3.5 | 15 | 565 | 527 |
| 5 | 282A6 | 3.5 | 25 | 266 | 454 |
| 6 | 299F6 | 3.4 | 18 | 1109 | 847 |
| 7 | 281E8 | 3.1 | 18 | 183 | 299 |
| 8 | 295E9 | 3.1 | 17 | 549 | 478 |
| 9 | 313H9 | 2.9 | 35 | 254 | 307 |
| 10 | 295A8 | 2.9 | 16 | 431 | 540 |
| 11 | 290G5 | 2.8 | 23 | 192 | 255 |
| 12 | 292D3 | 2.7 | 35 | 290 | 285 |
| 13 | 286E5 | 2.3 | 24 | 33 | 25 |
| 14 | 289A4 | 2.1 | 17 | 43 | 70 |
| 15 | 290A12 | 1.9 | 4 | 158 | 75 |
| 16 | 302G8 | 1.8 | 22 | 277 | 184 |
| 17 | 298E4 | 1.7 | 16 | 264 | 215 |
| 18 | 299E6 | 1.7 | 30 | 114 | 170 |
| 19 | 291H9 | 1.7 | 14 | 528 | 910 |
| 20 | 284C9 | 0.9 | 34 | 20 | 18 |
| 21 | 283E3 | 0.8 | 20 | 273 | 527 |
| 22 | 284B1 | 0.6 | 28 | 527 | 456 |
| 23 | 284A9 | 0.6 | 19 | 25 | 27 |

FIGURE 4 shows the binding of example chimeric rabbit/human IgG antibodies to Cynomolgus CD3 Delta, Gamma, or Epsilon Fc fusion proteins and human T cell line Jurkat (nd = not done)

|   | BCC well ID | Antibody in B cell culture well ||||  Chimeric Antibody |||
|---|---|---|---|---|---|---|---|---|
|   |   | T activate IL-2 (OD) | Parental HEK 293's (MFI) | Cyno T cell line (MFI) | Human CD3+ T cells (MFI) | Off-rate Cynomolgus δ/ε - Fc | Off-rate Cynomolgus γ/ε - Fc | FACS binding Human CD3+ T cell line Jurkat |
| 1 | 284A10 | 4.0 | 15 | 615 | 413 | 3.2E-03 | 1.3E-03 | +++++ |
| 2 | 284C10 | 4.0 | 16 | 432 | 402 | - | - | nd |
| 3 | 293G4 | 4.0 | 22 | 219 | 359 | - | - | nd |
| 4 | 299C5 | 3.5 | 15 | 565 | 527 | - | - | nd |
| 5 | 282A6 | 3.5 | 25 | 266 | 454 | - | - | nd |
| 6 | 299F6 | 3.4 | 18 | 1109 | 847 | 5.2E-04 | 4.6E-04 | +++++ |
| 7 | 281E8 | 3.1 | 18 | 183 | 299 | - | - | nd |
| 8 | 295E9 | 3.1 | 17 | 549 | 478 | 5.2E-03 | 5.2E-03 | +++++ |
| 9 | 313H9 | 2.9 | 35 | 254 | 307 | - | - | nd |
| 10 | 295A8 | 2.9 | 16 | 431 | 540 | - | - | nd |
| 11 | 290G5 | 2.8 | 23 | 192 | 255 | - | - | nd |
| 12 | 292D3 | 2.7 | 35 | 290 | 285 | - | - | nd |
| 13 | 286E5 | 2.3 | 24 | 33 | 25 | - | - | nd |
| 14 | 289A4 | 2.1 | 17 | 43 | 70 | - | - | nd |
| 15 | 290A12 | 1.9 | 4 | 158 | 75 | - | - | nd |
| 16 | 302G8 | 1.8 | 22 | 277 | 184 | - | - | nd |
| 17 | 298E4 | 1.7 | 16 | 264 | 215 | - | - | nd |
| 18 | 299E6 | 1.7 | 30 | 114 | 170 | - | - | nd |
| 19 | 291H9 | 1.7 | 14 | 528 | 910 | 1.8E-02 | 1.8E-02 | - |
| 20 | 284C9 | 0.9 | 34 | 20 | 18 | nd | nd | nd |
| 21 | 283E3 | 0.8 | 20 | 273 | 527 | 3.5E-03 | 3.9E-03 | +++++ |
| 22 | 284B1 | 0.6 | 28 | 527 | 456 | - | - | nd |
| 23 | 284A9 | 0.6 | 19 | 25 | 27 | 3.3E-03 | - | - |

FIGURE 5 shows the FACS analysis of example chimeric rabbit/human CD3-specific antibodies binding to the human T cell line Jurkat. 5A: FACS analysis of example chimeric rabbit/human CD3-specific antibody 283E3 binding to the human T cell line Jurkat; 5B FACS analysis of example chimeric rabbit/human CD3-specific antibody 284A10 binding to the human T cell line Jurkat; 5C: FACS analysis of example chimeric rabbit/human CD3-specific antibody 284A9 binding to the human T cell line Jurkat; 5D: FACS analysis of example chimeric rabbit/human CD3-specific antibody 299F6 binding to the human T cell line Jurkat; 5E: FACS analysis of example chimeric rabbit/human CD3-specific antibody 295E9 binding to the human T cell line Jurkat; and 5F: FACS analysis of example chimeric rabbit/human CD3-specific antibody 291H9 binding to the human T cell line Jurkat.

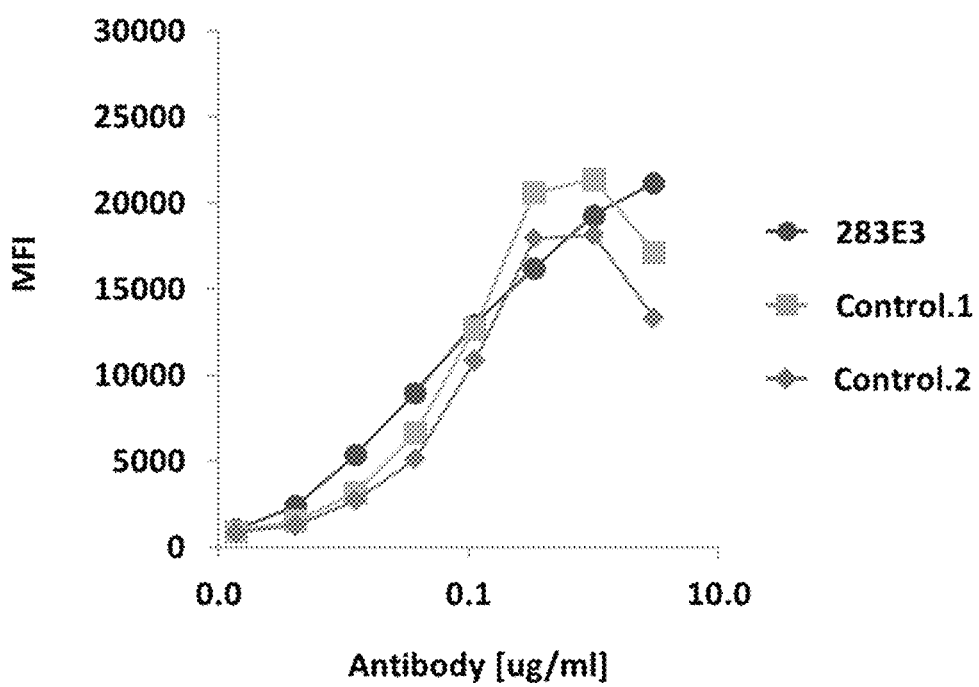

FIGURE 5A

FIGURE 6 shows the FACS analysis of example chimeric rabbit/human CD3-specific antibodies binding to the human T cell line Jurkat. 6A: FACS analysis of example chimeric rabbit/human CD3-specific antibody 496C5 binding to the human T cell line Jurkat; 6B: FACS analysis of example chimeric rabbit/human CD3-specific antibody 480C8 binding to the human T cell line Jurkat; 6C: FACS analysis of example chimeric rabbit/human CD3-specific antibody 480A7 binding to the human T cell line Jurkat; 6D: FACS analysis of example chimeric rabbit/human CD3-specific antibody 485G11 binding to the human T cell line Jurkat; and 6E: FACS analysis of example chimeric rabbit/human CD3-specific antibody 485H6 binding to the human T cell line Jurkat.

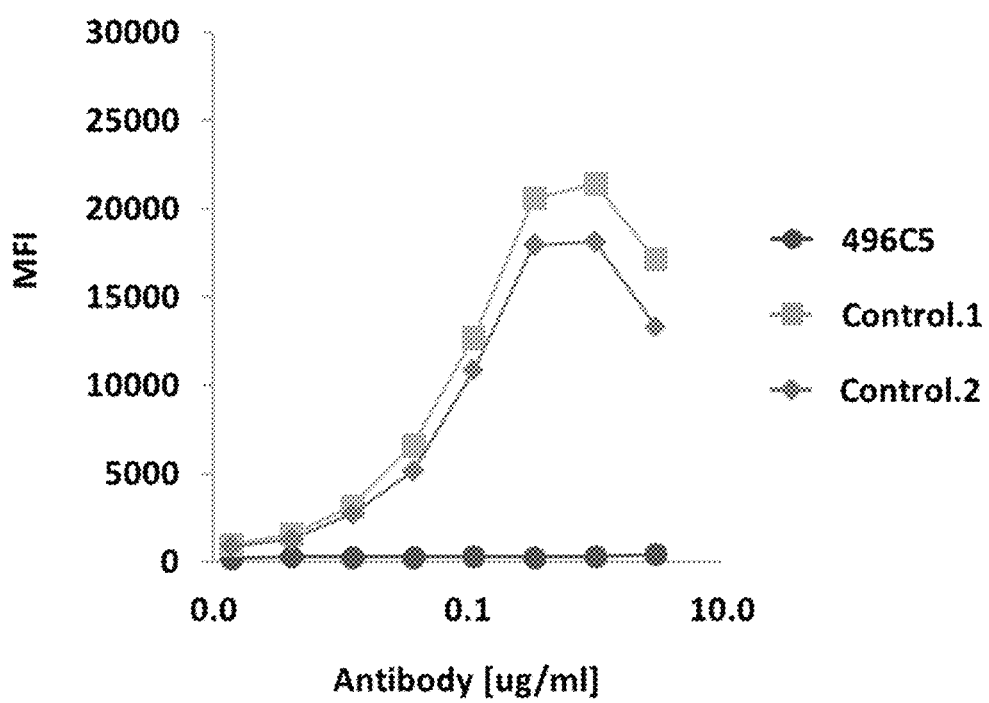

FIGURE 6A

FIGURE 7 shows the activation of human CD3+ T cells by example chimeric rabbit/human CD3-specific antibodies
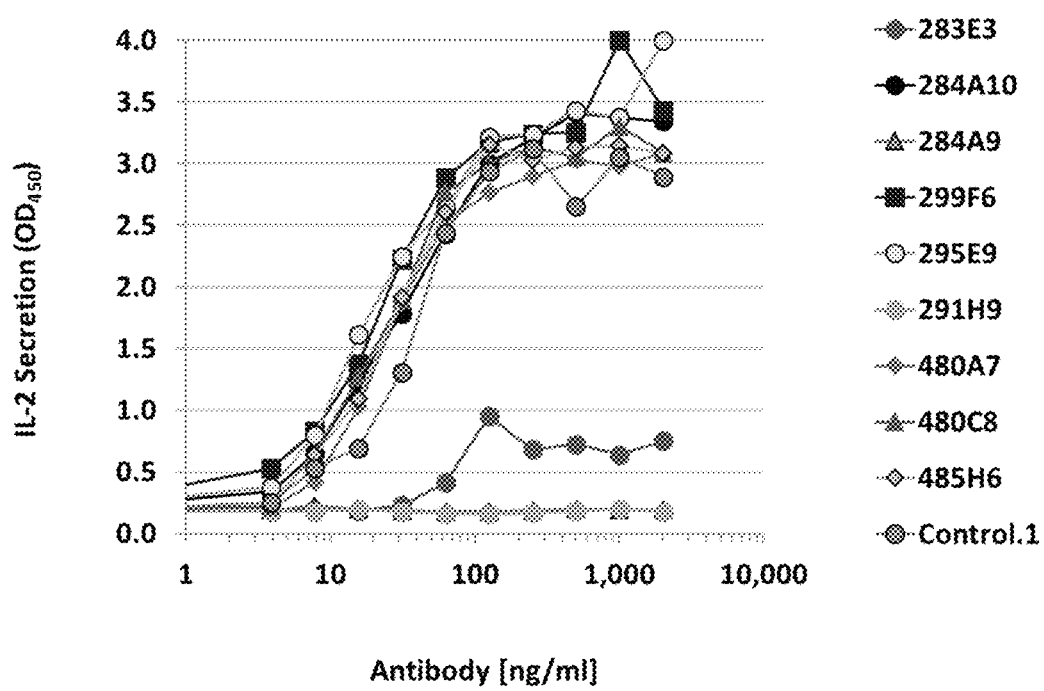

FIGURE 8 shows the binding and off-rate analysis of example chimeric rabbit/human or humanized CD3-specific antibodies

| mAb | Format | Antigen | Bivalent kdis (1/s) |
|---|---|---|---|
| 284A10 | chimeric | Human δ/ε - Fc | 5.0E-04 |
| 284A10 | chimeric | Human δ/γ - Fc | 1.3E-03 |
| 284A10 1.1 | humanized | Human δ/ε - Fc | 5.3E-04 |
| 299F6 | chimeric | Human δ/ε - Fc | 4.9E-04 |
| 299F6 | chimeric | Human δ/γ - Fc | 4.5E-04 |
| 299F6 1.1 | humanized | Human δ/ε - Fc | 6.0E-04 |
| 480C8 | chimeric | Human δ/ε - Fc | 4.2E-04 |
| 480C8 | chimeric | Human δ/γ - Fc | 5.4E-04 |
| 480C8 1.1 | humanized | Human δ/ε - Fc | 5.0E-04 |
| 295E9 | chimeric | Human δ/ε - Fc | 5.2E-03 |
| 295E9 | chimeric | Human δ/γ - Fc | 5.2E-03 |
| 480A7 | chimeric | Human δ/ε - Fc | 6.6E-04 |
| 480A7 | chimeric | Epsilon-Gamma | 6.0E-04 |
| 485H6 | chimeric | Human δ/ε - Fc | 5.7E-04 |
| 485H6 | chimeric | Human δ/γ - Fc | 5.3E-04 |

SEQUENCE LISTING

<160> NUMBER OF SEQ ID NOS: 78

<210> SEQ ID NO 1
<211> LENGTH: 657
<212> TYPE: DNA
<213> ORGANISM: Artificial Sequence
<220> FEATURE:
<223> OTHER INFORMATION: Synthesized

<400> SEQUENCE: 1

```
gatgtcgtga tgacccagac tcctccctcc gtgtctgcag ctgtgggagg cacagtcacc    60
atcaagtgcc aggccagtga gagcattagc agttggttag cctggtatca gcagaaacca   120
gggcagcctc ccaagctcct gatctacgaa gcatccaaac tggcatctgg ggtcccatcg   180
cggttcagtg gcagtggatc tgggacagag ttcactctca ccatcagtga cctggagtgt   240
gccgatgctg ccacttacta ctgtcaaggc tatttttatt ttattagtcg tacttatgta   300
aattctttcg gcggaggcac cgaggtggag ttcaaacgta cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgt     657
```

<210> SEQ ID NO 2
<211> LENGTH: 336
<212> TYPE: DNA
<213> ORGANISM: Artificial Sequence
<220> FEATURE:
<223> OTHER INFORMATION: Synthesized

<400> SEQUENCE: 2

```
gatgtcgtga tgacccagac tcctccctcc gtgtctgcag ctgtgggagg cacagtcacc    60
atcaagtgcc aggccagtga gagcattagc agttggttag cctggtatca gcagaaacca   120
gggcagcctc ccaagctcct gatctacgaa gcatccaaac tggcatctgg ggtcccatcg   180
cggttcagtg gcagtggatc tgggacagag ttcactctca ccatcagtga cctggagtgt   240
gccgatgctg ccacttacta ctgtcaaggc tatttttatt ttattagtcg tacttatgta   300
aattctttcg gcggaggcac cgaggtggag ttcaaa                              336
```

<210> SEQ ID NO 3
<211> LENGTH: 219
<212> TYPE: PRT
<213> ORGANISM: Artificial Sequence
<220> FEATURE:
<223> OTHER INFORMATION: Synthesized

<400> SEQUENCE: 3

Asp Val Val Met Thr Gln Thr Pro Ser Val Ser Ala Ala Val Gly
1               5                   10                  15

Gly Thr Val Thr Ile Lys Cys Gln Ala Ser Glu Ser Ile Ser Ser Trp
                20                  25                  30

Leu Ala Trp Tyr Gln Gln Lys Pro Gly Gln Pro Pro Lys Leu Leu Ile
            35                  40                  45

Tyr Glu Ala Ser Lys Leu Ala Ser Gly Val Pro Ser Arg Phe Ser Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Gly Tyr Phe Tyr Phe Ile Ser
                85                  90                  95

Arg Thr Tyr Val Asn Ser Phe Gly Gly Gly Thr Glu Val Glu Phe Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
                210                 215

<210> SEQ ID NO 4
<211> LENGTH: 112
<212> TYPE: PRT
<213> ORGANISM: Artificial Sequence
<220> FEATURE:
<223> OTHER INFORMATION: Synthesized

<400> SEQUENCE: 4

Asp Val Val Met Thr Gln Thr Pro Ser Val Ser Ala Ala Val Gly
1               5                   10                  15

Gly Thr Val Thr Ile Lys Cys Gln Ala Ser Glu Ser Ile Ser Ser Trp
                20                  25                  30

Leu Ala Trp Tyr Gln Gln Lys Pro Gly Gln Pro Pro Lys Leu Leu Ile
            35                  40                  45

Tyr Glu Ala Ser Lys Leu Ala Ser Gly Val Pro Ser Arg Phe Ser Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Gly Tyr Phe Tyr Phe Ile Ser
                85                  90                  95

Arg Thr Tyr Val Asn Ser Phe Gly Gly Gly Thr Glu Val Glu Phe Lys
                100                 105                 110

<210> SEQ ID NO 5
<211> LENGTH: 1341

<212> TYPE: DNA
<213> ORGANISM: Artificial Sequence
<220> FEATURE:
<223> OTHER INFORMATION: Synthesized

<400> SEQUENCE: 5

```
cagtcgctgg aggagtccgg gggtcgcctg gtcacgcctg ggacgcccct gacactcacc        60
tgcacagtct ctggattcac catcagtacc aatgcaatga gctgggtccg ccaggttcca       120
gggaaggggc tggagtggat cggagtcatt actggtcgtg atatcacata ctacgcgagc       180
tgggcgaaag gccgattcac catctccaaa acctcgtcga ccacggtgga tctgaaaatg       240
accagtctga cagccgagga ctcggccacc tatttctgtg ccagagacgg tggttcttct       300
gctattacta gtaacaacat ttggggccca ggcaccctcg tcaccgtctc gagcgctagc       360
accaagggcc catcggtctt ccccctggca ccctcctcca agagcacctc tgggggcaca       420
gcggccctgg gctgcctggt caaggactac ttccccgaac cggtgacggt gtcgtggaac       480
tcaggcgccc tgaccagcgg cgtgcacacc ttcccggctg tcctacagtc ctcaggactc       540
tactccctca gcagcgtggt gaccgtgccc tccagcagct gggcaccca gacctacatc        600
tgcaacgtga atcacaagcc cagcaacacc aaggtggaca gagagttga gcccaaatct        660
tgtgacaaaa ctcacacatg cccaccgtgc ccagcacctg aagccgcggg ggcaccgtca       720
gtcttcctct tccccccaaa acccaaggac accctcatga tctcccggac ccctgaggtc       780
acatgcgtgg tggtggacgt gagccacgaa gaccctgagg tcaagttcaa ctggtacgtg       840
gacggcgtgg aggtgcataa tgccaagaca aagccgcggg aggagcagta caacagcacg       900
taccgtgtgg tcagcgtcct caccgtcctg caccaggact ggctgaatgg caaggagtac       960
aagtgcgcgg tctccaacaa agccctccca gcccccatcg agaaaaccat ctccaaagcc      1020
aaagggcagc cccgagaacc acaggtgtac accctgcccc catcccggga tgagctgacc      1080
aagaaccagg tcagcctgac ctgcctggtc aaaggcttct atcccagcga catcgccgtg      1140
gagtgggaga gcaatgggca gccggagaac aactacaaga ccacgcctcc cgtgctggac      1200
tccgacggct ccttcttcct ctatagcaag ctcaccgtgg acaagagcag gtggcagcag      1260
gggaacgtct tctcatgctc cgtgatgcat gaggctctgc acaaccacta cacgcagaag      1320
agcctctccc tgtctccggg t                                                1341
```

<210> SEQ ID NO 6
<211> LENGTH: 354
<212> TYPE: DNA
<213> ORGANISM: Artificial Sequence
<220> FEATURE:
<223> OTHER INFORMATION: Synthesized

<400> SEQUENCE: 6

```
cagtcgctgg aggagtccgg gggtcgcctg gtcacgcctg ggacgcccct gacactcacc        60
tgcacagtct ctggattcac catcagtacc aatgcaatga gctgggtccg ccaggttcca       120
gggaaggggc tggagtggat cggagtcatt actggtcgtg atatcacata ctacgcgagc       180
tgggcgaaag gccgattcac catctccaaa acctcgtcga ccacggtgga tctgaaaatg       240
accagtctga cagccgagga ctcggccacc tatttctgtg ccagagacgg tggttcttct       300
gctattacta gtaacaacat ttggggccca ggcaccctcg tcaccgtctc gagc            354
```

<210> SEQ ID NO 7
<211> LENGTH: 447
<212> TYPE: PRT

<213> ORGANISM: Artificial Sequence
<220> FEATURE:
<223> OTHER INFORMATION: Synthesized

<400> SEQUENCE: 7

```
Gln Ser Leu Glu Glu Ser Gly Gly Arg Leu Val Thr Pro Gly Thr Pro
1               5                   10                  15

Leu Thr Leu Thr Cys Thr Val Ser Gly Phe Thr Ile Ser Thr Asn Ala
            20                  25                  30

Met Ser Trp Val Arg Gln Val Pro Gly Lys Gly Leu Glu Trp Ile Gly
        35                  40                  45

Val Ile Thr Gly Arg Asp Ile Thr Tyr Tyr Ala Ser Trp Ala Lys Gly
    50                  55                  60

Arg Phe Thr Ile Ser Lys Thr Ser Ser Thr Val Asp Leu Lys Met
65                  70                  75                  80

Thr Ser Leu Thr Ala Glu Asp Ser Ala Thr Tyr Phe Cys Ala Arg Asp
                85                  90                  95

Gly Gly Ser Ser Ala Ile Thr Ser Asn Asn Ile Trp Gly Pro Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Ala Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380
```

```
Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly
    435                 440                 445
```

<210> SEQ ID NO 8
<211> LENGTH: 118
<212> TYPE: PRT
<213> ORGANISM: Artificial Sequence
<220> FEATURE:
<223> OTHER INFORMATION: synthesized

<400> SEQUENCE: 8

```
Gln Ser Leu Glu Glu Ser Gly Gly Arg Leu Val Thr Pro Gly Thr Pro
1               5                   10                  15

Leu Thr Leu Thr Cys Thr Val Ser Gly Phe Thr Ile Ser Thr Asn Ala
            20                  25                  30

Met Ser Trp Val Arg Gln Val Pro Gly Lys Gly Leu Glu Trp Ile Gly
        35                  40                  45

Val Ile Thr Gly Arg Asp Ile Thr Tyr Tyr Ala Ser Trp Ala Lys Gly
    50                  55                  60

Arg Phe Thr Ile Ser Lys Thr Ser Ser Thr Thr Val Asp Leu Lys Met
65                  70                  75                  80

Thr Ser Leu Thr Ala Glu Asp Ser Ala Thr Tyr Phe Cys Ala Arg Asp
                85                  90                  95

Gly Gly Ser Ser Ala Ile Thr Ser Asn Asn Ile Trp Gly Pro Gly Thr
            100                 105                 110

Leu Val Thr Val Ser Ser
        115
```

<210> SEQ ID NO 9
<211> LENGTH: 657
<212> TYPE: DNA
<213> ORGANISM: Artificial Sequence
<220> FEATURE:
<223> OTHER INFORMATION: synthesized

<400> SEQUENCE: 9

```
gatgtcgtga tgacccagac tccatcctcc gtgtctgcag ctgtgggagg cacagtcacc      60
atcaattgcc aagccagtga gagcattagc agttggttag cctggtatca gcagaaacca     120
gggcagcctc ccaagctcct gatctacgaa gcatccaaac tggcatctgg ggtcccatcg     180
cggttcagtg gcagtggatc tgggacagag ttcactctca ccatcagcgg cgtgcagtgt     240
gacgatgctg ccacttacta ctgtcaaggc tattttttatt ttattagtcg tagttatgtg     300
aatgctttcg gcggagggac cgaggtgggg gtcaaacgta cggtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgt      657
```

<210> SEQ ID NO 10
<211> LENGTH: 336
<212> TYPE: DNA
<213> ORGANISM: Artificial Sequence
<220> FEATURE:
<223> OTHER INFORMATION: synthesized

<400> SEQUENCE: 10

```
gatgtcgtga tgacccagac tccatcctcc gtgtctgcag ctgtgggagg cacagtcacc    60
atcaattgcc aagccagtga gagcattagc agttggttag cctggtatca gcagaaacca   120
gggcagcctc ccaagctcct gatctacgaa gcatccaaac tggcatctgg ggtcccatcg   180
cggttcagtg gcagtggatc tgggacagag ttcactctca ccatcagcgg cgtgcagtgt   240
gacgatgctg ccacttacta ctgtcaaggc tatttttatt ttattagtcg tagttatgtg   300
aatgctttcg gcggagggac cgaggtgggg gtcaaa                             336
```

<210> SEQ ID NO 11
<211> LENGTH: 219
<212> TYPE: PRT
<213> ORGANISM: Artificial Sequence
<220> FEATURE:
<223> OTHER INFORMATION: synthesized

<400> SEQUENCE: 11

```
Asp Val Val Met Thr Gln Thr Pro Ser Ser Val Ser Ala Ala Val Gly
1               5                   10                  15

Gly Thr Val Thr Ile Asn Cys Gln Ala Ser Glu Ser Ile Ser Ser Trp
            20                  25                  30

Leu Ala Trp Tyr Gln Gln Lys Pro Gly Gln Pro Pro Lys Leu Leu Ile
        35                  40                  45

Tyr Glu Ala Ser Lys Leu Ala Ser Gly Val Pro Ser Arg Phe Ser Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Gly Tyr Phe Tyr Phe Ile Ser
                85                  90                  95

Arg Ser Tyr Val Asn Ala Phe Gly Gly Gly Thr Glu Val Val Phe Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 12
<211> LENGTH: 112
<212> TYPE: PRT
<213> ORGANISM: Artificial Sequence
<220> FEATURE:
<223> OTHER INFORMATION: synthesized

<400> SEQUENCE: 12

```
Asp Val Val Met Thr Gln Thr Pro Ser Ser Val Ser Ala Ala Val Gly
1               5                   10                  15

Gly Thr Val Thr Ile Asn Cys Gln Ala Ser Glu Ser Ile Ser Ser Trp
            20                  25                  30

Leu Ala Trp Tyr Gln Gln Lys Pro Gly Gln Pro Pro Lys Leu Leu Ile
        35                  40                  45

Tyr Glu Ala Ser Lys Leu Ala Ser Gly Val Pro Ser Arg Phe Ser Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Gly Tyr Phe Tyr Phe Ile Ser
                85                  90                  95

Arg Ser Tyr Val Asn Ala Phe Gly Gly Gly Thr Glu Val Val Phe Lys
            100                 105                 110
```

<210> SEQ ID NO 13
<211> LENGTH: 1341
<212> TYPE: DNA
<213> ORGANISM: Artificial Sequence
<220> FEATURE:
<223> OTHER INFORMATION: synthesized

<400> SEQUENCE: 13

| | |
|---|---|
| cagtcgctgg aggagtccgg gggtcgcctg gtcacgcctg ggacgcccct gacactcacc | 60 |
| tgcacagtct ctggattcac catcagtagc aatgcaatga gctgggtccg ccaggctcca | 120 |
| gggaagggc tggagtggat cggagtcatt actggtcgtg atatcacata ctacgcgaac | 180 |
| tgggcgaaag gccgattcac catctccaaa acctcgtcga ccacggtgga tctgaaaatg | 240 |
| accagtctga cagccgagga ctcggccacc tatttctgtg ccagagacgg tggttcttct | 300 |
| gctattacta gtaacaacat tgggggccca gggaccctgg tcaccgtctc gagcgctagc | 360 |
| accaagggcc catcggtctt ccccctggca ccctcctcca agagcacctc tgggggcaca | 420 |
| gcggccctgg gctgcctggt caaggactac ttccccgaac cggtgacggt gtcgtggaac | 480 |
| tcaggcgccc tgaccagcgg cgtgcacacc ttcccggctg tcctacagtc ctcaggactc | 540 |
| tactccctca gcagcgtggt gaccgtgccc tccagcagct gggcaccca gacctacatc | 600 |
| tgcaacgtga atcacaagcc cagcaacacc aaggtggaca gagagttga gcccaaatct | 660 |
| tgtgacaaaa ctcacacatg cccaccgtgc ccagcacctg aagccgcggg ggcaccgtca | 720 |
| gtcttcctct tccccccaaa acccaaggac accctcatga tctcccggac ccctgaggtc | 780 |
| acatgcgtgg tggtggacgt gagccacgaa gaccctgagg tcaagttcaa ctggtacgtg | 840 |
| gacggcgtgg aggtgcataa tgccaagaca agccgcggg aggagcagta caacagcacg | 900 |
| taccgtgtgt cagcgtcct caccgtcctg caccaggact ggctgaatgg caaggagtac | 960 |
| aagtgcgcgg tctccaacaa agccctccca gccccatcg agaaaaccat ctccaaagcc | 1020 |
| aaagggcagc cccgagaacc acaggtgtac accctgcccc catcccggga tgagctgacc | 1080 |
| aagaaccagg tcagcctgac ctgcctggtc aaaggcttct atcccagcga catcgccgtg | 1140 |
| gagtgggaga gcaatgggca gccggagaac aactacaaga ccacgcctcc cgtgctggac | 1200 |

```
tccgacggct ccttcttcct ctatagcaag ctcaccgtgg acaagagcag gtggcagcag    1260
gggaacgtct tctcatgctc cgtgatgcat gaggctctgc acaaccacta cacgcagaag    1320
agcctctccc tgtctccggg t                                              1341
```

<210> SEQ ID NO 14
<211> LENGTH: 354
<212> TYPE: DNA
<213> ORGANISM: Artificial Sequence
<220> FEATURE:
<223> OTHER INFORMATION: synthesized

<400> SEQUENCE: 14

```
cagtcgctgg aggagtccgg gggtcgcctg gtcacgcctg gacgccccct gacactcacc     60
tgcacagtct ctggattcac catcagtagc aatgcaatga gctgggtccg ccaggctcca    120
gggaaggggc tggagtggat cggagtcatt actggtcgtg atatcacata ctacgcgaac    180
tgggcgaaag gccgattcac catctccaaa acctcgtcga ccacggtgga tctgaaaatg    240
accagtctga cagccgagga ctcggccacc tatttctgtg ccagagacgg tggttcttct    300
gctattacta gtaacaacat ttggggccca gggaccctgg tcaccgtctc gagc          354
```

<210> SEQ ID NO 15
<211> LENGTH: 447
<212> TYPE: PRT
<213> ORGANISM: Artificial Sequence
<220> FEATURE:
<223> OTHER INFORMATION: synthesized

<400> SEQUENCE: 15

```
Gln Ser Leu Glu Glu Ser Gly Gly Arg Leu Val Thr Pro Gly Thr Pro
1               5                   10                  15

Leu Thr Leu Thr Cys Thr Val Ser Gly Phe Thr Ile Ser Ser Asn Ala
            20                  25                  30

Met Ser Trp Val Arg Gln Ala Pro Gly Lys Gly Leu Glu Trp Ile Gly
        35                  40                  45

Val Ile Thr Gly Arg Asp Ile Thr Tyr Tyr Ala Asn Trp Ala Lys Gly
    50                  55                  60

Arg Phe Thr Ile Ser Lys Thr Ser Ser Thr Val Asp Leu Lys Met
65                  70                  75                  80

Thr Ser Leu Thr Ala Glu Asp Ser Ala Thr Tyr Phe Cys Ala Arg Asp
                85                  90                  95

Gly Gly Ser Ser Ala Ile Thr Ser Asn Asn Ile Trp Gly Pro Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205
```

Asn Thr Lys Val Asp Lys Arg Val Glu Pro Lys Ser Cys Asp Lys Thr
    210                 215                 220
His Thr Cys Pro Pro Cys Pro Ala Pro Glu Ala Ala Gly Ala Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Ala Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly
        435                 440                 445

<210> SEQ ID NO 16
<211> LENGTH: 118
<212> TYPE: PRT
<213> ORGANISM: Artificial Sequence
<220> FEATURE:
<223> OTHER INFORMATION: synthesized

<400> SEQUENCE: 16

Gln Ser Leu Glu Glu Ser Gly Gly Arg Leu Val Thr Pro Gly Thr Pro
1               5                   10                  15
Leu Thr Leu Thr Cys Thr Val Ser Gly Phe Thr Ile Ser Ser Asn Ala
            20                  25                  30
Met Ser Trp Val Arg Gln Ala Pro Gly Lys Gly Leu Glu Trp Ile Gly
        35                  40                  45
Val Ile Thr Gly Arg Asp Ile Thr Tyr Tyr Ala Asn Trp Ala Lys Gly
    50                  55                  60
Arg Phe Thr Ile Ser Lys Thr Ser Ser Thr Val Asp Leu Lys Met
65                  70                  75                  80
Thr Ser Leu Thr Ala Glu Asp Ser Ala Thr Tyr Phe Cys Ala Arg Asp
            85                  90                  95
Gly Gly Ser Ser Ala Ile Thr Ser Asn Asn Ile Trp Gly Pro Gly Thr
                100                 105                 110
Leu Val Thr Val Ser Ser
            115

<210> SEQ ID NO 17
<211> LENGTH: 657
<212> TYPE: DNA
<213> ORGANISM: Artificial Sequence
<220> FEATURE:
<223> OTHER INFORMATION: synthesized

<400> SEQUENCE: 17

```
gatgtcgtga tgacccagac tccatcctcc gtgtctgcag ctgtgggagg cacagtcacc      60
atcaattgcc aagccagtga gagcattagc agttggttag cctggtatca gcagaaacca     120
gggcagcctc ccaagctcct gatctacgaa gcatccaaac tggcatctgg ggtcccatcg     180
cggttcagtg cagtggatc  tgggacagag ttcactctca ccatcagcga cctggagtgt     240
gccgatgctg ccacttacta ctgtcaaggc tattttatt  ttattagtcg tacttatgta     300
aatgctttcg gcggagggac cgaggtggag ttcaaacgta cggtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgt       657
```

<210> SEQ ID NO 18
<211> LENGTH: 336
<212> TYPE: DNA
<213> ORGANISM: Artificial Sequence
<220> FEATURE:
<223> OTHER INFORMATION: synthesized

<400> SEQUENCE: 18

```
gatgtcgtga tgacccagac tccatcctcc gtgtctgcag ctgtgggagg cacagtcacc      60
atcaattgcc aagccagtga gagcattagc agttggttag cctggtatca gcagaaacca     120
gggcagcctc ccaagctcct gatctacgaa gcatccaaac tggcatctgg ggtcccatcg     180
cggttcagtg cagtggatc  tgggacagag ttcactctca ccatcagcga cctggagtgt     240
gccgatgctg ccacttacta ctgtcaaggc tattttatt  ttattagtcg tacttatgta     300
aatgctttcg gcggagggac cgaggtggag ttcaaa                                336
```

<210> SEQ ID NO 19
<211> LENGTH: 219
<212> TYPE: PRT
<213> ORGANISM: Artificial Sequence
<220> FEATURE:
<223> OTHER INFORMATION: synthesized

<400> SEQUENCE: 19

Asp Val Val Met Thr Gln Thr Pro Ser Ser Val Ser Ala Ala Val Gly
1               5                   10                  15

Gly Thr Val Thr Ile Asn Cys Gln Ala Ser Glu Ser Ile Ser Ser Trp
            20                  25                  30

Leu Ala Trp Tyr Gln Gln Lys Pro Gly Gln Pro Pro Lys Leu Leu Ile
        35                  40                  45

Tyr Glu Ala Ser Lys Leu Ala Ser Gly Val Pro Ser Arg Phe Ser Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Gly Tyr Phe Tyr Phe Ile Ser
                85                  90                  95

Arg Thr Tyr Val Asn Ala Phe Gly Gly Gly Thr Glu Val Glu Phe Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 20
<211> LENGTH: 112
<212> TYPE: PRT
<213> ORGANISM: Artificial Sequence
<220> FEATURE:
<223> OTHER INFORMATION: synthesized

<400> SEQUENCE: 20

Asp Val Val Met Thr Gln Thr Pro Ser Ser Val Ser Ala Ala Val Gly
1               5                   10                  15

Gly Thr Val Thr Ile Asn Cys Gln Ala Ser Glu Ser Ile Ser Ser Trp
            20                  25                  30

Leu Ala Trp Tyr Gln Gln Lys Pro Gly Gln Pro Pro Lys Leu Leu Ile
        35                  40                  45

Tyr Glu Ala Ser Lys Leu Ala Ser Gly Val Pro Ser Arg Phe Ser Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Gly Tyr Phe Tyr Phe Ile Ser
                85                  90                  95

Arg Thr Tyr Val Asn Ala Phe Gly Gly Gly Thr Glu Val Glu Phe Lys
            100                 105                 110

<210> SEQ ID NO 21
<211> LENGTH: 1341
<212> TYPE: DNA
<213> ORGANISM: Artificial Sequence
<220> FEATURE:
<223> OTHER INFORMATION: synthesized

<400> SEQUENCE: 21
cagtcgctgg aggagtccgg gggtcgcctg gtcacgcctg ggacgcccct gacactcacc      60
tgcacagtct ctggaatcga cctcagtagc aatgcaatga gctgggtccg ccaggctcca    120
gggaaggggc tggagtggat cggagtcatt actggtcgtg atatcacata ctacgcgagc    180
tgggcgaaag gccgattcac catctccaaa acctcgtcga ccacggtgga tctgaaaatg    240
accagtctga cagccgagga ctcggccacc tatttctgtg ccagagacgg tggttcttct    300

```
gctattaata gtaagaacat ttggggccaa ggcaccctgg tcaccgtctc gagcgctagc    360
accaagggcc catcggtctt cccctggca cctcctcca agagcacctc tgggggcaca    420
gcggccctgg gctgcctggt caaggactac ttccccgaac cggtgacggt gtcgtggaac    480
tcaggcgccc tgaccagcgg cgtgcacacc ttcccggctg tcctacagtc ctcaggactc    540
tactccctca gcagcgtggt gaccgtgccc tccagcagct gggcaccca gacctacatc    600 tgcaacgtga atcacaagcc cagcaacacc aaggtggaca gagagttga gcccaaatct    660 tgtgacaaaa ctcacacatg cccaccgtgc ccagcacctg aagccgcggg ggcaccgtca    720
gtcttcctct cccccccaaa acccaaggac accctcatga tctcccggac ccctgaggtc    780
acatgcgtgg tggtggacgt gagccacgaa gaccctgagg tcaagttcaa ctggtacgtg    840
gacggcgtgg aggtgcataa tgccaagaca aagccgcggg aggagcagta caacagcacg    900
taccgtgtgg tcagcgtcct caccgtcctg caccaggact ggctgaatgg caaggagtac    960
aagtgcgcgg tctccaacaa agccctccca gcccccatcg agaaaaccat ctccaaagcc   1020
aaagggcagc cccgagaacc acaggtgtac accctgcccc catcccggga tgagctgacc   1080
aagaaccagg tcagcctgac ctgcctggtc aaaggcttct atcccagcga catcgccgtg   1140
gagtgggaga gcaatgggca gccggagaac aactacaaga ccacgcctcc cgtgctggac   1200
tccgacggct ccttcttcct ctatagcaag ctcaccgtgg acaagagcag gtggcagcag   1260
gggaacgtct tctcatgctc cgtgatgcat gaggctctgc acaaccacta cacgcagaag   1320
agcctctccc tgtctccggg t                                              1341
```

<210> SEQ ID NO 22
<211> LENGTH: 354
<212> TYPE: DNA
<213> ORGANISM: Artificial Sequence
<220> FEATURE:
<223> OTHER INFORMATION: sunthesized

<400> SEQUENCE: 22

```
cagtcgctgg aggagtccgg gggtcgcctg gtcacgcctg gacgccccct gacactcacc     60
tgcacagtct ctggaatcga cctcagtagc aatgcaatga gctgggtccg ccaggctcca    120 gggaagggc tggagtggat cggagtcatt actggtcgtg atatcacata ctacgcgagc    180
tgggcgaaag gccgattcac catctccaaa acctcgtcga ccacggtgga tctgaaaatg    240
accagtctga cagccgagga ctcggccacc tatttctgtg ccagagacgg tggttcttct    300
gctattaata gtaagaacat ttggggccaa ggcaccctgg tcaccgtctc gagc          354
```

<210> SEQ ID NO 23
<211> LENGTH: 447
<212> TYPE: PRT
<213> ORGANISM: Artificial Sequence
<220> FEATURE:
<223> OTHER INFORMATION: sunthesized

<400> SEQUENCE: 23

```
Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Asn Ala
            20                  25                  30

Met Ser Trp Val Arg Gln Ala Pro Gly Lys Gly Leu Glu Trp Ile Gly
        35                  40                  45

Val Ile Thr Gly Arg Asp Ile Thr Tyr Tyr Ala Ser Trp Ala Lys Gly
    50                  55                  60
```

```
Arg Phe Thr Ile Ser Lys Thr Ser Thr Thr Val Asp Leu Lys Met
 65                  70                  75                  80

Thr Ser Leu Thr Ala Glu Asp Ser Ala Thr Tyr Phe Cys Ala Arg Asp
                 85                  90                  95

Gly Gly Ser Ser Ala Ile Asn Ser Lys Asn Ile Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Ala Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 24
<211> LENGTH: 118
<212> TYPE: PRT
<213> ORGANISM: Artificial Sequence
<220> FEATURE:
```

<223> OTHER INFORMATION: synthesized

<400> SEQUENCE: 24

Gln Ser Leu Glu Glu Ser Gly Gly Arg Leu Val Thr Pro Gly Thr Pro
1               5                   10                  15
Leu Thr Leu Thr Cys Thr Val Ser Gly Ile Asp Leu Ser Asn Ala
                20                  25                  30
Met Ser Trp Val Arg Gln Ala Pro Gly Lys Gly Leu Glu Trp Ile Gly
        35                  40                  45
Val Ile Thr Gly Arg Asp Ile Thr Tyr Tyr Ala Ser Trp Ala Lys Gly
    50                  55                  60
Arg Phe Thr Ile Ser Lys Thr Ser Thr Thr Val Asp Leu Lys Met
65                  70                  75                  80
Thr Ser Leu Thr Ala Glu Asp Ser Ala Thr Tyr Phe Cys Ala Arg Asp
                85                  90                  95
Gly Gly Ser Ser Ala Ile Asn Ser Lys Asn Ile Trp Gly Gln Gly Thr
            100                 105                 110
Leu Val Thr Val Ser Ser
        115

<210> SEQ ID NO 25
<211> LENGTH: 657
<212> TYPE: DNA
<213> ORGANISM: Artificial Sequence
<220> FEATURE:
<223> OTHER INFORMATION: Synthesized

<400> SEQUENCE: 25
gatgtcgtga tgacccagac tccagcctcc gtggaggcag ctgtgggagg cacagtcaca      60
atcaattgcc aagccagtga gagcattagc agttggttag cctggtatca gcagagacca     120
gggcagcctc ccaaactcct gatctacgaa gcatccaaac tggcgtctgg ggtcccatcg     180
cggttcaaag gcagtggatc tgggacagag ttcactctca ccatcagcga cctggagtgt     240
gccgatgctg ccacttacta ctgtcaaggc tatttttatt ttattagtcg tagttatgta     300
aatgctttcg gcgagggac cgaggtggtg gtcaaacgta cggtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgt       657

<210> SEQ ID NO 26
<211> LENGTH: 336
<212> TYPE: DNA
<213> ORGANISM: Artificial Sequence
<220> FEATURE:
<223> OTHER INFORMATION: Synthesized

<400> SEQUENCE: 26
gatgtcgtga tgacccagac tccagcctcc gtggaggcag ctgtgggagg cacagtcaca      60
atcaattgcc aagccagtga gagcattagc agttggttag cctggtatca gcagagacca     120
gggcagcctc ccaaactcct gatctacgaa gcatccaaac tggcgtctgg ggtcccatcg     180
cggttcaaag gcagtggatc tgggacagag ttcactctca ccatcagcga cctggagtgt     240

```
gccgatgctg ccacttacta ctgtcaaggc tattttatt ttattagtcg tagttatgta    300
aatgctttcg gcggagggac cgaggtggtg gtcaaa                             336
```

<210> SEQ ID NO 27
<211> LENGTH: 219
<212> TYPE: PRT
<213> ORGANISM: Artificial Sequence
<220> FEATURE:
<223> OTHER INFORMATION: Synthesized

<400> SEQUENCE: 27

```
Asp Val Val Met Thr Gln Thr Pro Ala Ser Val Glu Ala Ala Val Gly
1               5                   10                  15

Gly Thr Val Thr Ile Asn Cys Gln Ala Ser Glu Ser Ile Ser Ser Trp
            20                  25                  30

Leu Ala Trp Tyr Gln Gln Arg Pro Gly Gln Pro Pro Lys Leu Leu Ile
        35                  40                  45

Tyr Glu Ala Ser Lys Leu Ala Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Gly Tyr Phe Tyr Phe Ile Ser
                85                  90                  95

Arg Ser Tyr Val Asn Ala Phe Gly Gly Gly Thr Glu Val Val Val Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 28
<211> LENGTH: 112
<212> TYPE: PRT
<213> ORGANISM: Artificial Sequence
<220> FEATURE:
<223> OTHER INFORMATION: Synthesized

<400> SEQUENCE: 28

```
Asp Val Val Met Thr Gln Thr Pro Ala Ser Val Glu Ala Ala Val Gly
1               5                   10                  15

Gly Thr Val Thr Ile Asn Cys Gln Ala Ser Glu Ser Ile Ser Ser Trp
            20                  25                  30

Leu Ala Trp Tyr Gln Gln Arg Pro Gly Gln Pro Pro Lys Leu Leu Ile
        35                  40                  45

Tyr Glu Ala Ser Lys Leu Ala Ser Gly Val Pro Ser Arg Phe Lys Gly
    50                  55                  60
```

| | | | | | | | | | | | | | | |
|---|---|---|---|---|---|---|---|---|---|---|---|---|---|---|
|Ser|Gly|Ser|Gly|Thr|Glu|Phe|Thr|Leu|Thr|Ile|Ser|Asp|Leu|Glu|Cys|
|65| | | |70| | | |75| | | |80| | |

Ala Asp Ala Ala Thr Tyr Tyr Cys Gln Gly Tyr Phe Tyr Phe Ile Ser
            85                  90                  95

Arg Ser Tyr Val Asn Ala Phe Gly Gly Gly Thr Glu Val Val Val Lys
        100                 105                 110

<210> SEQ ID NO 29
<211> LENGTH: 1341
<212> TYPE: DNA
<213> ORGANISM: Artificial Sequence
<220> FEATURE:
<223> OTHER INFORMATION: Synthesized

<400> SEQUENCE: 29

```
cagtcactgg aggagtccgg gggtcgcctg gtcacgcctg ggacacccct gacactcacc      60
tgcacagtct ctggaatcga cctcagtagt aatgcaatga gctgggtccg ccaggctcca     120
gggaaggggc tggagtggat cggagtcatt actggtcgtg atattaatta ctacgcgagc     180
tgggcgaaag gccgattcac catctccaaa acctcgtcga ccacggtgga tctgaaaatg     240
accagtctga cagccgagga ctcggccacc tatttctgtg ccagagacgg tggttcttct     300
gctattacta gtaagaacat ttggggccca ggcaccctgg tcaccgtctc gagcgctagc     360
accaagggcc catcggtctt ccccctggca ccctcctcca agagcacctc tgggggcaca     420
gcggccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct gggcaccca gacctacatc      600
tgcaacgtga atcacaagcc cagcaacacc aaggtggaca gagagttga gcccaaatct     660
tgtgacaaaa ctcacacatg cccaccgtgc ccagcacctg aagccgcggg ggcaccgtca     720
gtcttcctct tccccccaaa acccaaggac accctcatga tctcccggac ccctgaggtc     780
acatgcgtgg tggtggacgt gagccacgaa gaccctgagg tcaagttcaa ctggtacgtg     840
gacggcgtgg aggtgcataa tgccaagaca aagccgcggg aggagcagta caacagcacg     900
taccgtgtgg tcagcgtcct caccgtcctg caccaggact ggctgaatgg caaggagtac     960
aagtgcgcgg tctccaacaa agccctccca gcccccatcg agaaaaccat ctccaaagcc    1020
aaagggcagc cccgagaacc acaggtgtac accctgcccc catcccggga tgagctgacc    1080
aagaaccagg tcagcctgac ctgcctggtc aaaggcttct atcccagcga catcgccgtg    1140
gagtgggaga gcaatgggca gccggagaac aactacaaga ccacgcctcc cgtgctggac    1200
tccgacggct ccttcttcct ctatagcaag ctcaccgtgg acaagagcag gtggcagcag    1260
gggaacgtct tctcatgctc cgtgatgcat gaggctctgc acaaccacta cacgcagaag    1320
agcctctccc tgtctccggg t                                              1341
```

<210> SEQ ID NO 30
<211> LENGTH: 354
<212> TYPE: DNA
<213> ORGANISM: Artificial Sequence
<220> FEATURE:
<223> OTHER INFORMATION: Synthesized

<400> SEQUENCE: 30

```
cagtcactgg aggagtccgg gggtcgcctg gtcacgcctg ggacacccct gacactcacc      60
tgcacagtct ctggaatcga cctcagtagt aatgcaatga gctgggtccg ccaggctcca     120
```

```
gggaaggggc tggagtggat cggagtcatt actggtcgtg atattaatta ctacgcgagc    180
tgggcgaaag gccgattcac catctccaaa acctcgtcga ccacggtgga tctgaaaatg    240
accagtctga cagccgagga ctcggccacc tatttctgtg ccagagacgg tggttcttct    300
gctattacta gtaagaacat ttggggccca ggcaccctgg tcaccgtctc gagc          354
```

<210> SEQ ID NO 31
<211> LENGTH: 447
<212> TYPE: PRT
<213> ORGANISM: Artificial Sequence
<220> FEATURE:
<223> OTHER INFORMATION: Synthesized

<400> SEQUENCE: 31

```
Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Asn Ala
            20                  25                  30

Met Ser Trp Val Arg Gln Ala Pro Gly Lys Gly Leu Glu Trp Ile Gly
        35                  40                  45

Val Ile Thr Gly Arg Asp Ile Asn Tyr Tyr Ala Ser Trp Ala Lys Gly
    50                  55                  60

Arg Phe Thr Ile Ser Lys Thr Ser Ser Thr Thr Val Asp Leu Lys Met
65                  70                  75                  80

Thr Ser Leu Thr Ala Glu Asp Ser Ala Thr Tyr Phe Cys Ala Arg Asp
                85                  90                  95

Gly Gly Ser Ser Ala Ile Thr Ser Lys Asn Ile Trp Gly Pro Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320
```

Lys Cys Ala Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 32
<211> LENGTH: 118
<212> TYPE: PRT
<213> ORGANISM: Artificial Sequence
<220> FEATURE:
<223> OTHER INFORMATION: Synthesized

<400> SEQUENCE: 32

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Asn Ala
            20                  25                  30

Met Ser Trp Val Arg Gln Ala Pro Gly Lys Gly Leu Glu Trp Ile Gly
        35                  40                  45

Val Ile Thr Gly Arg Asp Ile Asn Tyr Tyr Ala Ser Trp Ala Lys Gly
    50                  55                  60

Arg Phe Thr Ile Ser Lys Thr Ser Ser Thr Thr Val Asp Leu Lys Met
65                  70                  75                  80

Thr Ser Leu Thr Ala Glu Asp Ser Ala Thr Tyr Phe Cys Ala Arg Asp
                85                  90                  95

Gly Gly Ser Ser Ala Ile Thr Ser Lys Asn Ile Trp Gly Pro Gly Thr
            100                 105                 110

Leu Val Thr Val Ser Ser
        115

<210> SEQ ID NO 33
<211> LENGTH: 657
<212> TYPE: DNA
<213> ORGANISM: Artificial Sequence
<220> FEATURE:
<223> OTHER INFORMATION: synthesized

<400> SEQUENCE: 33
gatgtcgtga tgacccagac tccagcctcc gtggaggcag ctgtgggagg cacagtcacc    60
atcaattgcc aagccagtga gagcattagc agttggttag cctggtatca gcagagacca   120
gggcagcctc ccaagctcct gatctacgaa gcatccaaac tggcatctgg ggtcccatcg   180
cggttcagtg gcagtggatc tgggacagag ttcactctca ccatcagcga cctggagtgt   240
gccgatgctg ccacttacta ctgtcagggc tatttttatt ttattagtcg tagttatgta   300

```
aatgctttcg gcggagggac cgaggtggtg ttcaaacgta cggtggctgc accatctgtc      360
ttcatcttcc cgccatctga tgagcagttg aaatctggaa ctgcctctgt tgtgtgcctg      420
ctgaataact tctatcccag agaggccaaa gtacagtgga aggtggataa cgccctccaa      480
tcgggtaact cccaggagag tgtcacagag caggacagca aggacagcac ctacagcctc      540
agcagcaccc tgacgctgag caaagcagac tacgagaaac acaaagtcta cgcctgcgaa      600
gtcacccatc agggcctgag ctcgcccgtc acaaagagct tcaacagggg agagtgt        657
```

```
<210> SEQ ID NO 34
<211> LENGTH: 336
<212> TYPE: DNA
<213> ORGANISM: Artificial Sequence
<220> FEATURE:
<223> OTHER INFORMATION: synthesized

<400> SEQUENCE: 34
gatgtcgtga tgacccagac tccagcctcc gtggaggcag ctgtgggagg cacagtcacc       60
atcaattgcc aagccagtga gagcattagc agttggttag cctggtatca gcagagacca      120
gggcagcctc ccaagctcct gatctacgaa gcatccaaac tggcatctgg ggtcccatcg      180
cggttcagtg gcagtggatc tgggacagag ttcactctca ccatcagcga cctggagtgt      240
gccgatgctg ccacttacta ctgtcagggc tattttatt ttattagtcg tagttatgta      300
aatgctttcg gcggagggac cgaggtggtg ttcaaa                                336
```

```
<210> SEQ ID NO 35
<211> LENGTH: 219
<212> TYPE: PRT
<213> ORGANISM: Artificial Sequence
<220> FEATURE:
<223> OTHER INFORMATION: synthesized

<400> SEQUENCE: 35

Asp Val Val Met Thr Gln Thr Pro Ala Ser Val Glu Ala Ala Val Gly
1               5                   10                  15

Gly Thr Val Thr Ile Asn Cys Gln Ala Ser Glu Ser Ile Ser Ser Trp
            20                  25                  30

Leu Ala Trp Tyr Gln Gln Arg Pro Gly Gln Pro Pro Lys Leu Leu Ile
        35                  40                  45

Tyr Glu Ala Ser Lys Leu Ala Ser Gly Val Pro Ser Arg Phe Ser Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Gly Tyr Phe Tyr Phe Ile Ser
                85                  90                  95

Arg Ser Tyr Val Asn Ala Phe Gly Gly Gly Thr Glu Val Val Phe Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190
```

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 36
<211> LENGTH: 112
<212> TYPE: PRT
<213> ORGANISM: Artificial Sequence
<220> FEATURE:
<223> OTHER INFORMATION: synthesized

<400> SEQUENCE: 36

Asp Val Val Met Thr Gln Thr Pro Ala Ser Val Glu Ala Ala Val Gly
1               5                   10                  15

Gly Thr Val Thr Ile Asn Cys Gln Ala Ser Glu Ser Ile Ser Ser Trp
            20                  25                  30

Leu Ala Trp Tyr Gln Gln Arg Pro Gly Gln Pro Pro Lys Leu Leu Ile
        35                  40                  45

Tyr Glu Ala Ser Lys Leu Ala Ser Gly Val Pro Ser Arg Phe Ser Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Gly Tyr Phe Tyr Phe Ile Ser
                85                  90                  95

Arg Ser Tyr Val Asn Ala Phe Gly Gly Gly Thr Glu Val Val Phe Lys
            100                 105                 110

<210> SEQ ID NO 37
<211> LENGTH: 1341
<212> TYPE: DNA
<213> ORGANISM: Artificial Sequence
<220> FEATURE:
<223> OTHER INFORMATION: synthesized

<400> SEQUENCE: 37
cagtcgctgg aggagtccgg gggtcgcctg gtcacgcctg ggacacccct gacactcacc      60
tgcacagtct ctggaatcga cctcagtagc aatgcaatga gctgggtccg ccaggctcca     120
gggaaggggc tggagtggat cggagtcatt actggtcgtg atatcacata ctacgcgagc     180
tgggcgaaag gccgattcac catctccaaa acctcgtcga ccacggtgga tctgaaaatg     240
accagtctga gaccgagga ctcggccacc tatttctgtg ccagagacgg tggttcttct     300
gctattacta gtaagaacat ttggggcccg ggcaccctgg tcaccgtctc gagcgctagc     360
accaagggcc catcggtctt ccccctggca ccctcctcca agagcacctc tgggggcaca     420
gcggccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct tgggcaccca gacctacatc     600
tgcaacgtga atcacaagcc cagcaacacc aaggtggaca gagagttga gcccaaatct     660
tgtgacaaaa ctcacacatg cccaccgtgc ccagcacctg aagccgcggg ggcaccgtca     720
gtcttcctct tccccccaaa acccaaggac accctcatga tctcccggac ccctgaggtc     780
acatgcgtgg tggtggacgt gagccacgaa gaccctgagg tcaagttcaa ctggtacgtg     840
gacggcgtgg aggtgcataa tgccaagaca agccgcgggg aggagcagta caacagcacg     900
taccgtgtgg tcagcgtcct caccgtcctg caccaggact ggctgaatgg caaggagtac     960

```
aagtgcgcgg tctccaacaa agccctccca gcccccatcg agaaaaccat ctccaaagcc    1020
aaagggcagc cccgagaacc acaggtgtac accctgcccc catcccggga tgagctgacc    1080
aagaaccagg tcagcctgac ctgcctggtc aaaggcttct atcccagcga catcgccgtg    1140
gagtgggaga gcaatgggca gccggagaac aactacaaga ccacgcctcc cgtgctggac    1200
tccgacggct ccttcttcct ctatagcaag ctcaccgtgg acaagagcag gtggcagcag    1260
gggaacgtct tctcatgctc cgtgatgcat gaggctctgc acaaccacta cacgcagaag    1320
agcctctccc tgtctccggg t                                              1341

<210> SEQ ID NO 38
<211> LENGTH: 354
<212> TYPE: DNA
<213> ORGANISM: Artificial Sequence
<220> FEATURE:
<223> OTHER INFORMATION: synthesized

<400> SEQUENCE: 38
cagtcgctgg aggagtccgg gggtcgcctg gtcacgcctg gacacccct gacactcacc      60 tgcacagtct ctggaatcga cctcagtagc aatgcaatga gctgggtccg ccaggctcca    120 gggaagggc tggagtggat cggagtcatt actggtcgtg atatcacata ctacgcgagc    180
tgggcgaaag gccgattcac catctccaaa acctcgtcga ccacggtgga tctgaaaatg    240
accagtctga cagccgagga ctcggccacc tatttctgtg ccagagacgg tggttcttct    300
gctattacta gtaagaacat ttggggcccg ggcaccctgg tcaccgtctc gagc          354

<210> SEQ ID NO 39
<211> LENGTH: 447
<212> TYPE: PRT
<213> ORGANISM: Artificial Sequence
<220> FEATURE:
<223> OTHER INFORMATION: synthesized

<400> SEQUENCE: 39
```

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Asn Ala
            20                  25                  30

Met Ser Trp Val Arg Gln Ala Pro Gly Lys Gly Leu Glu Trp Ile Gly
        35                  40                  45

Val Ile Thr Gly Arg Asp Ile Thr Tyr Tyr Ala Ser Trp Ala Lys Gly
    50                  55                  60

Arg Phe Thr Ile Ser Lys Thr Ser Ser Thr Val Asp Leu Lys Met
65                  70                  75                  80

Thr Ser Leu Thr Ala Glu Asp Ser Ala Thr Tyr Phe Cys Ala Arg Asp
                85                  90                  95

Gly Gly Ser Ser Ala Ile Thr Ser Lys Asn Ile Trp Gly Pro Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

```
Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Ala Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 40
<211> LENGTH: 118
<212> TYPE: PRT
<213> ORGANISM: Artificial Sequence
<220> FEATURE:
<223> OTHER INFORMATION: synthesized

<400> SEQUENCE: 40

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Asn Ala
            20                  25                  30

Met Ser Trp Val Arg Gln Ala Pro Gly Lys Gly Leu Glu Trp Ile Gly
        35                  40                  45

Val Ile Thr Gly Arg Asp Ile Thr Tyr Tyr Ala Ser Trp Ala Lys Gly
    50                  55                  60

Arg Phe Thr Ile Ser Lys Thr Ser Ser Thr Val Asp Leu Lys Met
65                  70                  75                  80

Thr Ser Leu Thr Ala Glu Asp Ser Ala Thr Tyr Phe Cys Ala Arg Asp
            85                  90                  95
```

Gly Gly Ser Ser Ala Ile Thr Ser Lys Asn Ile Trp Gly Pro Gly Thr
            100                 105                 110

Leu Val Thr Val Ser Ser
        115

<210> SEQ ID NO 41
<211> LENGTH: 651
<212> TYPE: DNA
<213> ORGANISM: Artificial Sequence
<220> FEATURE:
<223> OTHER INFORMATION: synthesized

<400> SEQUENCE: 41
gatgtcgtga tgacccagac tccagcctcc gtgtctgaac ctgtgggagg cacagtcacc      60
atcaagtgcc aggccagtga gagcattaat agtaatgtag cctggtatca gcagaaacca     120
gggcagcgtc ccaagctcct gatctatgat tcatccactc tggaatctgg ggtcccatcg     180
cggttcaaag gcagtagatc tgggacagag ttcactctca ccatcagcga cctggagtgt     240
gccgatgccg ccacttacta ctgtcaatgt agtagttatg gtagtagtta tgttggtggt     300
ttcggcggag ggaccgaggt ggtgttcaaa cgtacggtgg ctgcaccatc tgtcttcatc     360
ttcccgccat ctgatgagca gttgaaatct ggaactgcct ctgttgtgtg cctgctgaat     420
aacttctatc ccagagaggc caaagtacag tggaaggtgg ataacgccct ccaatcgggt     480
aactcccagg agagtgtcac agagcaggac agcaaggaca gcacctacag cctcagcagc     540
accctgacgc tgagcaaagc agactacgag aaacacaaag tctacgcctg cgaagtcacc     600
catcagggcc tgagctcgcc cgtcacaaag agcttcaaca ggggagagtg t              651

<210> SEQ ID NO 42
<211> LENGTH: 330
<212> TYPE: DNA
<213> ORGANISM: Artificial Sequence
<220> FEATURE:
<223> OTHER INFORMATION: synthesized

<400> SEQUENCE: 42
gatgtcgtga tgacccagac tccagcctcc gtgtctgaac ctgtgggagg cacagtcacc      60
atcaagtgcc aggccagtga gagcattaat agtaatgtag cctggtatca gcagaaacca     120
gggcagcgtc ccaagctcct gatctatgat tcatccactc tggaatctgg ggtcccatcg     180
cggttcaaag gcagtagatc tgggacagag ttcactctca ccatcagcga cctggagtgt     240
gccgatgccg ccacttacta ctgtcaatgt agtagttatg gtagtagtta tgttggtggt     300
ttcggcggag ggaccgaggt ggtgttcaaa                                      330

<210> SEQ ID NO 43
<211> LENGTH: 217
<212> TYPE: PRT
<213> ORGANISM: Artificial Sequence
<220> FEATURE:
<223> OTHER INFORMATION: synthesized

<400> SEQUENCE: 43

Asp Val Val Met Thr Gln Thr Pro Ala Ser Val Ser Glu Pro Val Gly
1               5                   10                  15

Gly Thr Val Thr Ile Lys Cys Gln Ala Ser Glu Ser Ile Asn Ser Asn
            20                  25                  30

Val Ala Trp Tyr Gln Gln Lys Pro Gly Gln Arg Pro Lys Leu Leu Ile
        35                  40                  45

Tyr Asp Ser Ser Thr Leu Glu Ser Gly Val Pro Ser Arg Phe Lys Gly
 50                  55                  60

Ser Arg Ser Gly Thr Glu Phe Thr Leu Thr Ile Ser Asp Leu Glu Cys
 65                  70                  75                  80

Ala Asp Ala Ala Thr Tyr Tyr Cys Gln Cys Ser Ser Tyr Gly Ser Ser
                 85                  90                  95

Tyr Val Gly Gly Phe Gly Gly Gly Thr Glu Val Val Phe Lys Arg Thr
                100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 44
<211> LENGTH: 110
<212> TYPE: PRT
<213> ORGANISM: Artificial Sequence
<220> FEATURE:
<223> OTHER INFORMATION: synthesized

<400> SEQUENCE: 44

Asp Val Val Met Thr Gln Thr Pro Ala Ser Val Ser Glu Pro Val Gly
 1               5                  10                  15

Gly Thr Val Thr Ile Lys Cys Gln Ala Ser Glu Ser Ile Asn Ser Asn
                20                  25                  30

Val Ala Trp Tyr Gln Gln Lys Pro Gly Gln Arg Pro Lys Leu Leu Ile
            35                  40                  45

Tyr Asp Ser Ser Thr Leu Glu Ser Gly Val Pro Ser Arg Phe Lys Gly
 50                  55                  60

Ser Arg Ser Gly Thr Glu Phe Thr Leu Thr Ile Ser Asp Leu Glu Cys
 65                  70                  75                  80

Ala Asp Ala Ala Thr Tyr Tyr Cys Gln Cys Ser Ser Tyr Gly Ser Ser
                 85                  90                  95

Tyr Val Gly Gly Phe Gly Gly Gly Thr Glu Val Val Phe Lys
                100                 105                 110

<210> SEQ ID NO 45
<211> LENGTH: 1341
<212> TYPE: DNA
<213> ORGANISM: Artificial Sequence
<220> FEATURE:
<223> OTHER INFORMATION: synthesized

<400> SEQUENCE: 45
cagtcgctgg aggagtccgg gggtcgcctg gtcacgcctg gacacccct gacactcacc      60 tgcacagtct ctggaatcga cctcagtagc aatgcaatga gctgggtccg ccaggctcca     120

-continued

```
gggaagggc tggagtggat cggagtcatt actggtcgtg atatcacata ctacgcgagc      180
tgggcgaaag gccgattcac catctccaaa acctcgtcga ccacggtgga tctgaaaatg      240
cccagtctga cagccgagga ctcggccacc tatttctgtg ccagagacgg tggttcttct      300
gctattacta gtaagaacat ttggggccag gggaccctcg tcaccgtctc gagcgctagc      360
accaagggcc catcggtctt ccccctggca ccctcctcca agagcacctc tgggggcaca      420
gcggccctgg gctgcctggt caaggactac ttccccgaac cggtgacggt gtcgtggaac      480
tcaggcgccc tgaccagcgg cgtgcacacc ttcccggctg tcctacagtc ctcaggactc      540
tactccctca gcagcgtggt gaccgtgccc tccagcagct gggcaccca gacctacatc      600 tgcaacgtga atcacaagcc cagcaacacc aaggtggaca agagagttga gcccaaatct      660
tgtgacaaaa ctcacacatg cccaccgtgc ccagcacctg aagccgcggg ggcaccgtca      720
gtcttcctct tccccccaaa acccaaggac accctcatga tctcccggac ccctgaggtc      780
acatgcgtgg tggtggacgt gagccacgaa gaccctgagg tcaagttcaa ctggtacgtg      840
gacggcgtgg aggtgcataa tgccaagaca agccgcggg aggagcagta caacagcacg      900
taccgtgtgg tcagcgtcct caccgtcctg caccaggact ggctgaatgg caaggagtac      960 aagtgcgcg tctccaacaa agccctccca gcccccatcg agaaaaccat ctccaaagcc     1020
aaagggcagc cccgagaacc acaggtgtac accctgcccc catcccggga tgagctgacc     1080
aagaaccagg tcagcctgac ctgcctggtc aaaggcttct atcccagcga catcgccgtg     1140
gagtgggaga gcaatgggca gccggagaac aactacaaga ccacgcctcc cgtgctggac     1200
tccgacggct ccttcttcct ctatagcaag ctcaccgtgg acaagagcag gtggcagcag     1260
gggaacgtct tctcatgctc cgtgatgcat gaggctctgc acaaccacta cacgcagaag     1320
agcctctccc tgtctccggg t                                                1341
```

<210> SEQ ID NO 46
<211> LENGTH: 354
<212> TYPE: DNA
<213> ORGANISM: Artificial Sequence
<220> FEATURE:
<223> OTHER INFORMATION: synthesized

<400> SEQUENCE: 46

```
cagtcgctgg aggagtccgg gggtcgcctg gtcacgcctg gacacccct gacactcacc       60 tgcacagtct ctggaatcga cctcagtagc aatgcaatga gctgggtccg ccaggctcca     120 gggaagggc tggagtggat cggagtcatt actggtcgtg atatcacata ctacgcgagc     180
tgggcgaaag gccgattcac catctccaaa acctcgtcga ccacggtgga tctgaaaatg     240
cccagtctga cagccgagga ctcggccacc tatttctgtg ccagagacgg tggttcttct     300
gctattacta gtaagaacat ttggggccag gggaccctcg tcaccgtctc gagc           354
```

<210> SEQ ID NO 47
<211> LENGTH: 447
<212> TYPE: PRT
<213> ORGANISM: Artificial Sequence
<220> FEATURE:
<223> OTHER INFORMATION: synthesized

<400> SEQUENCE: 47

```
Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Asn Ala
            20                  25                  30
```

Met Ser Trp Val Arg Gln Ala Pro Gly Lys Gly Leu Glu Trp Ile Gly
        35                  40                  45

Val Ile Thr Gly Arg Asp Ile Thr Tyr Tyr Ala Ser Trp Ala Lys Gly
        50                  55                  60

Arg Phe Thr Ile Ser Lys Thr Ser Thr Thr Val Asp Leu Lys Met
65                  70                  75                  80

Pro Ser Leu Thr Ala Glu Asp Ser Ala Thr Tyr Phe Cys Ala Arg Asp
                85                  90                  95

Gly Gly Ser Ser Ala Ile Thr Ser Lys Asn Ile Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Ala Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 48
<211> LENGTH: 118
<212> TYPE: PRT
<213> ORGANISM: Artificial Sequence
<220> FEATURE:
<223> OTHER INFORMATION: synthesized

<400> SEQUENCE: 48

```
Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Asn Ala
            20                  25                  30

Met Ser Trp Val Arg Gln Ala Pro Gly Lys Gly Leu Glu Trp Ile Gly
        35                  40                  45

Val Ile Thr Gly Arg Asp Ile Thr Tyr Tyr Ala Ser Trp Ala Lys Gly
    50                  55                  60

Arg Phe Thr Ile Ser Lys Thr Ser Ser Thr Thr Val Asp Leu Lys Met
65                  70                  75                  80

Pro Ser Leu Thr Ala Glu Asp Ser Ala Thr Tyr Phe Cys Ala Arg Asp
                85                  90                  95

Gly Gly Ser Ser Ala Ile Thr Ser Lys Asn Ile Trp Gly Gln Gly Thr
            100                 105                 110

Leu Val Thr Val Ser Ser
        115
```

<210> SEQ ID NO 49
<211> LENGTH: 657
<212> TYPE: DNA
<213> ORGANISM: Artificial Sequence
<220> FEATURE:
<223> OTHER INFORMATION: synthesized

<400> SEQUENCE: 49

```
gacgtcgtga tgacccagtc tccttccacc ctgtctgcat ctgtaggaga cagagtcacc      60
atcaattgcc aagccagtga gagcattagc agttggttag cctggtatca gcagaaacca     120
gggaaagccc ctaagctcct gatctatgaa gcatccaaac tggcatctgg ggtcccatca     180
aggttcagcg gcagtggatc tgggacagaa ttcactctca ccatcagcag cctgcagcct     240
gatgattttg caacttatta ctgccaaggc tattttatt ttattagtcg tacttatgta      300
aattctttcg gcggagggac caaggtggag atcaaacgta cggtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgt       657
```

<210> SEQ ID NO 50
<211> LENGTH: 336
<212> TYPE: DNA
<213> ORGANISM: Artificial Sequence
<220> FEATURE:
<223> OTHER INFORMATION: synthesized

<400> SEQUENCE: 50

```
gacgtcgtga tgacccagtc tccttccacc ctgtctgcat ctgtaggaga cagagtcacc      60
atcaattgcc aagccagtga gagcattagc agttggttag cctggtatca gcagaaacca     120
```

```
gggaaagccc ctaagctcct gatctatgaa gcatccaaac tggcatctgg ggtcccatca    180
aggttcagcg gcagtggatc tgggacagaa ttcactctca ccatcagcag cctgcagcct    240
gatgattttg caacttatta ctgccaaggc tattttatt ttattagtcg tacttatgta     300
aattctttcg gcggagggac caaggtggag atcaaa                              336
```

```
<210> SEQ ID NO 51
<211> LENGTH: 219
<212> TYPE: PRT
<213> ORGANISM: Artificial Sequence
<220> FEATURE:
<223> OTHER INFORMATION: synthesized

<400> SEQUENCE: 51
```

Asp Val Val Met Thr Gln Ser Pro Ser Thr Leu Ser Ala Ser Val Gly
1               5                   10                  15

Asp Arg Val Thr Ile Asn Cys Gln Ala Ser Glu Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Lys Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gly Tyr Phe Tyr Phe Ile Ser
                85                  90                  95

Arg Thr Tyr Val Asn Ser Phe Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

```
<210> SEQ ID NO 52
<211> LENGTH: 112
<212> TYPE: PRT
<213> ORGANISM: Artificial Sequence
<220> FEATURE:
<223> OTHER INFORMATION: synthesized

<400> SEQUENCE: 52
```

Asp Val Val Met Thr Gln Ser Pro Ser Thr Leu Ser Ala Ser Val Gly
1               5                   10                  15

Asp Arg Val Thr Ile Asn Cys Gln Ala Ser Glu Ser Ile Ser Ser Trp
            20                  25                  30

Leu Ala Trp Tyr Gln Gln Lys Pro Gly Lys Ala Pro Lys Leu Leu Ile
        35                  40                  45

```
Tyr Glu Ala Ser Lys Leu Ala Ser Gly Val Pro Ser Arg Phe Ser Gly
         50                  55                  60

Ser Gly Ser Gly Thr Glu Phe Thr Leu Thr Ile Ser Ser Leu Gln Pro
 65              70                  75                  80

Asp Asp Phe Ala Thr Tyr Tyr Cys Gln Gly Tyr Phe Tyr Phe Ile Ser
                 85                  90                  95

Arg Thr Tyr Val Asn Ser Phe Gly Gly Gly Thr Lys Val Glu Ile Lys
                100                 105                 110
```

<210> SEQ ID NO 53
<211> LENGTH: 1347
<212> TYPE: DNA
<213> ORGANISM: Artificial Sequence
<220> FEATURE:
<223> OTHER INFORMATION: synthesized

<400> SEQUENCE: 53

| | | |
|---|---|---|
| gaggtgcagc tggtggagtc tgggggaggc ttggtccagc ctggggggtc cctgagactc | 60 |
| tcctgtgcag cctctggatt caccatcagt accaatgcaa tgagctgggt ccgccaggct | 120 |
| ccagggaagg ggctggagtg gatcggagtc attactggtc gtgatatcac atactacgcg | 180 |
| agctgggcga aaggcagatt caccatctcc agagacaatt ccaagaacac gctgtatctt | 240 |
| caaatgaaca gcctgagagc cgaggacacg gctgtgtatt actgtgcgag agacggtggt | 300 |
| tcttctgcta ttactagtaa caacatttgg ggccagggaa ccctggtcac cgtctcgagc | 360 |
| gctagcacca agggcccatc ggtcttcccc ctggcaccct cctccaagag cacctctggg | 420 |
| ggcacagcgg ccctgggctg cctggtcaag gactacttcc ccgaaccggt gacggtgtcg | 480 |
| tggaactcag gcgccctgac cagcggcgtg cacaccttcc cggctgtcct acagtcctca | 540 |
| ggactctact ccctcagcag cgtggtgacc gtgccctcca gcagcttggg cacccagacc | 600 |
| tacatctgca acgtgaatca caagcccagc aacaccaagg tggacaagag agttgagccc | 660 |
| aaatcttgtg acaaaactca cacatgccca ccgtgcccag cacctgaagc cgcggggggca | 720 |
| ccgtcagtct tcctcttccc cccaaaaccc aaggacaccc tcatgatctc ccggacccct | 780 |
| gaggtcacat gcgtggtggt ggacgtgagc cacgaagacc ctgaggtcaa gttcaactgg | 840 |
| tacgtggacg gcgtggaggt gcataatgcc aagacaaagc cgcgggagga gcagtacaac | 900 |
| agcacgtacc gtgtggtcag cgtcctcacc gtcctgcacc aggactggct gaatggcaag | 960 |
| gagtacaagt gcgcggtctc caacaaagcc ctcccagccc ccatcgagaa aaccatctcc | 1020 |
| aaagccaaag gcagccccccg agaaccacag gtgtacaccc tgcccccatc ccgggatgag | 1080 |
| ctgaccaaga accaggtcag cctgacctgc ctggtcaaag gcttctatcc cagcgacatc | 1140 |
| gccgtggagt gggagagcaa tgggcagccg gagaacaact acaagaccac gcctcccgtg | 1200 |
| ctggactccg acggctcctt cttcctctat agcaagctca ccgtggacaa gagcaggtgg | 1260 |
| cagcagggga acgtcttctc atgctccgtg atgcatgagg ctctgcacaa ccactacacg | 1320 |
| cagaagagcc tctccctgtc tccgggt | 1347 |

<210> SEQ ID NO 54
<211> LENGTH: 360
<212> TYPE: DNA
<213> ORGANISM: Artificial Sequence
<220> FEATURE:
<223> OTHER INFORMATION: synthesized

<400> SEQUENCE: 54

```
gaggtgcagc tggtggagtc tgggggaggc ttggtccagc ctggggggtc cctgagactc      60
tcctgtgcag cctctggatt caccatcagt accaatgcaa tgagctgggt ccgccaggct     120
ccagggaagg gctggagtg atcggagtc attactggtc gtgatatcac atactacgcg      180
agctgggcga aaggcagatt caccatctcc agagacaatt ccaagaacac gctgtatctt     240
caaatgaaca gcctgagagc cgaggacacg gctgtgtatt actgtgcgag agacggtggt     300
tcttctgcta ttactagtaa caacatttgg ggccagggaa ccctggtcac cgtctcgagc     360
```

<210> SEQ ID NO 55
<211> LENGTH: 449
<212> TYPE: PRT
<213> ORGANISM: Artificial Sequence
<220> FEATURE:
<223> OTHER INFORMATION: synthesized

<400> SEQUENCE: 55

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Ile Ser Thr Asn
             20                  25                  30

Ala Met Ser Trp Val Arg Gln Ala Pro Gly Lys Gly Leu Glu Trp Ile
         35                  40                  45

Gly Val Ile Thr Gly Arg Asp Ile Thr Tyr Tyr Ala Ser Trp Ala Lys
     50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Asp Gly Gly Ser Ser Ala Ile Thr Ser Asn Asn Ile Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285
```

```
Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Ala Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly
```

```
<210> SEQ ID NO 56
<211> LENGTH: 120
<212> TYPE: PRT
<213> ORGANISM: Artificial Sequence
<220> FEATURE:
<223> OTHER INFORMATION: synthesized

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Thr Asn
            20                  25                  30

Ala Met Ser Trp Val Arg Gln Ala Pro Gly Lys Gly Leu Glu Trp Ile
        35                  40                  45

Gly Val Ile Thr Gly Arg Asp Ile Thr Tyr Tyr Ala Ser Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Gly Gly Ser Ser Ala Ile Thr Ser Asn Asn Ile Trp Gly Gln
            100                 105                 110

Gly Thr Leu Val Thr Val Ser Ser
        115                 120
```

```
<210> SEQ ID NO 57
<211> LENGTH: 657
<212> TYPE: DNA
<213> ORGANISM: Artificial Sequence
<220> FEATURE:
<223> OTHER INFORMATION: synthesized

<400> SEQUENCE: 57
gacatccaga tgacccagtc tccttccacc ctgtctgcat ctgtaggaga cagagtcacc        60
atcacttgcc aagccagtga gagcattagc agttggttag cctggtatca gcagaaacca       120
```

```
gggaaagccc ctaagctcct gatctatgaa gcatccaaac tggcatctgg ggtcccatca      180
aggttcagcg gcagtggatc tgggacagaa ttcactctca ccatcagcag cctgcagcct      240
gatgattttg caacttatta ctgccaaggc tatttttatt ttattagtcg tagttatgta      300
aatgctttcg gcggagggac caaggtggag atcaaacgta cggtggctgc accatctgtc      360
ttcatcttcc cgccatctga tgagcagttg aaatctggaa ctgcctctgt tgtgtgcctg      420
ctgaataact tctatcccag agaggccaaa gtacagtgga aggtggataa cgccctccaa      480
tcgggtaact cccaggagag tgtcacagag caggacagca aggacagcac ctacagcctc      540
agcagcaccc tgacgctgag caaagcagac tacgagaaac acaaagtcta cgcctgcgaa      600
gtcacccatc agggcctgag ctcgcccgtc acaaagagct tcaacagggg agagtgt       657
```

```
<210> SEQ ID NO 58
<211> LENGTH: 336
<212> TYPE: DNA
<213> ORGANISM: Artificial Sequence
<220> FEATURE:
<223> OTHER INFORMATION: synthesized

<400> SEQUENCE: 58
gacatccaga tgacccagtc tccttccacc ctgtctgcat ctgtaggaga cagagtcacc       60
atcacttgcc aagccagtga gagcattagc agttggttag cctggtatca gcagaaacca      120
gggaaagccc ctaagctcct gatctatgaa gcatccaaac tggcatctgg ggtcccatca      180
aggttcagcg gcagtggatc tgggacagaa ttcactctca ccatcagcag cctgcagcct      240
gatgattttg caacttatta ctgccaaggc tatttttatt ttattagtcg tagttatgta      300
aatgctttcg gcgagggac caaggtggag atcaaa                                 336
```

```
<210> SEQ ID NO 59
<211> LENGTH: 219
<212> TYPE: PRT
<213> ORGANISM: Artificial Sequence
<220> FEATURE:
<223> OTHER INFORMATION: synthesized

<400> SEQUENCE: 59

Asp Ile Gln Met Thr Gln Ser Pro Ser Thr Leu Ser Ala Ser Val Gly
1               5                   10                  15

Asp Arg Val Thr Ile Thr Cys Gln Ala Ser Glu Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Lys Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gly Tyr Phe Tyr Phe Ile Ser
                85                  90                  95

Arg Ser Tyr Val Asn Ala Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140
```

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 60
<211> LENGTH: 112
<212> TYPE: PRT
<213> ORGANISM: Artificial Sequence
<220> FEATURE:
<223> OTHER INFORMATION: synthesized

<400> SEQUENCE: 60

Asp Ile Gln Met Thr Gln Ser Pro Ser Thr Leu Ser Ala Ser Val Gly
1               5                   10                  15

Asp Arg Val Thr Ile Thr Cys Gln Ala Ser Glu Ser Ile Ser Ser Trp
            20                  25                  30

Leu Ala Trp Tyr Gln Lys Pro Gly Lys Ala Pro Lys Leu Leu Ile
        35                  40                  45

Tyr Glu Ala Ser Lys Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gly Tyr Phe Tyr Phe Ile Ser
                85                  90                  95

Arg Ser Tyr Val Asn Ala Phe Gly Gly Gly Thr Lys Val Glu Ile Lys
            100                 105                 110

<210> SEQ ID NO 61
<211> LENGTH: 1347
<212> TYPE: DNA
<213> ORGANISM: Artificial Sequence
<220> FEATURE:
<223> OTHER INFORMATION: synthesized

<400> SEQUENCE: 61
gaggtgcagc tggtggagtc tgggggaggc ttggtccagc ctggggggtc cctgagactc      60
tcctgtgcag cctctggatt caccatcagt agcaatgcaa tgagctgggt ccgccaggct     120
ccagggaagg ggctggagtg gatcggagtc attactggtc gtgatatcac atactacgcg     180
aactgggcga aggcagatt caccatctcc agagacaatt ccaagaacac gctgtatctt     240
caaatgaaca gcctgagagc cgaggacacg gctgtgtatt actgtgcgag agacggtggt     300
tcttctgcta ttactagtaa caacatttgg ggccagggaa ccctggtcac cgtctcgagc     360
gctagcacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagag agttgagccc     660

| | |
|---|---|
| aaatcttgtg acaaaactca cacatgccca ccgtgcccag cacctgaagc cgcgggggca | 720 |
| ccgtcagtct tcctcttccc cccaaaaccc aaggacaccc tcatgatctc ccggaccct | 780 |
| gaggtcacat gcgtggtggt ggacgtgagc cacgaagacc ctgaggtcaa gttcaactgg | 840 |
| tacgtggacg gcgtggaggt gcataatgcc aagacaaagc cgcgggagga gcagtacaac | 900 |
| agcacgtacc gtgtggtcag cgtcctcacc gtcctgcacc aggactggct gaatggcaag | 960 |
| gagtacaagt gcgcggtctc caacaaagcc ctcccagccc ccatcgagaa aaccatctcc | 1020 |
| aaagccaaag gcagccccg agaaccacag gtgtacaccc tgcccccatc ccgggatgag | 1080 |
| ctgaccaaga accaggtcag cctgacctgc ctggtcaaag gcttctatcc cagcgacatc | 1140 |
| gccgtggagt gggagagcaa tgggcagccg gagaacaact acaagaccac gcctcccgtg | 1200 |
| ctggactccg acggctcctt cttcctctat agcaagctca ccgtggacaa gagcaggtgg | 1260 |
| cagcagggga acgtcttctc atgctccgtg atgcatgagg ctctgcacaa ccactacacg | 1320 |
| cagaagagcc tctccctgtc tccgggt | 1347 |

<210> SEQ ID NO 62
<211> LENGTH: 360
<212> TYPE: DNA
<213> ORGANISM: Artificial Sequence
<220> FEATURE:
<223> OTHER INFORMATION: synthesized

<400> SEQUENCE: 62

| | |
|---|---|
| gaggtgcagc tggtggagtc tgggggaggc ttggtccagc ctgggggtc cctgagactc | 60 |
| tcctgtgcag cctctggatt caccatcagt agcaatgcaa tgagctgggt ccgccaggct | 120 |
| ccagggaagg gctggagtg gatcggagtc attactggtc gtgatatcac atactacgcg | 180 |
| aactgggcga aaggcagatt caccatctcc agagacaatt ccaagaacac gctgtatctt | 240 |
| caaatgaaca gcctgagagc cgaggacacg gctgtgtatt actgtgcgag agacggtggt | 300 |
| tcttctgcta ttactagtaa caacatttgg ggccagggaa ccctggtcac cgtctcgagc | 360 |

<210> SEQ ID NO 63
<211> LENGTH: 449
<212> TYPE: PRT
<213> ORGANISM: Artificial Sequence
<220> FEATURE:
<223> OTHER INFORMATION: synthesized

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Ser Asn
            20                  25                  30

Ala Met Ser Trp Val Arg Gln Ala Pro Gly Lys Gly Leu Glu Trp Ile
        35                  40                  45

Gly Val Ile Thr Gly Arg Asp Ile Thr Tyr Tyr Ala Asn Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Gly Gly Ser Ser Ala Ile Thr Ser Asn Asn Ile Trp Gly Gln
            100                 105                 110

Gly Thr Leu Val Thr Val Ser Ser Ala Ser Thr Lys Gly Pro Ser Val
        115                 120                 125

```
Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Ala Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 64
<211> LENGTH: 120
<212> TYPE: PRT
<213> ORGANISM: Artificial Sequence
<220> FEATURE:
<223> OTHER INFORMATION: synthesized

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Ser Asn
            20                  25                  30
```

Ala Met Ser Trp Val Arg Gln Ala Pro Gly Lys Gly Leu Glu Trp Ile
            35                  40                  45

Gly Val Ile Thr Gly Arg Asp Ile Thr Tyr Tyr Ala Asn Trp Ala Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
             85                  90                  95

Arg Asp Gly Gly Ser Ser Ala Ile Thr Ser Asn Asn Ile Trp Gly Gln
            100                 105                 110

Gly Thr Leu Val Thr Val Ser Ser
            115                 120

<210> SEQ ID NO 65
<211> LENGTH: 657
<212> TYPE: DNA
<213> ORGANISM: Artificial Sequence
<220> FEATURE:
<223> OTHER INFORMATION: synthesized

<400> SEQUENCE: 65
gacatccaga tgacccagtc tccttccacc ctgtctgcat ctgtaggaga cagagtcacc     60
atcacttgcc aagccagtga gagcattagc agttggttag cctggtatca gcagaaacca    120
gggaaagccc ctaagctcct gatctatgaa gcatccaaac tggcatctgg ggtcccatca    180
aggttcagcg gcagtggatc tgggacagaa ttcactctca ccatcagcag cctgcagcct    240
gatgattttg caacttatta ctgccaaggc tatttttatt ttattagtcg tacttatgta    300
aatgctttcg gcggagggac caaggtggag atcaaacgta cggtggctgc accatctgtc    360
ttcatcttcc cgccatctga tgagcagttg aaatctggaa ctgcctctgt tgtgtgcctg    420
ctgaataact ctatcccag agaggccaaa gtacagtgga aggtggataa cgccctccaa     480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgt       657

<210> SEQ ID NO 66
<211> LENGTH: 336
<212> TYPE: DNA
<213> ORGANISM: Artificial Sequence
<220> FEATURE:
<223> OTHER INFORMATION: synthesized

<400> SEQUENCE: 66
gacatccaga tgacccagtc tccttccacc ctgtctgcat ctgtaggaga cagagtcacc     60
atcacttgcc aagccagtga gagcattagc agttggttag cctggtatca gcagaaacca    120
gggaaagccc ctaagctcct gatctatgaa gcatccaaac tggcatctgg ggtcccatca    180
aggttcagcg gcagtggatc tgggacagaa ttcactctca ccatcagcag cctgcagcct    240
gatgattttg caacttatta ctgccaaggc tatttttatt ttattagtcg tacttatgta    300
aatgctttcg gcggagggac caaggtggag atcaaa                              336

<210> SEQ ID NO 67
<211> LENGTH: 219
<212> TYPE: PRT
<213> ORGANISM: Artificial Sequence
<220> FEATURE:
<223> OTHER INFORMATION: synthesized

<400> SEQUENCE: 67

Asp Ile Gln Met Thr Gln Ser Pro Ser Thr Leu Ser Ala Ser Val Gly
1               5                   10                  15

Asp Arg Val Thr Ile Thr Cys Gln Ala Ser Glu Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Lys Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gly Tyr Phe Tyr Phe Ile Ser
                85                  90                  95

Arg Thr Tyr Val Asn Ala Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 68
<211> LENGTH: 112
<212> TYPE: PRT
<213> ORGANISM: Artificial Sequence
<220> FEATURE:
<223> OTHER INFORMATION: synthesized

<400> SEQUENCE: 68

Asp Ile Gln Met Thr Gln Ser Pro Ser Thr Leu Ser Ala Ser Val Gly
1               5                   10                  15

Asp Arg Val Thr Ile Thr Cys Gln Ala Ser Glu Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Lys Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gly Tyr Phe Tyr Phe Ile Ser
                85                  90                  95

Arg Thr Tyr Val Asn Ala Phe Gly Gly Gly Thr Lys Val Glu Ile Lys
            100                 105                 110

<210> SEQ ID NO 69
<211> LENGTH: 1347

<212> TYPE: DNA
<213> ORGANISM: Artificial Sequence
<220> FEATURE:
<223> OTHER INFORMATION: synthesized

<400> SEQUENCE: 69

```
gaggtgcagc tggtggagtc tgggggaggc ttggtccagc ctgggggtc cctgagactc      60
tcctgtgcag cctctggaat cgacctcagt agcaatgcaa tgagctgggt ccgccaggct    120
ccagggaagg ggctggagtg gatcggagtc attactggtc gtgatatcac atactacgcg    180
agctgggcga aaggcagatt caccatctcc agagacaatt ccaagaacac gctgtatctt    240
caaatgaaca gcctgagagc cgaggacacg gctgtgtatt actgtgcgag agacggtggt    300
tcttctgcta ttaatagtaa gaacatttgg ggccagggaa ccctggtcac cgtctcgagc    360
gctagcacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagag agttgagccc    660
aaatcttgtg acaaaactca cacatgccca ccgtgcccag cacctgaagc cgcggggca    720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcgcggtctc caacaaagcc ctcccagccc ccatcgagaa aaccatctcc   1020
aaagccaaag ggcagccccg agaaccacag gtgtacaccc tgcccccatc ccgggatgag   1080
ctgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctat agcaagctca ccgtggacaa gagcaggtgg   1260
cagcagggga acgtcttctc atgctccgtg atgcatgagg ctctgcacaa ccactacacg   1320
cagaagagcc tctccctgtc tccgggt                                        1347
```

<210> SEQ ID NO 70
<211> LENGTH: 360
<212> TYPE: DNA
<213> ORGANISM: Artificial Sequence
<220> FEATURE:
<223> OTHER INFORMATION: synthesized

<400> SEQUENCE: 70

```
gaggtgcagc tggtggagtc tgggggaggc ttggtccagc ctgggggtc cctgagactc      60
tcctgtgcag cctctggaat cgacctcagt agcaatgcaa tgagctgggt ccgccaggct    120
ccagggaagg ggctggagtg gatcggagtc attactggtc gtgatatcac atactacgcg    180
agctgggcga aaggcagatt caccatctcc agagacaatt ccaagaacac gctgtatctt    240
caaatgaaca gcctgagagc cgaggacacg gctgtgtatt actgtgcgag agacggtggt    300
tcttctgcta ttaatagtaa gaacatttgg ggccagggaa ccctggtcac cgtctcgagc    360
```

<210> SEQ ID NO 71
<211> LENGTH: 449
<212> TYPE: PRT

<213> ORGANISM: Artificial Sequence
<220> FEATURE:
<223> OTHER INFORMATION: synthesized

<400> SEQUENCE: 71

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Leu Ser Ser Asn
            20                  25                  30

Ala Met Ser Trp Val Arg Gln Ala Pro Gly Lys Gly Leu Glu Trp Ile
        35                  40                  45

Gly Val Ile Thr Gly Arg Asp Ile Thr Tyr Tyr Ala Ser Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Gly Gly Ser Ser Ala Ile Asn Ser Lys Asn Ile Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Ala Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380
```

-continued

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
            435                 440                 445

Gly

<210> SEQ ID NO 72
<211> LENGTH: 120
<212> TYPE: PRT
<213> ORGANISM: Artificial Sequence
<220> FEATURE:
<223> OTHER INFORMATION: synthesized

<400> SEQUENCE: 72

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Leu Ser Ser Asn
            20                  25                  30

Ala Met Ser Trp Val Arg Gln Ala Pro Gly Lys Gly Leu Glu Trp Ile
        35                  40                  45

Gly Val Ile Thr Gly Arg Asp Ile Thr Tyr Tyr Ala Ser Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Asp Gly Gly Ser Ser Ala Ile Asn Ser Lys Asn Ile Trp Gly Gln
        100                 105                 110

Gly Thr Leu Val Thr Val Ser Ser
        115                 120

<210> SEQ ID NO 73
<211> LENGTH: 5
<212> TYPE: PRT
<213> ORGANISM: Artificial Sequence
<220> FEATURE:
<223> OTHER INFORMATION: Synthesized

<400> SEQUENCE: 73

Thr Asn Ala Met Ser
1               5

<210> SEQ ID NO 74
<211> LENGTH: 16
<212> TYPE: PRT
<213> ORGANISM: Artificial Sequence
<220> FEATURE:
<223> OTHER INFORMATION: Synthesized

<400> SEQUENCE: 74

Val Ile Thr Gly Arg Asp Ile Thr Tyr Tyr Ala Ser Trp Ala Lys Gly
1               5                   10                  15

<210> SEQ ID NO 75
<211> LENGTH: 12
<212> TYPE: PRT

```
<213> ORGANISM: Artificial Sequence
<220> FEATURE:
<223> OTHER INFORMATION: Synthesized

<400> SEQUENCE: 75

Asp Gly Gly Ser Ser Ala Ile Thr Ser Asn Asn Ile
1               5                   10

<210> SEQ ID NO 76
<211> LENGTH: 11
<212> TYPE: PRT
<213> ORGANISM: Artificial Sequence
<220> FEATURE:
<223> OTHER INFORMATION: Synthesized

<400> SEQUENCE: 76

Gln Ala Ser Glu Ser Ile Ser Ser Trp Leu Ala
1               5                   10

<210> SEQ ID NO 77
<211> LENGTH: 7
<212> TYPE: PRT
<213> ORGANISM: Artificial Sequence
<220> FEATURE:
<223> OTHER INFORMATION: Synthesized

<400> SEQUENCE: 77

Glu Ala Ser Lys Leu Ala Ser
1               5

<210> SEQ ID NO 78
<211> LENGTH: 14
<212> TYPE: PRT
<213> ORGANISM: Artificial Sequence
<220> FEATURE:
<223> OTHER INFORMATION: Synthesized

<400> SEQUENCE: 78

Gln Gly Tyr Phe Tyr Phe Ile Ser Arg Thr Tyr Val Asn Ser
1               5                   10
```

ANTI-CD3 ANTIBODIES AND METHODS OF MAKING AND USING THEREOF

CROSS-REFERENCE TO RELATED APPLICATIONS

This application claims the benefit of U.S. Provisional Patent Application No. 62/551,032 filed 27 Aug. 2017, the entire disclosure of which is expressly incorporated herein by reference in its entirety.

TECHNICAL FIELD

The present disclosure generally relates to the technical field of antibodies, and more particularly relates to making and using anti-CD3 antibodies.

BACKGROUND

Cancer is a major health problem across the world. In the United States alone it is estimated that in 2016 there were 1,685,210 new cases of cancer diagnosed and 595,690 deaths from the disease (http://www.cancer.gov). As such, any pharmaceutical agent that can reduce the severity or mortality rate from cancer is desirable.

In the immune system, resting T-cells can be activated to respond to antigen through a primary signal delivered through the T-cell receptor (TCR) by foreign antigen peptides presented by antigen-presenting cells (APCs). In addition to this primary signal, there are secondary positive and negative co-stimulatory signals that further influence the response of the T-cells. A secondary positive signal is required for full T-cell activation ((Lafferty et al., Ausl. J. Exp. Biol. Med. Sci. 53: 27-42 (1975)). Negative secondary signals can result in T-cell suppression and tolerance.

The Cluster of Differentiation 3 (CD3) T-cell co-receptor helps to activate both the cytotoxic T-Cell (CD8+ naive T cells) and also T helper cells (CD4+naive T cells). It consists of a protein complex and is composed of four distinct chains. In mammals, the complex contains a CD3γ chain, a CD3δ chain, and two CD3ε chains. These chains associate with a molecule known as the T-cell receptor (TCR) and the ζ-chain (zeta-chain) to generate an activation signal in T lymphocytes. The TCR, ζ-chain, and CD3 molecules together constitute the TCR complex.

Because CD3 is required for T-cell activation, monoclonal antibodies (mAbs) that target it are being investigated as immunosuppressant therapies (e.g., otelixizumab, foralumab) for type 1 diabetes and other autoimmune diseases. However, it remains unclear whether specific anti-CD3 mAbs can active CD3+ T cells, thus to increase the host immune response to cancerous tumours.

SUMMARY

The present disclosure provides, among others, anti-CD3 monoclonal antibodies, antigen-binding portions thereof, therapeutic compositions thereof and/or nucleic acid encoding the same, and their use to activate CD3+ T-cells and thus to enhance cell-mediated immune responses in the treatment of cancer and other T-cell dysfunctional disorders.

In one embodiment, an isolated monoclonal antibody (mAb) or antigen-binding fragment thereof that binds specifically to human CD3 is provided.

In one embodiment, the isolated mAb or antigen-binding fragment comprises an amino acid sequence having a percentage homology with SEQ ID NO:4, SEQ ID NO:8, SEQ ID NO:12, SEQ ID NO:16, SEQ ID NO:20, SEQ ID NO:24, SEQ ID NO:28, SEQ ID NO:32, SEQ ID NO:36, SEQ ID NO:40, SEQ ID NO:44, SEQ ID NO:48, SEQ ID NO:52, SEQ ID NO:56, SEQ ID NO:60, SEQ ID NO:64, SEQ ID NO:68, or SEQ ID NO:72. In one embodiment, the percentage homology is not less than 70%, 75%, 80%, 90%, 95%, 98%, or 99%.

In one embodiment, the isolated mAb or antigen-binding fragment has a binding affinity to CD3 with a Kd not greater than 30 nM, 40 nM or 50 nM. In one embodiment, the isolated mAb or antigen-binding fragment has a binding affinity to CD3 with a Kd not greater than 60 nM. In one embodiment, the isolated mAb or antigen-binding fragment has a binding affinity to CD3 with a Kd not greater than 70 nM. In one embodiment, the isolated mAb or antigen-binding fragment has a binding affinity to CD3 with a Kd not greater than 80 nM. In one embodiment, the isolated mAb or antigen-binding fragment has a binding affinity to CD3 with a Kd not greater than 100 nM.

In some embodiments, the isolated mAb or antigen-binding fragment may exhibit one or more functional properties including, for example, high affinity binding to CD3, enhancing T cell activation, stimulating antibody response, reversing the suppressive function of an immunosuppressive cell, or a combination thereof. In one embodiment, the isolated mAb or antigen-binding fragment may enhance T-cell activation via T-cell proliferation, IFN-γ and/or IL-2 secretion, or a combination thereof. In one embodiment, the isolated mAb or antigen-binding fragment may reverse the suppressive function of a T regulatory cell.

In some embodiments, the isolated mAb or antigen-binding fragment may include a human framework region. In one embodiment, the isolated mAb or antigen-binding fragment may include a humanized antibody, a chimeric antibody, or a recombinant antibody.

In one embodiment, the isolated mAb or antigen-binding fragment may be an antibody belonging to IgG family. In one embodiment, the isolated mAb is an IgG. In one embodiment, the isolated mAb or antigen-binding fragment may include an antigen-binding fragment including, for example, a Fv, a Fab, a F(ab')2, a scFV or a scFV2 fragment.

In one embodiment, the isolated mAb or antigen-binding fragment may be a bispecific antibody, tri-specific antibody, or multi-specific antibody.

In one embodiment, the isolated mAb or antigen-binding fragment may include an IgG1 heavy chain that comprises an amino acid sequence having a percentage homology with SEQ ID NO:7, SEQ ID NO:15, SEQ ID NO:23, SEQ ID NO:31, SEQ ID NO:39, SEQ ID NO:47, SEQ ID NO:55, SEQ ID NO:63, or SEQ ID NO:71. In one embodiment, the percentage homology is not less than 70%, 75%, 80%, 90%, 95%, 98%, or 99%.

In one embodiment, the isolated mAb or antigen-binding fragment may include a kappa light chain that comprises an amino acid sequence having a percentage homology with SEQ ID NO:3, SEQ ID NO:11, SEQ ID NO:19, SEQ ID NO:27, SEQ ID NO:35, SEQ ID NO:43, SEQ ID NO:51, SEQ ID NO:59, or SEQ ID NO:67. In one embodiment, the percentage homology is not less than 70%, 75%, 80%, 90%, 95%, 98%, or 99%.

In one embodiment, the isolated mAb or antigen-binding fragment may include a variable light chain that comprises an amino acid sequence having at least 70%, 80%, 90%, 95%, 98% or 99% identity with SEQ ID NO:4, SEQ ID NO:12, SEQ ID NO:20, SEQ ID NO:28, SEQ ID NO:36, SEQ ID NO:44, SEQ ID NO:52, SEQ ID NO:60, or SEQ ID NO: 68.

In one embodiment, the isolated mAb or antigen-binding fragment may include a variable heavy chain that comprises an amino acid sequence having a percentage homology with SEQ ID NO:8, SEQ ID NO:16, SEQ ID NO:24, SEQ ID NO:32, SEQ ID NO:40, SEQ ID NO:48, SEQ ID NO:56, SEQ ID NO:64, or SEQ ID NO:72. In one embodiment, the percentage homology is not less than 70%, 75%, 80%, 90%, 95%, 98%, or 99%.

The application further provides the nucleic acid sequences encoding the amino acid sequences, isolated mAbs or antigen-binding fragments disclosed herein. In one embodiment, the isolated nucleic acids encoding an IgG1 heavy chain having a percentage homology with SEQ ID NO:5, SEQ ID NO:13, SEQ ID NO:21, SEQ ID NO:29, SEQ ID NO:37, SEQ ID NO:45, SEQ ID NO:53, SEQ ID NO:61, or SEQ ID NO:69; the kappa light chain comprising SEQ ID NO:1, SEQ ID NO:9, SEQ ID NO:17, SEQ ID NO:25, SEQ ID NO:33, SEQ ID NO:41, SEQ ID NO:49, SEQ ID NO:57, or SEQ ID NO:65. In one embodiment, the isolated nucleic acids encoding an variable light chain having a percentage homology with SEQ ID NO:2, SEQ ID NO:10, SEQ ID NO:18, SEQ ID NO:26, SEQ ID NO:34, SEQ ID NO:42, SEQ ID NO:50, SEQ ID NO:58, or SEQ ID NO:66. In one embodiment, the isolated nucleic acids encoding a variable heavy chain having a percentage homology with SEQ ID NO:6, SEQ ID NO:14, SEQ ID NO:22, SEQ ID NO:30, SEQ ID NO:38, SEQ ID NO:46, SEQ ID NO:54, SEQ ID NO:62, or SEQ ID NO:70. In one embodiment, the percentage homology is not less than 70%, 75%, 80%, 90%, 95%, 98%, or 99%.

The application further provides expression vectors containing the nucleic acid sequences disclosed herein. In one embodiment, the vector is expressible in a cell. In one embodiment, an expression vector encoding an isolated mAb or antigen-binding fragment as disclosed herein.

In one embodiment, the expression vector described herein may be present in a cell and expressible. In one embodiment, the expression vector described herein may be present in a host cell and expressible. In one embodiment, host cells comprising the expression vector are provided, wherein the expression vector comprises a nucleic acid disclosed herein. The host cell can be a prokaryotic cell or a eukaryotic cell.

Methods of producing an antibody as disclosed herein are provided. In one embodiment, the method includes the steps of providing a host that contains an expression vector expressible in the host cell, the expression vector comprises a nucleic acid sequence disclosed herein, to produce an antibody by the expression of the nucleic acid sequence.

The application further provides immunoconjugates. In one embodiment, the immunoconjudates include the isolated mAb or an antigen-binding fragment thereof conjugated to a drug unit. In some embodiments, the drug unit is linked to the isolated mAb or an antigen-binding fragment through a linker.

The linker may be a conjugated bond. The linker may be cleavable or noncleavable. In one embodiment, the linker is a chemical linker. In one embodiment, the linker comprises a covalent bond such an ester bond, an ether bond, an amine bond, an amide bond, a disulphide bond, an imide bond, a sulfone bond, a phosphate bond, a phosphorus ester bond, a peptide bond, a hydrazone bond or a combination thereof. In one embodiment, the linker comprises a hydrophobic poly (ethylene glycol) linker. In one embodiment, the linker comprises a peptide bond.

In one embodiment, an immunoconjugate is provided that comprises a drug unit and an isolated mAb or antigen-binding fragment that binds specifically to human CD3. In one embodiment, the drug unit in the immunoconjugate may be a chemotherapeutic agent, a growth inhibitory agent, a toxin, or a radioactive isotope. In one embodiment, the drug unit may be a drug unit from class of calicheamicin, an antimitotic agent, a toxin, or a radioactive isotope. In one embodiment, the drug unit comprises a drug unit from class of calicheamicins. Examples of calicheamicins include ozogamicin. In one embodiment, the drug unit comprises an antimitotic agent. Example antimiotic agent includes monomethyl auristatin E. In one embodiment, the drug unit comprises emtansine (DM1).

In one embodiment, the drug unit is selected from a cytotoxic agent, an immune regulatory reagent, an imaging agent or a combination thereof. In one embodiment, the cytotoxic agent is selected from a growth inhibitory agent or a chemotherapeutic agent from a class of tubulin binders, DNA intercalators, DNA alkylators, enzyme inhibitors, immune modulators, antimetabolite agents, radioactive isotopes, or a combination thereof. In one embodiment, the cytotoxic agent is selected from a calicheamicin, ozogamicin, monomethyl auristatin E, emtansine, a derivative or a combination thereof. In one embodiment, the immune regulatory reagents activate or suppress immune cells, T cell, NK cell, B cell, macrophage, or dendritic cell.

In one embodiment, the imaging agent may be radionuclide, a florescent agent, a quantum dots, or a combination thereof.

The application further provides pharmaceutical compositions. In one embodiment, the pharmaceutical composition may include an isolated mAb or antigen-binding fragment disclosed herein and a pharmaceutically acceptable carrier. In one embodiment, the pharmaceutical composition may include an immunoconjugate disclosed herein and a pharmaceutically acceptable carrier.

In one embodiment, the pharmaceutical composition further comprises radioisotope, radionuclide, a toxin, a therapeutic agent, a chemotherapeutic agent, a drug unit from class of calicheamicin, an antimitotic agent, a radioactive isotope, a therapeutic agent, or a combination thereof. In one embodiment, the therapeutic agent may include an antibody, an enzyme, a chemotherapeutic agent, a growth inhibitory agent, or a combination thereof.

The application further provides methods for treating a subject with a cancer. In one embodiment, the method includes the steps of administering to the subject an effective amount of the isolated mAb or antigen-binding fragment disclosed herein. In one embodiment, the isolated mAb or antigen-binding fragment binds specifically to human CD3.

In one embodiment, the method of treating a subject with a cancer may include co-administering a therapeutic agent together with an effective amount of the isolated mAb or antigen-binding fragment having binding specificity to human CD3. In some embodiments, the therapeutic agent may be an antibody, a chemotherapy agent, an enzyme, or a combination thereof. In some embodiments, the therapeutic agent may be capecitabine, cisplatin, trastuzumab, fulvestrant, tamoxifen, letrozole, exemestane, anastrozole, aminoglutethimide, testolactone, vorozole, formestane, fadrozole, letrozole, erlotinib, lafatinib, dasatinib, gefitinib, imatinib, pazopinib, lapatinib, sunitinib, nilotinib, sorafenib, nab-palitaxel, ozogamicin, monomethyl auristatin E, emtansine (DM1), a derivative or a combination thereof.

Varieties of cancers may be treated using disclosed compositions, isolated mAbs or antigen-binding fragments. In one embodiment, the cancer may include cells that express CD3. Example cancers that may be treated including, without limitation, breast cancer, colorectal cancer, pancreatic cancer, head and neck cancer, melanoma, ovarian cancer, prostate cancer, non-small lung cell cancer, glioma, esophageal cancer, nasopharyngeal cancer, anal cancer, rectal cancer, gastric cancer, bladder cancer, cervical cancer, or brain cancer.

The subject receiving treatment may be a human. The application further provides a solution that includes an effective concentration of the isolated mAb or an antigen-binding fragment that binds specifically to human CD3. In one embodiment, the solution is blood plasma in a subject.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments arranged in accordance with the disclosure and are, therefore, not to be considered limiting of its scope, the disclosure will be described with additional specificity and detail through use of the accompanying drawings, in which:

FIG. 1 shows the immunization strategy of NZW rabbits with human or cynomolgus CD3;

FIG. 3 provides a summary of screening BCC supernatants for rabbit IgG binding human and cynomolgus T cells by FACS and activation of human CD3+ T cells;

FIG. 4 shows the binding of example chimeric rabbit/human IgG antibodies to Cynomolgus CD3 Delta, Gamma, or Epsilon Fc fusion proteins and human T cell line Jurkat;

FIG. 7 shows the activation of human CD3+ T cells by example chimeric rabbit/human CD3-specific antibodies; and FIG. 8 shows the binding and off-rate analysis of example chimeric rabbit/human or humanized CD3-specific antibodies.

DETAILED DESCRIPTION

Figure 2C:
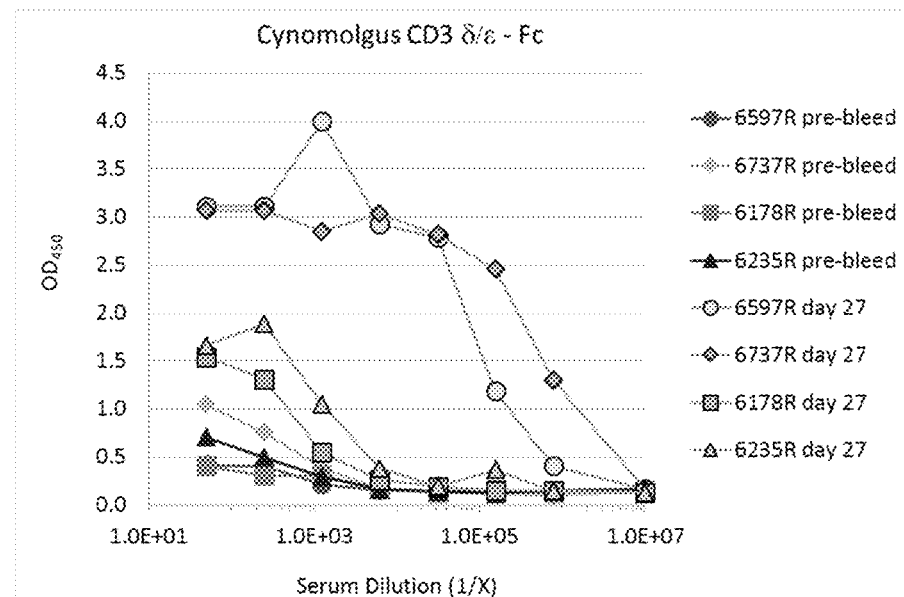
FIG. 2 shows the analysis of rabbit serum for example human and cynomolgus CD3 gamma/epsilon or delta-epsilon Fc-specific IgG before and after immunization.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The application provides, among others, isolated antibodies, methods of making such antibodies, bispecific or multi-specific molecules, antibody-drug conjugates and/or immunoconjugates composed from such antibodies or antigen-binding fragments and pharmaceutical compositions containing the antibodies, bispecific or multi-specific molecules, antibody-drug conjugates and/or immunoconjugates, and methods of using such antibodies, conjugates, or compositions for treating a cancer.

In one aspect, application provides isolated monoclonal antibodies or a fragment thereof that bind to human CD3. The antibodies or a fragment thereof may exhibit one or more desirable functional properties, including without limitation high affinity binding to CD3, the ability to bind to human T cell line Jurkat, the ability to enhance human CD3+ T cell activation including proliferation, IFN-γ and/or IL-2 secretion, the ability to stimulate antibody responses and/or the ability to reverse the suppressive function of immunosuppressive cells, such as T regulatory cells. The antibodies or a fragment thereof may be derived from specific heavy and light chain amino acid sequences and/or structural features such as complementarity determining regions (CDRs) composed of specific amino acid sequences as disclosed herein.

In some embodiments, the antibodies were created by the immunization of rabbits with Human CD3 Delta-Epsilon Fc ("Knobs-into-hole"—KnH) and Gamma-Epsilon Fc (KnH) fusion proteins or HEK 293 cells transiently transfected with human or cynomolgus "CD3 complex" (alpha and beta T cell receptor, gamma, delta, and epsilon accessory chains). Rabbits are known to create antibodies of high affinity, diversity and specificity (Weber et al. Exp. Mol. Med. 49:e305, which is incorporated herein by reference in its entirety). B cells from immunized animals were cultured in vitro and screened for the production of anti-CD3 antibodies. The antibody variable genes were isolated using recombinant DNA techniques and the resulting antibodies were expressed recombinantly and further screened for desired features such as the ability to bind to human and Cynomolgus CD3 Delta, Gamma, or Epsilon Fc fusion proteins, to bind to human T cell line Jurkat and Cynomolgus T cell line HSC-F, and the ability to active purified human CD3+ T cells. This general method of antibody discovery is similar to that described in Seeber et al. PLOS One. 9:e86184 (2014), which is incorporated herein by reference in its entirety.

The term "antibody" is used in the broadest sense and specifically covers single monoclonal antibodies (including agonist and antagonist antibodies), antibody compositions with polyepitopic specificity, as well as antibody fragments (e.g., Fab, F(ab')$_2$, and Fv), so long as they exhibit the desired biological activity. In some embodiments, the antibody may be monoclonal, polyclonal, chimeric, single chain, bispecific or bi-effective, and humanized antibodies, as well as active fragments thereof. Examples of active fragments of molecules that bind to known antigens include Fab, F(ab')$_2$, scFv and Fv fragments, as well as the products of a Fab immunoglobulin expression library and epitope-binding fragments of any of the antibodies and fragments mentioned above. In some embodiments, antibody may include immunoglobulin molecules and immunologically active portions of immunoglobulin molecules, i.e. molecules that contain a binding site with an immunologic binding specificity to an antigen. The immunoglobulin can be of any type (IgG, IgM, IgD, IgE, IgA and IgY) or class (IgG1, IgG2, IgG3, IgG4, IgA1 and IgA2) or subclasses of immunoglobulin molecule. In one embodiment, the antibody may be a whole antibody and any antigen-binding fragment derived from the whole antibody. A typical antibody refers to heterotetrameric protein comprising typically of two heavy (H) chains and two light (L) chains. Each heavy chain is comprised of a heavy chain variable domain (abbreviated as VH) and a heavy chain constant domain. Each light chain is comprised of a light chain variable domain (abbreviated as VL) and a light chain constant domain. The VH and VL regions can be further subdivided into domains of hypervariable complementarity determining regions (CDR), and more conserved regions called framework regions (FR). Each variable domain (either VH or VL) is typically composed of three CDRs and four FRs, arranged in the following order: FR1, CDR1, FR2, CDR2, FR3, CDR3, FR4 from amino-terminus to carboxy-terminus. Within the variable regions of the light and heavy chains there are binding regions that interacts with the antigen.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant (epitope) on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler & Milstein, *Nature,* 256:495 (1975), which is incorporated herein by reference in its entirety, or may be made by recombinant DNA methods (see, e.g., U.S. Pat. No. 4,816, 567, which is incorporated herein by reference in its entirety).

Monoclonal antibodies can be produced using various methods including mouse hybridoma or phage display (see Siegel. Transfus. Clin. Biol. 9:15-22 (2002), which is incorporated herein by reference in its entirety) or from molecular cloning of antibodies directly from primary B cells (see Tiller. New Biotechnol. 28:453-7 (2011), which is incorporated herein by reference in its entirety).

In some embodiments, the monoclonal antibodies may include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567 (Cabilly et al.); and Morrison et al., *Proc. Natl. Acad. Sci. USA,* 81:6851-6855 [1984]).

The term "antigen- or epitope-binding portion or fragment" refers to fragments of an antibody that are capable of binding to an antigen (for example, CD3). These fragments may be capable of the antigen-binding function and additional functions of the intact antibody. Examples of binding fragments include, but are not limited to, a single-chain Fv fragment (scFv) consisting of the VL and VH domains of a single arm of an antibody connected in a single polypeptide chain by a synthetic linker, or a Fab fragment that is a monovalent fragment consisting of the VL, constant light (CL), VH and constant heavy 1 (CH1) domains. Antibody fragments can be even smaller sub-fragments and can consist of domains as small as a single CDR domain. In one embodiment, the single CDR domain may be the CDR3 regions from either the VL and/or VH domains (for example, see Beiboer et al., J. Mol. Biol. 296:833-49 (2000), which is incorporated herein by reference in its entirety). Antibody fragments are produced using conventional methods known to those skilled in the art. The antibody fragments are can be screened for utility using the same techniques employed with whole antibodies.

The "antigen- or epitope-binding portion or fragment" can be derived from an antibody of the present disclosure by a number of art-known techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. J. Nucl. Med. 23:1011-1019 (1982); Rousseaux et al. Methods Enzymology, 121:663-69, Academic Press, 1986, which are incorporated herein by reference in their entireties.

Pepsin digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen combining sites and is still capable of cross-linking antigen.

The Fab fragment may also contain the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments that have hinge cysteines between them. Other chemical couplings of antibody fragments known in the field are also useful in this application.

"Fv" is the minimum antibody fragment that contains a complete antigen recognition and binding site. This region consists of a dimer of one heavy and one light chain variable domain in tight, non-covalent association. It is in this configuration that the three CDRs of each variable domain interact to define an antigen-binding site on the surface of the VH-VL dimer. Collectively, the six CDRs confer antigen-binding specificity to the antibody. However, even a single variable domain (or half of a Fv comprising only three CDRs specific for an antigen) has the ability to recognize and bind the antigen, although at a lower affinity than the entire binding site.

The "light chains" of antibodies (immunoglobulins) from any vertebrate species can be assigned to one of two clearly distinct types, called kappa and lambda ($\lambda$), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called a, delta, epsilon, γ, and μ, respectively. The subunit structures and three-dimensional configurations of different classes of immunoglobulins are well known.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity. Methods to obtain "humanized antibodies" are well known to those skilled in the art. (see, e.g., Queen et al., Proc. Natl Acad Sci USA, 86:10029-10032 (1989), Hodgson et al., Bio/Technology, 9:421 (1991)). In one embodiment, the "humanized antibody" may be obtained by a genetic engineering approach that enables production of affinity-matured humanlike polyclonal antibodies in large animals such as, for example, rabbits (see, e.g. U.S. Pat. No. 7,129,084).

The terms "polypeptide", "peptide", and "protein", as used herein, are interchangeable and are defined to mean a biomolecule composed of amino acids linked by a peptide bond.

The terms "a", "an" and "the" as used herein are defined to mean "one or more" and include the plural unless the context is inappropriate.

By "isolated" is meant a biological molecule free from at least some of the components with which it naturally occurs. "Isolated," when used to describe the various polypeptides disclosed herein, means a polypeptide that has been identified and separated and/or recovered from a cell or cell culture from which it was expressed. Ordinarily, an isolated polypeptide will be prepared by at least one purification step. An "isolated antibody," refers to an antibody which is substantially free of other antibodies having different antigenic specificities.

"Recombinant" means the antibodies are generated using recombinant nucleic acid techniques in exogeneous host cells.

The term "antigen" refers to an entity or fragment thereof which can induce an immune response in an organism, particularly an animal, more particularly a mammal including a human. The term includes immunogens and regions thereof responsible for antigenicity or antigenic determinants.

Also as used herein, the term "immunogenic" refers to substances which elicit or enhance the production of antibodies, T-cells or other reactive immune cells directed against an immunogenic agent and contribute to an immune response in humans or animals. An immune response occurs when an individual produces sufficient antibodies, T-cells and other reactive immune cells against administered immunogenic compositions of the present disclosure to moderate or alleviate the disorder to be treated.

"Specific binding" or "specifically binds to" or is "specific for" a particular antigen or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

Specific binding for a particular antigen or an epitope can be exhibited, for example, by an antibody having a KD for an antigen or epitope of at least about $10^{-4}$ M, at least about $10^{-5}$ M, at least about $10^{-6}$ M, at least about $10^{-7}$ M, at least about $10^{-8}$ M, at least about $10^{-9}$, alternatively at least about $10^{-10}$ M, at least about $10^{-11}$ M, at least about $10^{-12}$ M, or greater, where KD refers to a dissociation rate of a particular antibody-antigen interaction. Typically, an antibody that specifically binds an antigen will have a KD that is 20-, 50-, 100-, 500-, 1000-, 5,000-, 10,000- or more times greater for a control molecule relative to the antigen or epitope.

Also, specific binding for a particular antigen or an epitope can be exhibited, for example, by an antibody having a KA or Ka for an antigen or epitope of at least 20-, 50-, 100-, 500-, 1000-, 5,000-, 10,000- or more times greater for the epitope relative to a control, where KA or Ka refers to an association rate of a particular antibody-antigen interaction.

"Homology" between two sequences is determined by sequence identity. If two sequences which are to be compared with each other differ in length, sequence identity preferably relates to the percentage of the nucleotide residues of the shorter sequence which are identical with the nucleotide residues of the longer sequence. Sequence identity can be determined conventionally with the use of computer programs. The deviations appearing in the comparison between a given sequence and the above-described sequences of the disclosure may be caused for instance by addition, deletion, substitution, insertion or recombination.

The application further provides immune-conjugates containing a drug unit linked to the mAbs or their fragments thereof as disclosed herein through a linker. The linker may be cleavable or noncleavable. In one embodiment, the linker is a chemical linker. In one embodiment, the linker comprises a covalent bond such as an ester bond, an ether bond, an amid bond, a disulphide bond, an imide bond, a sulfone bond, a phosphate bond, a phosphorus ester bond, a peptide bond, or a combination thereof. In one embodiment, the linker comprises a hydrophobic poly(ethylene glycol) linker. In one embodiment, the linker comprises a peptide bond.

The drug unit may include a chemotherapeutic agent, a growth inhibitory agent, a drug unit from class of calicheamicin, an antimitotic agent, a toxin, a radioactive isotope, a therapeutic agent, or a combination thereof. In one embodiment, the therapeutic agent comprises an antibody, a chemotherapy agent, an enzyme, or a combination thereof.

The application further provides pharmaceutical compositions. In one embodiment, the pharmaceutical composition comprises the mAbs or their fragments thereof, as disclosed herein, and a pharmaceutically acceptable carrier. In one embodiment, pharmaceutical composition comprises the immunoconjugate, as disclosed herein, and a pharmaceutically acceptable carrier.

The antibodies, their fragment thereof or the immune-conjugate can be prepared in a physiologically acceptable formulation and may comprise a pharmaceutically acceptable carrier, diluent and/or excipient using known techniques. For example, the antibody according to the disclosure may include any functionally equivalent antibody or functional parts thereof, in particular, the monoclonal antibody including any functionally equivalent antibody or functional parts thereof is combined with a pharmaceutically acceptable carrier, diluent and/or excipient to form a therapeutic composition. Suitable pharmaceutical carriers, diluents and/or excipients are well known in the art and include, for example, phosphate buffered saline solutions, water, emulsions such as oil/water emulsions, various types of wetting agents, sterile solutions, etc. In some embodiments, the formulation of the pharmaceutical composition can be accomplished according to standard methodology know to those of ordinary skill in the art.

Further biologically active agents may be present in the pharmaceutical composition of the disclosure dependent on its intended use. In one embodiment, the biologically active agent may include capecitabine, cisplatin, trastuzumab, fulvestrant, tamoxifen, letrozole, exemestane, anastrozole, aminoglutethimide, testolactone, vorozole, formestane, fadrozole, letrozole, erlotinib, lafatinib, dasatinib, gefitinib, imatinib, pazopinib, lapatinib, sunitinib, nilotinib, sorafenib, nab-palitaxel, calicheamicin, antimitotic agent, monomethyl auristatin E, emtansine, ozogamicin, or a derivative or a combination thereof.

In another aspect, the application provides methods for treating a subject using anti-CD3 antibodies or other molecules containing the antigen-binding portion of an anti-CD3 antibody for activation of human CD3+ T cells. In some embodiments, the methods include the steps of using the antibodies to stimulate a protective autoimmune response, to modify an immune response or to stimulate antigen-specific immune responses. In some embodiments, the methods include administering the disclosed composition into a subject for treating a cancer.

In some embodiments, the methods include the step of administering an effective amount of pharmaceutical composition disclosed thereof to a subject in need of such treatment. The compositions may be administered to a subject in the form of a solid, liquid or aerosol at a suitable, pharmaceutically effective dose. Examples of solid compositions include pills, creams, and implantable dosage units. Pills may be administered orally. Therapeutic creams may be administered topically. Implantable dosage units may be administered locally, for example, at a tumor site, or may be implanted for systematic release of the therapeutic composition, for example, subcutaneously. Examples of liquid compositions include formulations adapted for injection intramuscularly, subcutaneously, intravenously, intra-arterially, and formulations for topical and intraocular administration. Examples of aerosol formulations include inhaler formulations for administration to the lungs.

The compositions may be administered by standard routes of administration. In general, the composition may be administered by topical, oral, rectal, nasal, interdermal, intraperitoneal, or parenteral (for example, intravenous, subcutaneous, or intramuscular) routes.

In one embodiment, the administration can be parenterally, e.g. intravenously. Preparations for parenteral administration include sterile aqueous or non-aqueous solutions, suspensions and emulsions. Non-aqueous solvents include without being limited to it, propylene glycol, polyethylene glycol, vegetable oil such as olive oil, and injectable organic esters such as ethyl oleate. Aqueous solvents may be chosen from the group consisting of water, alcohol/aqueous solutions, emulsions or suspensions including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose) and others. Preservatives may also be present such as, for example, antimicrobials, anti-oxidants, chelating agents, inert gases, etc.

In some embodiments, the composition may be incorporated into sustained release matrices such as biodegradable polymers, the polymers being implanted in the vicinity of where delivery is desired, for example, at the site of a tumor. In one embodiment, a sustained release matrix may be used. The matrix may be made of materials, usually polymers which are degradable by enzymatic or acid/base hydrolysis or by dissolution. Once inserted into the body, the matrix is acted upon by enzymes and body fluids. The sustained release matrix desirably is chosen by biocompatible materials such as liposomes, polylactides (polylactide acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

The pharmaceutical composition may further comprise proteinaceous carriers such as, for example, serum albumin or immunoglobulin, particularly of human origin. In some embodiments, proteinaceous pharmaceutically active matter may be present in amounts between 1 ng and 10 mg per dose. In some embodiment, the regime of administration may be in the range of between 0.1 µg and 10 mg of the antibody according to the disclosure, particularly in a range 1.0 µg to 1.0 mg, and more particularly in a range of between 1.0 µg and 100 µg, with all individual numbers falling within these ranges also being part of the disclosure. If the administration occurs through continuous infusion a more proper dosage may be in the range of between 0.01 µg and 10 mg units per kilogram of body weight per hour with all individual numbers falling within these ranges also being part of the disclosure.

The method may include administration of a single dose, administration of repeated doses at predetermined time intervals, and sustained administration for a predetermined period of time. It is well known to those of ordinary skill in the art that the dosage of the composition will depend on various factors such as, for example, the condition of being treated, the particular composition used, and other clinical factors such as weight, size, sex and general health condition of the patient, body surface area, the particular compound or composition to be administered, other drugs being administered concurrently, and the route of administration.

The term "therapeutically effective amount" refers to the amount of antibody which, when administered to a human or animal, elicits a response which is sufficient to result in a therapeutic effect in said human or animal. The effective amount is readily determined by one of ordinary skill in the art following routine procedures.

The composition may be administered in combination with other compositions comprising an biologically active substance or compound. In one embodiment, the biologically active substance or compound may include compounds against oxidative stress, anti-apoptotic compounds, metal chelators, inhibitors of DNA repair such as pirenzepin and metabolites, 3-amino-1-propanesulfonic acid (3APS), 1,3-propanedisulfonate (1,3PDS), secretase activators, β- and γ-secretase inhibitors, tau proteins, neurotransmitter, β-sheet breakers, anti-inflammatory molecules, "atypical antipsychotics" such as, for example clozapine, ziprasidone, risperidone, aripiprazole or olanzapine or cholinesterase inhibitors (ChEls) such as tacrine, rivastigmine, donepezil, and/or galantamine and other drugs and nutritive supplements such as, for example, vitamin B12, cysteine, a precursor of acetylcholine, lecithin, choline, *Ginkgo biloba*, acyetyl-L-carnitine, idebenone, propentofylline, or a xanthine derivative.

The present disclosure may be understood more readily by reference to the following detailed description of specific embodiments included herein. Although the present disclosure has been described with reference to specific details of certain embodiments thereof, it is not intended that such details should be regarded as limitations upon the scope of the disclosure.

EXAMPLES

Example 1: Generation of Anti-CD3 Antibodies

Monoclonal antibodies against human CD3 were developed by immunizing New Zealand white rabbits. As shown in FIG. 1, animals were immunized with recombinant Human CD3 Delta-Epsilon Fc ("Knobs-into-hole"—KnH) and Gamma-Epsilon Fc (KnH) fusion proteins or HEK 293 cells transiently transfected with human or cynomolgus "CD3 complex" (alpha and beta T cell receptor, gamma, delta, and epsilon accessory chains) mixed 1:1 v/v with Complete or incomplete Freund's adjuvant (Cohort 1) or Titermax Gold (Cohort 2) alternating with Alhydrogel 2% (Alum) plus CpG 2007 and were performed by subcutaneous injection. Subsequent boosts were performed every 7 days through day 51 (Cohort 1) or day 68 (Cohort 2).

Figure 2D:
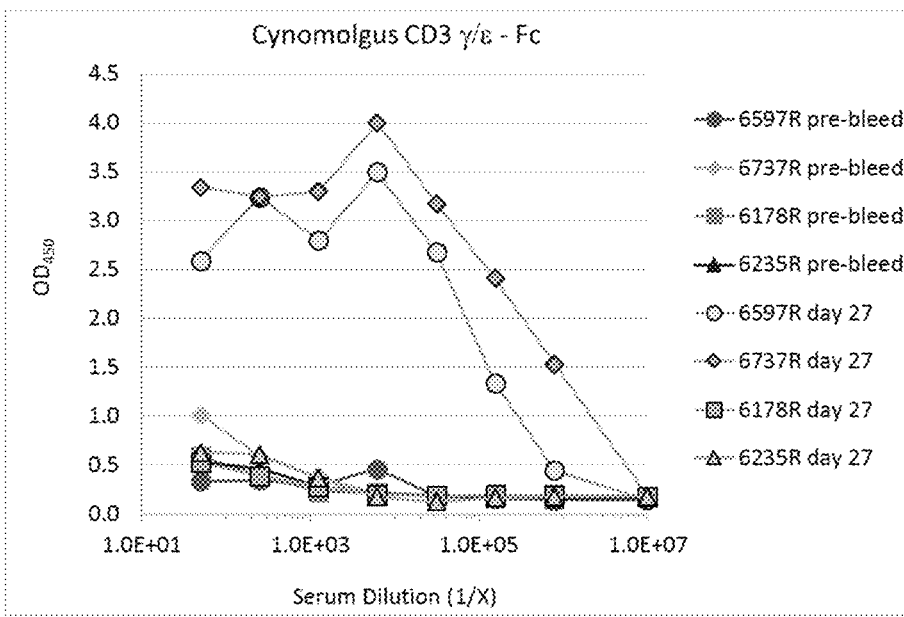
Figure 5B:
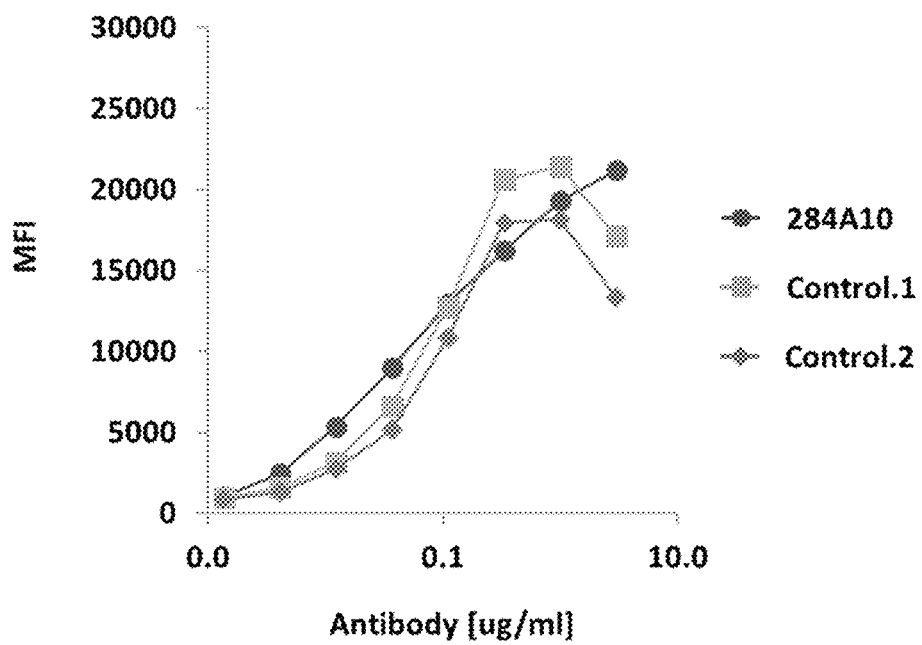
FIG. 5 shows the FACS analysis of example chimeric rabbit/human CD3-specific antibodies binding to the human T cell line Jurkat.
Figure 5C:
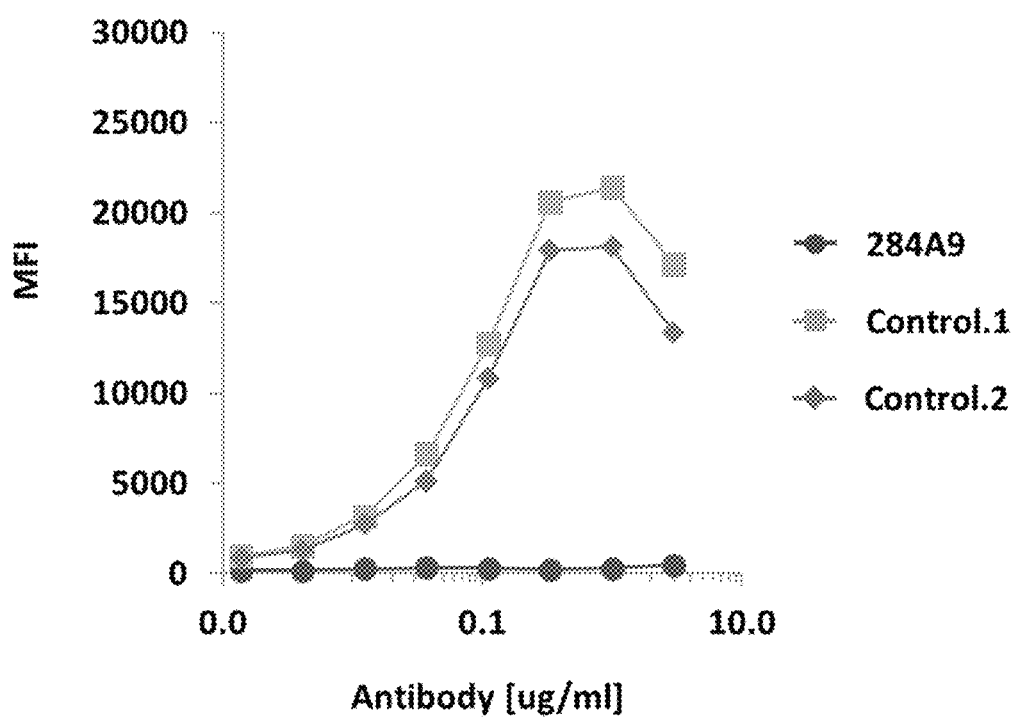
Figure 5D:
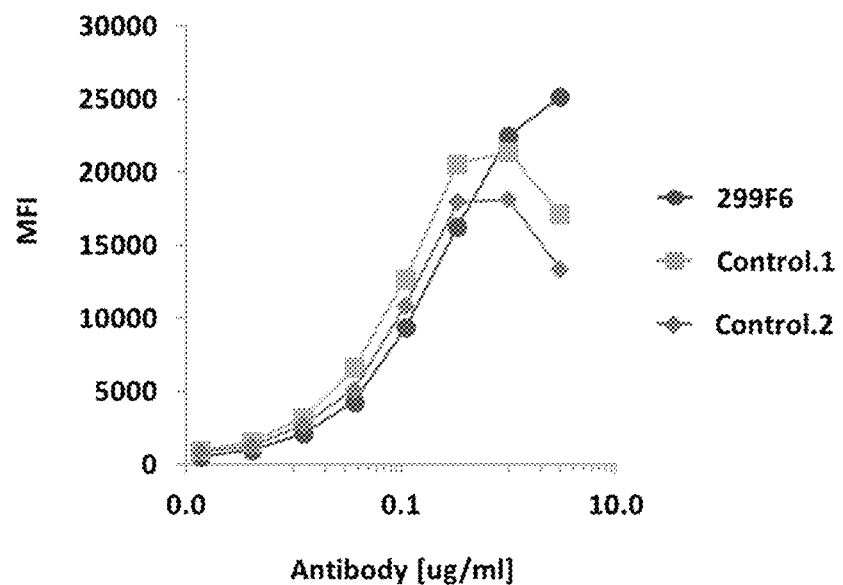
Figure 5E:
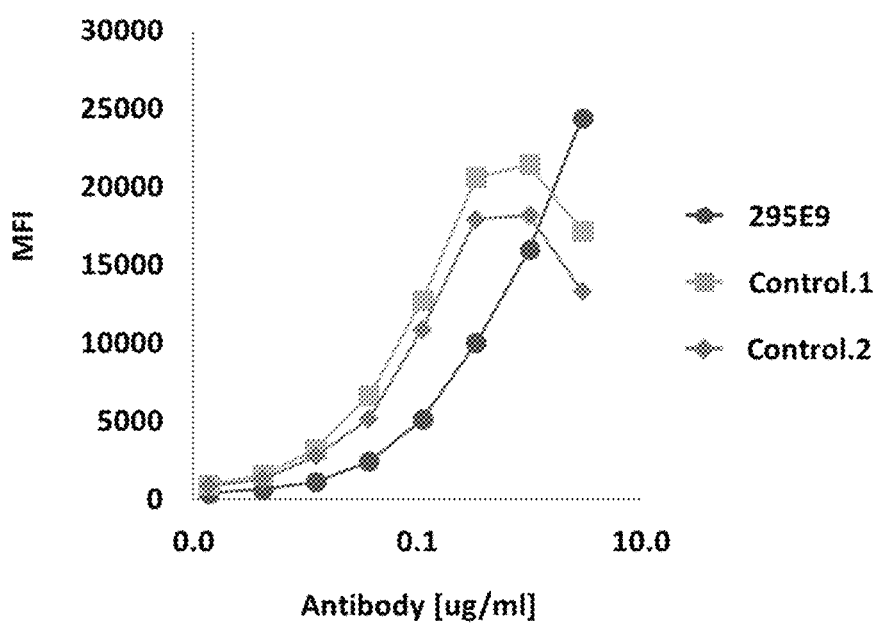
Figure 5F:
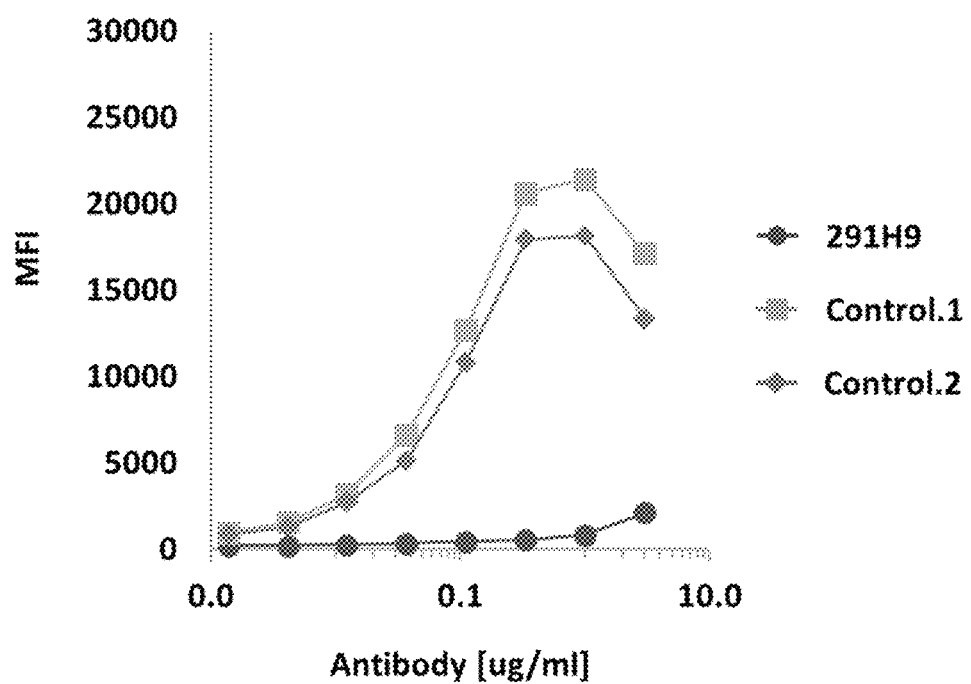
Figure 6B:
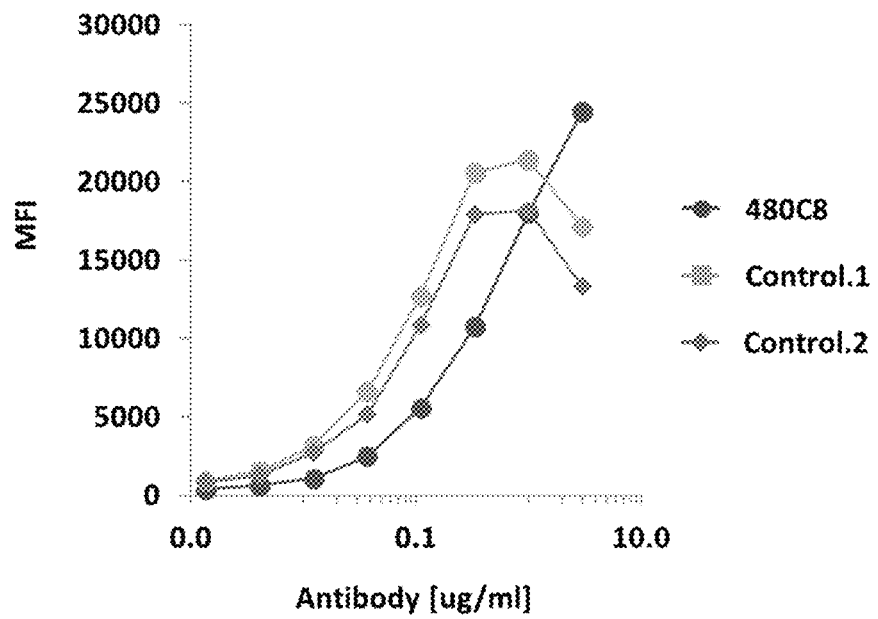
FIG. 6 shows the FACS analysis of example chimeric rabbit/human CD3-specific antibodies binding to the human T cell line Jurkat.
Figure 6C:
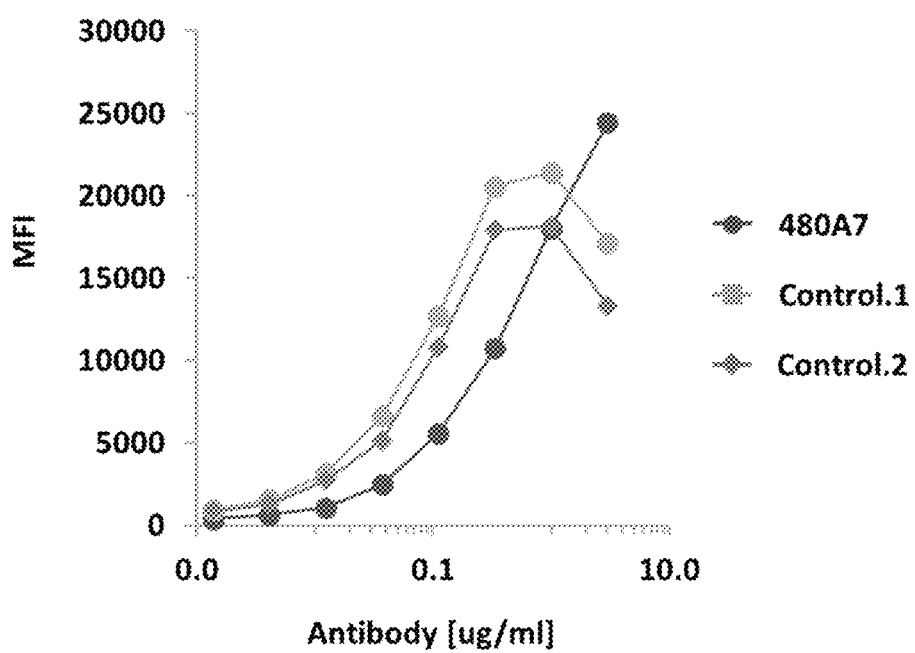
Figure 6D:
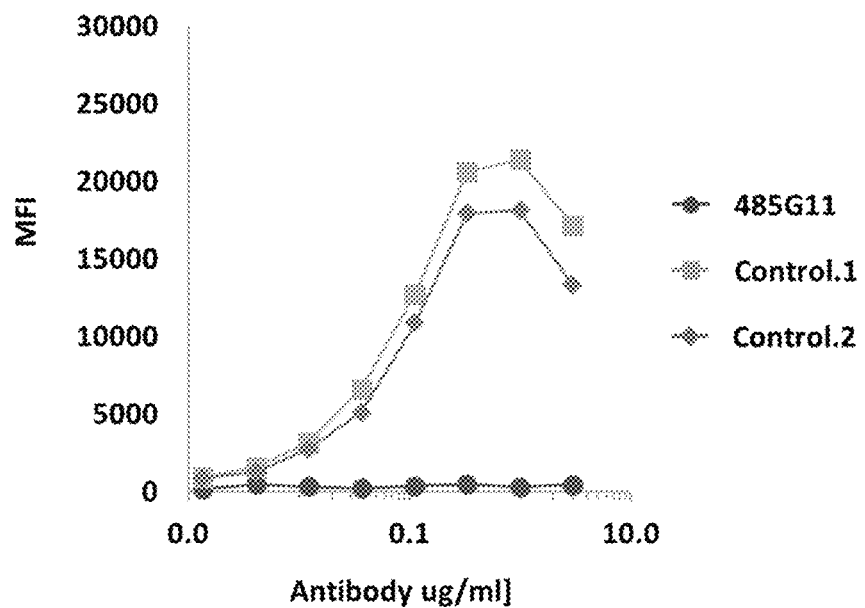
Figure 6E:
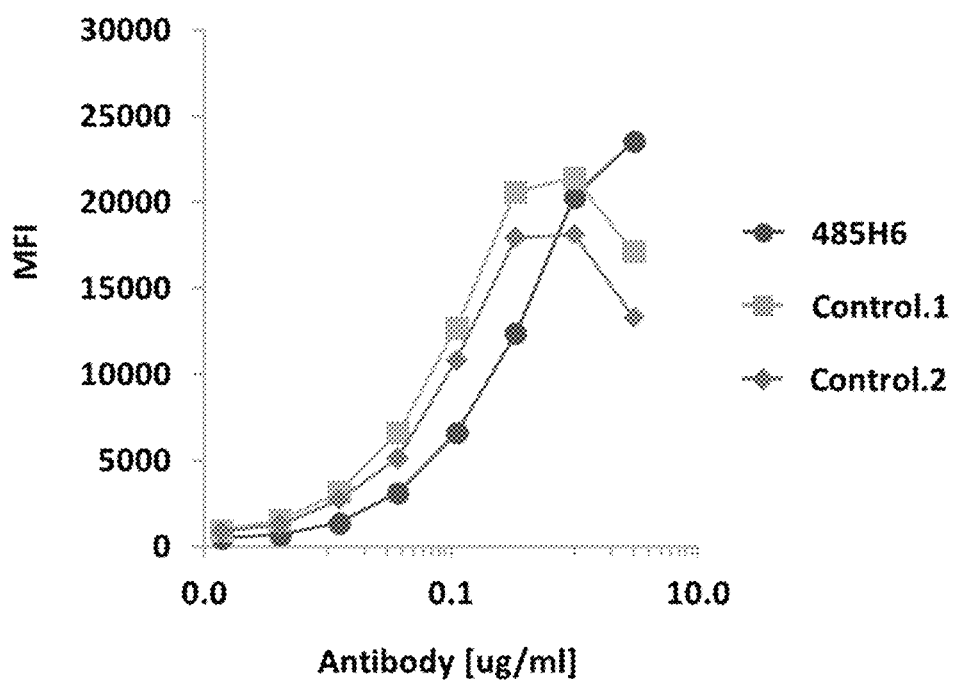

On week 5 the serum from the animals was tested for CD3 Delta-Epsilon Fc ("Knobs-into-hole"-KnH) and Gamma-Epsilon Fc (KnH) fusion protein titer by ELISA. Serum from each rabbit was obtained before immunization as a negative control. After immunization serum was again collected from each animal and compared to the pre-immunization serum from the same animal for the presence of CD3 Delta, Gamma, or Epsilon-specific IgG antibodies. As shown in FIG. 2 all animals immunized with human and cynomolgus CD3 Delta, Gamma, or Epsilon Fc fusion proteins developed detectable titers of IgG specific for human CD3 Delta-Epsilon Fc (plate 1), human CD3 Gamma-Epsilon Fc (plate 2), Cynomolgus CD3 Delta-Epsilon Fc (plate 3), Cynomolgus CD3 Gamma-Epsilon Fc CD3-Fc fusion proteins.

One rabbit in cohort No. 2, 6235R, which was immunized with human or cynomolgus CD3 transfected cells, showed serum IgG binding to the human and cynomolgus CD3 Delta, Gamma, or Epsilon Fc fusion proteins, indicating that the specificity was for the Delta, Gamma, or Epsilon part of the Fc fusion proteins. Antigen-specific B cells were enriched using biotinylated cynomolgus CD3 Delta, Gamma, or Epsilon Fc fusion proteins and seeded at limit dilution into multiple 96-well tissue culture plates and cultured for 9 days to allow their differentiation into plasma cells and for secretion of antibodies. The supernatants from these plasma cell cultures were screened by ELISA, flow cytometry (FACS), and functional assay for the presence of CD3-specific antibodies in a series of assays as listed below:

1. Binding to human CD3 Delta, Gamma, or Epsilon Fc fusion proteins—detection of Delta, Gamma, or Epsilon-specific IgG ELISA
2. Binding to Cynomolgus CD3 Delta, Gamma, or Epsilon Fc fusion proteins—detection of Delta, Gamma, or Epsilon-specific IgG ELISA
3. Binding to human IgG—counter-screen for detection of human IgG Fc-specific IgG ELISA
4. Binding to human T cell line Jurkat—detection of IgG which is specific for CD3 Delta, Gamma, or Epsilon FACS
5. Binding to Cynomolgus T cell line HSC-F—detection of IgG which is specific for CD3 Delta, Gamma, or Epsilon FACS
6. Binding to non-transfected human embryonic kidney (HEK) 293 cells—counter-screen for detection of IgG specific for unknown target(s) on cells that do not express human or cynomolgus CD3 Delta, Gamma, or Epsilon
7. Activation of purified human CD3+ T cells—detection of IL-2 secretion ELISA On day 9 of B cell culture the supernatants were separated from the B cells and stored in a separate plate for later analysis. RNAlater tissue storage reagent was added to each well in the B cell culture plate to preserve the RNA in the B cells for RT-PCR amplification of antibody variable regions.

After the BCC supernatants were screened for binding as in points 1-3 above 23 wells were identified that contained IgG that specifically recognized human and cynomolgus CD3 epsilon. This set of 23 wells were then screened for binding human and cynomolgus T cells, as well as activation of human T cells, and the results are shown in FIG. 3.

This set of 23 BCC wells identified through ELISA and FACS screening as having the desired antibodies we advanced to molecular "rescue" of the antibody variable regions. The light and heavy chain variable sequences were amplified by multiplex RT-PCR using degenerate primers designed to anneal to leader sequences and the constant regions of rabbit IgG and rabbit kappa sequences. Secondary PCR was performed separately for the light and heavy chains using nested primers containing restriction sites. Amplicons from the variable heavy chain PCR were cloned into an expression vector containing human IgG1. Light chain amplicons were cloned into an expression vector containing human IgK. Resulting clones were sequenced and analyzed.

The heavy and light chain expression plasmids generated from each well were transiently co-transfected to produce rabbit/human chimeric antibodies. Recombinant antibody supernatants were confirmed to contain antibodies specific for Cynomolgus CD3 Delta, Gamma, or Epsilon using bio-layer interferometry analysis on a ForteBio Octet Red 96 instrument. Anti-human Fc biosensors (Pall ForteBio) were used to capture antibodies in the supernatants. Association to Cynomolgus CD3 Delta, Gamma, or Epsilon was observed by real-time interferometry by placing the biosensors in wells containing recombinant human ROR1 extracellular domain protein. Dissociation was measured after transfer of the biosensors into wells containing 10× kinetics buffer (Pall ForteBio). The software provided by the manufacturer was used to analyze the interferometry data.

A summary of the primary BCC screening data and the corresponding screening data for 22 recombinant chimeric rabbit/human IgG antibodies is shown in FIG. 4. From the original 23 BCC wells 22 chimeric antibodies were rescued, 6 showed binding to the Cynomolgus CD3 Delta/Epsilon Fc fusion protein, 5 of 6 showed binding to Cynomolgus CD3 Gamma/Epsilon Fc fusion protein, and 4 of 5 showed binding to the human T cell line Jurkat (FIG. 5 and FIG. 4).

A second round of B cell culture was setup with Cynomolgus CD3 Delta, Gamma, or Epsilon Fc fusion protein binding IgG+ B cells from rabbit 6235R sorted at 1 per well into multiple 96-well tissue culture plates and cultured for 9 days to allow their differentiation into plasma cells and for secretion of antibodies. The supernatants from these plasma cell cultures were screened by ELISA, flow cytometry (FACS), and functional assay for the presence of CD3-specific antibodies as shown in the list above. As shown in FIG. 6, 5 chimeric rabbit/human antibodies were tested for binding to the human T cell line Jurkat and 3 of 5 showed binding.

From the first BCC 4 chimeric rabbit/human antibodies, and from the second BCC 3 chimeric rabbit/human antibodies, showed binding to the human T cell line Jurkat for a total of 7. These 7 antibodies and 2 additional non-binding antibodies were analyzed for activation of human CD3+ T cells. As shown in FIG. 7, of the 9 antibodies tested 7 activated human CD3+ T cells, 6 of them strongly, 284A10, 295E9, 299F6, 480A7, 48008, 485H6.

The heavy and light chain variable regions for the 6 chimeric rabbit/human IgG antibodies listed above were humanized. Humanized variants for 3 of 6 showed similar binding kinetics to human CD3 Delta/Epsilon Fc and/or Gamma/Epsilon Fc fusion protein by octet analysis which is summarized in FIG. 8.

```
                            SEQUENCE LISTING

SEQ ID NO: 1
284A10 CHIMERIC LIGHT CHAIN FULL-LENGTH NUCLEOTIDE SEQUENCE
GATGTCGTGATGACCCAGACTCCTCCCTCCGTGTCTGCAGCTGTGGGAGGCACAGTCACCATCAAGTGCCAGGCCAGTGAGAGCATTA
GCAGTTGGTTAGCCTGGTATCAGCAGAAACCAGGGCAGCCTCCCAAGCTCCTGATCTACGAAGCATCCAAACTGGCATCTGGGGTCCC
ATCGCGGTTCAGTGGCAGTGGATCTGGGACAGAGTTCACTCTCACCATCAGTGACCTGGAGTGTGCCGATGCTGCCACTTACTACTGT
CAAGGCTATTTTTATTTTATTAGTCGTACTTATGTAAATTCTTTCGGCGGAGGCACCGAGGTGGAGTTCAAACGTACGGTGGCTGCAC
CATCTGTCTTCATCTTCCCGCCATCTGATGAGCAGTTGAAATCTGGAACTGCCTCTGTTGTGTGCCTGCTGAATAACTTCTATCCCAG
AGAGGCCAAAGTACAGTGGAAGGTGGATAACGCCCTCCAATCGGGTAACTCCCAGGAGAGTGTCACAGAGCAGGACAGCAAGGACAGC
ACCTACAGCCTCAGCAGCACCCTGACGCTGAGCAAAGCAGACTACGAGAAACACAAAGTCTACGCCTGCGAAGTCACCCATCAGGGCC
TGAGCTCGCCCGTCACAAAGAGCTTCAACAGGGGAGAGTGT

SEQ ID NO: 2
284A10 CHIMERIC LIGHT CHAIN VARIABLE LIGHT CHAIN NUCLEOTIDE SEQUENCE
GATGTCGTGATGACCCAGACTCCTCCCTCCGTGTCTGCAGCTGTGGGAGGCACAGTCACCATCAAGTGCCAGGCCAGTGAGAGCATTA
GCAGTTGGTTAGCCTGGTATCAGCAGAAACCAGGGCAGCCTCCCAAGCTCCTGATCTACGAAGCATCCAAACTGGCATCTGGGGTCCC
ATCGCGGTTCAGTGGCAGTGGATCTGGGACAGAGTTCACTCTCACCATCAGTGACCTGGAGTGTGCCGATGCTGCCACTTACTACTGT
CAAGGCTATTTTTATTTTATTAGTCGTACTTATGTAAATTCTTTCGGCGGAGGCACCGAGGTGGAGTTCAAA

SEQ ID NO: 3
284A10 CHIMERIC LIGHT CHAIN FULL-LENGTH AMINO ACID SEQUENCE. HUMAN KAPPA CONSTANT
DOMAIN IS UNDERLINED
DVVMTQTPPSVSAAVGGTVTIKCQASESISSWLAWYQQKPGQPPKLLIYEASKLASGVPSRFSGSGSGTEFTLTISDLECADAATYYC
QGYFYFISRTYVNSFGGGTEVEFKRTVAAPSVFIFPPSDEQLKSGTASVVCLLNNFYPREAKVQWKVDNALQSGNSQESVTEQDSKDS
TYSLSSTLTLSKADYEKHKVYACEVTHQGLSSPVTKSFNRGEC

SEQ ID NO: 4
284A10 CHIMERIC LIGHT CHAIN VARIABLE LIGHT CHAIN AMINO ACID SEQUENCE. COMPIMENTARITY
DETERMINING REGIONS ARE UNDERLINED
DVVMTQTPPSVSAAVGGTVTIKCQASESISSWLAWYQQKPGQPPKLLIYEASKLASGVPSRFSGSGSGTEFTLTISDLECADAATYYC
QGYFYFISRTYVNSFGGGTEVEFK

SEQ ID NO: 5
284A10 CHIMERIC HEAVY CHAIN FULL-LENGTH NUCLEOTIDE SEQUENCE
CAGTCGCTGGAGGAGTCCGGGGGTCGCCTGGTCACGCCTGGGACGCCCCTGACACTCACCTGCACAGTCTCTGGATTCACCATCAGTA
CCAATGCAATGAGCTGGGTCCGCCAGGTTCCAGGGAAGGGGCTGGAGTGGATCGGAGTCATTACTGGTCGTGATATCACATACTACGC
GAGCTGGGCGAAAGGCCGATTCACCATCTCCAAAACCTCGTCGACCACGGTGGATCTGAAAATGACCAGTCTGACAGCCGAGGACTCG
GCCACCTATTTCTGTGCCAGAGACGGTGGTTCTTCTGCTATTACTAGTAACAACATTTGGGGCCCAGGCACCCTCGTCACCGTCTCGA
GCGCTAGCACCAAGGGCCCATCGGTCTTCCCCCTGGCACCCTCCTCCAAGAGCACCTCTGGGGGCACAGCGGCCCTGGGCTGCCTGGT
CAAGGACTACTTCCCCGAACCGGTGACGGTGTCGTGGAACTCAGGCGCCCTGACCAGCGGCGTGCACACCTTCCCGGCTGTCCTACAG
TCCTCAGGACTCTACTCCCTCAGCAGCGTGGTGACCGTGCCCTCCAGCAGCTTGGGCACCCAGACCTACATCTGCAACGTGAATCACA
AGCCCAGCAACACCAAGGTGGACAAGAGAGTTGAGCCCAAATCTTGTGACAAAACTCACACATGCCCACCGTGCCCAGCACCTGAAGC
CGCGGGGGCACCGTCAGTCTTCCTCTTCCCCCCAAAACCCAAGGACACCCTCATGATCTCCCGGACCCCTGAGGTCACATGCGTGGTG
GTGGACGTGAGCCACGAAGACCCTGAGGTCAAGTTCAACTGGTACGTGGACGGCGTGGAGGTGCATAATGCCAAGACAAAGCCGCGGG
AGGAGCAGTACAACAGCACGTACCGTGTGGTCAGCGTCCTCACCGTCCTGCACCAGGACTGGCTGAATGGCAAGGAGTACAAGTGCGC
GGTCTCCAACAAAGCCCTCCCAGCCCCCATCGAGAAAACCATCTCCAAAGCCAAAGGGCAGCCCCGAGAACCACAGGTGTACACCCTG
CCCCCATCCCGGGATGAGCTGACCAAGAACCAGGTCAGCCTGACCTGCCTGGTCAAAGGCTTCTATCCCAGCGACATCGCCGTGGAGT
GGGAGAGCAATGGGCAGCCGGAGAACAACTACAAGACCACGCCTCCCGTGCTGGACTCCGACGGCTCCTTCTTCCTCTATAGCAAGCT
CACCGTGGACAAGAGCAGGTGGCAGCAGGGGAACGTCTTCTCATGCTCCGTGATGCATGAGGCTCTGCACAACCACTACACGCAGAAG
AGCCTCTCCCTGTCTCCGGGT

SEQ ID NO: 6
284A10 CHIMERIC HEAVY CHAIN VARIABLE HEAVY CHAIN NUCLEOTIDE SEQUENCE
CAGTCGCTGGAGGAGTCCGGGGGTCGCCTGGTCACGCCTGGGACGCCCCTGACACTCACCTGCACAGTCTCTGGATTCACCATCAGTA
CCAATGCAATGAGCTGGGTCCGCCAGGTTCCAGGGAAGGGGCTGGAGTGGATCGGAGTCATTACTGGTCGTGATATCACATACTACGC
GAGCTGGGCGAAAGGCCGATTCACCATCTCCAAAACCTCGTCGACCACGGTGGATCTGAAAATGACCAGTCTGACAGCCGAGGACTCG
GCCACCTATTTCTGTGCCAGAGACGGTGGTTCTTCTGCTATTACTAGTAACAACATTTGGGGCCCAGGCACCCTCGTCACCGTCTCGA
GC

SEQ ID NO: 7
284A10 CHIMERIC HEAVY CHAIN FULL-LENGTH AMINO ACID SEQUENCE. HUMAN GAMMA-1
CONSTANT DOMAIN IS UNDERLINED
QSLEESGGRLVTPGTPLTLTCTVSGFTISTNAMSWVRQVPGKGLEWIGVITGRDITYYASWAKGRFTISKTSSTTVDLKMTSLTAEDS
ATYFCARDGGSSAITSNNIWGPGTLVTVSSASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKRVEPKSCDKTHTCPPCPAPEAAGAPSVFLFPPKPKDTLMISRTPEVTCVV
VDVSHEDPEVKFNWYVDGVEVHNAKTKPREEQYNSTYRVVSVLTVLHQDWLNGKEYKCAVSNKALPAPIEKTISKAKGQPREPQVYTL
PPSRDELTKNQVSLTCLVKGFYPSDIAVEWESNGQPENNYKTTPPVLDSDGSFFLYSKLTVDKSRWQQGNVFSCSVMHEALHNHYTQK
SLSLSPG
```

-continued

SEQUENCE LISTING

SEQ ID NO: 8
284A10 CHIMERIC HEAVY CHAIN VARIABLE HEAVY CHAIN AMINO ACID SEQUENCE.
COMPLIMENTARITY DETERMINING REGIONS ARE UNDERLINED
QSLEESGGRLVTPGTPLTLTCTVSGFTIS<u>TNAMS</u>WVRQVPGKGLEWIG<u>VITGRDITYYASWAKG</u>RFTISKTSSTTVDLKMTSLTAEDS
ATYFCAR<u>DGGSSAITSNNI</u>WGPGTLVTVSS

SEQ ID NO: 9
299F6 CHIMERIC LIGHT CHAIN FULL-LENGTH NUCLEOTIDE SEQUENCE
GATGTCGTGATGACCCAGACTCCATCCTCCGTGTCTGCAGCTGTGGGAGGCACAGTCACCATCAATTGCCAAGCCAGTGAGAGCATTA
GCAGTTGGTTAGCCTGGTATCAGCAGAAACCAGGGCAGCCTCCCAAGCTCCTGATCTACGAAGCATCCAAACTGGCATCTGGGGTCCC
ATCGCGGTTCAGTGGCAGTGGATCTGGGACAGAGTTCACTCTCACCATCAGCGGCGTGCAGTGTGACGATGCTGCCACTTACTACTGT
CAAGGCTATTTTTATTTTATTAGTCGTAGTTATGTGAATGCTTTCGGCGGAGGGACCGAGGTGGGGGTCAAACGTACGGTGGCTGCAC
CATCTGTCTTCATCTTCCCGCCATCTGATGAGCAGTTGAAATCTGGAACTGCCTCTGTTGTGTGCCTGCTGAATAACTTCTATCCCAG
AGAGGCCAAAGTACAGTGGAAGGTGGATAACGCCCTCCAATCGGGTAACTCCCAGGAGAGTGTCACAGAGCAGGACAGCAAGGACAGC
ACCTACAGCCTCAGCAGCACCCTGACGCTGAGCAAAGCAGACTACGAGAAACACAAAGTCTACGCCTGCGAAGTCACCCATCAGGGCC
TGAGCTCGCCCGTCACAAAGAGCTTCAACAGGGGAGAGTGT

SEQ ID NO: 10
299F6 CHIMERIC LIGHT CHAIN VARIABLE LIGHT CHAIN NUCLEOTIDE SEQUENCE
GATGTCGTGATGACCCAGACTCCATCCTCCGTGTCTGCAGCTGTGGGAGGCACAGTCACCATCAATTGCCAAGCCAGTGAGAGCATTA
GCAGTTGGTTAGCCTGGTATCAGCAGAAACCAGGGCAGCCTCCCAAGCTCCTGATCTACGAAGCATCCAAACTGGCATCTGGGGTCCC
ATCGCGGTTCAGTGGCAGTGGATCTGGGACAGAGTTCACTCTCACCATCAGCGGCGTGCAGTGTGACGATGCTGCCACTTACTACTGT
CAAGGCTATTTTTATTTTATTAGTCGTAGTTATGTGAATGCTTTCGGCGGAGGGACCGAGGTGGGGGTCAAA

SEQ ID NO: 11
299F6 CHIMERIC LIGHT CHAIN FULL-LENGTH AMINO ACID SEQUENCE. HUMAN KAPPA CONSTANT
DOMAIN IS UNDERLINED
DVVMTQTPSSVSAAVGGTVTINCQASESISSWLAWYQQKPGQPPKLLIYEASKLASGVPSRFSGSGSGTEFTLTISDLECADAATYYC
QGYFYFISRSYVNAFGGGTEVVFK<u>RTVAAPSVFIFPPSDEQLKSGTASVVCLLNNFYPREAKVQWKVDNALQSGNSQESVTEQDSKDS
TYSLSSTLTLSKADYEKHKVYACEVTHQGLSSPVTKSFNRGEC</u>

SEQ ID NO: 12
299F6 CHIMERIC LIGHT CHAIN VARIABLE LIGHT CHAIN AMINO ACID SEQUENCE. COMPIMENTARITY
DETERMINING REGIONS ARE UNDERLINED
DVVMTQTPSSVSAAVGGTVTINC<u>QASESISSWLA</u>WYQQKPGQPPKLLIY<u>EASKLAS</u>GVPSRFSGSGSGTEFTLTISDLECADAATYYC
<u>QGYFYFISRSYVNA</u>FGGGTEVVFK

SEQ ID NO: 13
299F6 CHIMERIC HEAVY CHAIN FULL-LENGTH NUCLEOTIDE SEQUENCE
CAGTCGCTGGAGGAGTCCGGGGGTCGCCTGGTCACGCCTGGGACGCCCCTGACACTCACCTGCACAGTCTCTGGATTCACCATCAGTA
GCAATGCAATGAGCTGGGTCCGCCAGGCTCCAGGGAAGGGGCTGGAGTGGATCGGAGTCATTACTGGTCGTGATATCACATACTACGC
GAACTGGGCGAAAGGCCGATTCACCATCTCCAAAACCTCGTCGACCACGGTGGATCTGAAAATGACCAGTCTGACAGCCGAGGACTCG
GCCACCTATTTCTGTGCCAGAGACGGTGGTTCTTCTGCTATTACTAGTAACAACATTTGGGGCCCAGGGACCCTGGTCACCGTCTCGA
GCGCTAGCACCAAGGGCCCATCGGTCTTCCCCCTGGCACCCTCCTCCAAGAGCACCTCTGGGGGCACAGCGGCCCTGGGCTGCCTGGT
CAAGGACTACTTCCCCGAACCGGTGACGGTGTCGTGGAACTCAGGCGCCCTGACCAGCGGCGTGCACACCTTCCCGGCTGTCCTACAG
TCCTCAGGACTCTACTCCCTCAGCAGCGTGGTGACCGTGCCCTCCAGCAGCTTGGGCACCCAGACCTACATCTGCAACGTGAATCACA
AGCCCAGCAACACCAAGGTGGACAAGAGAGTTGAGCCCAAATCTTGTGACAAAACTCACACATGCCCACCGTGCCCAGCACCTGAAGC
CGCGGGGGCACCGTCAGTCTTCCTCTTCCCCCCAAAACCCAAGGACACCCTCATGATCTCCCGGACCCCTGAGGTCACATGCGTGGTG
GTGGACGTGAGCCACGAAGACCCTGAGGTCAAGTTCAACTGGTACGTGGACGGCGTGGAGGTGCATAATGCCAAGACAAAGCCGCGGG
AGGAGCAGTACAACAGCACGTACCGTGTGGTCAGCGTCCTCACCGTCCTGCACCAGGACTGGCTGAATGGCAAGGAGTACAAGTGCGC
GGTCTCCAACAAAGCCCTCCCAGCCCCCATCGAGAAAACCATCTCCAAAGCCAAAGGGCAGCCCCGAGAACCACAGGTGTACACCCTG
CCCCCATCCCGGGATGAGCTGACCAAGAACCAGGTCAGCCTGACCTGCCTGGTCAAAGGCTTCTATCCCAGCGACATCGCCGTGGAGT
GGGAGAGCAATGGGCAGCCGGAGAACAACTACAAGACCACGCCTCCCGTGCTGGACTCCGACGGCTCCTTCTTCCTCTATAGCAAGCT
CACCGTGGACAAGAGCAGGTGGCAGCAGGGGAACGTCTTCTCATGCTCCGTGATGCATGAGGCTCTGCACAACCACTACACGCAGAAG
AGCCTCTCCCTGTCTCCGGGT

SEQ ID NO: 14
299F6 CHIMERIC HEAVY CHAIN VARIABLE HEAVY CHAIN NUCLEOTIDE SEQUENCE
CAGTCGCTGGAGGAGTCCGGGGGTCGCCTGGTCACGCCTGGGACGCCCCTGACACTCACCTGCACAGTCTCTGGATTCACCATCAGTA
GCAATGCAATGAGCTGGGTCCGCCAGGCTCCAGGGAAGGGGCTGGAGTGGATCGGAGTCATTACTGGTCGTGATATCACATACTACGC
GAACTGGGCGAAAGGCCGATTCACCATCTCCAAAACCTCGTCGACCACGGTGGATCTGAAAATGACCAGTCTGACAGCCGAGGACTCG
GCCACCTATTTCTGTGCCAGAGACGGTGGTTCTTCTGCTATTACTAGTAACAACATTTGGGGCCCAGGGACCCTGGTCACCGTCTCGA
GC

SEQ ID NO: 15
299F6 CHIMERIC HEAVY CHAIN FULL-LENGTH AMINO ACID SEQUENCE. HUMAN GAMMA-1 CONSTANT
DOMAIN IS UNDERLINED
QSLEESGGRLVTPGTPLTLTCTVSGFTISSNAMSWVRQAPGKGLEWIGVITGRDITYYANWAKGRFTISKTSSTTVDLKMTSLTAEDS
ATYFCARDGGSSAITSNNIWGPGTLVTVSS<u>ASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKRVEPKSCDKTHTCPPCPAPEAAGAPSVFLFPPKPKDTLMISRTPEVTCVV
VDVSHEDPEVKFNWYVDGVEVHNAKTKPREEQYNSTYRVVSVLTVLHQDWLNGKEYKCAVSNKALPAPIEKTISKAKGQPREPQVYTL
PPSRDELTKNQVSLTCLVKGFYPSDIAVEWESNGQPENNYKTTPPVLDSDGSFFLYSKLTVDKSRWQQGNVFSCSVMHEALHNHYTQK
SLSLSPG</u>

SEQUENCE LISTING

SEQ ID NO: 16
299F6 CHIMERIC HEAVY CHAIN VARIABLE HEAVY CHAIN AMINO ACID SEQUENCE. COMPLIMENTARITY
DETERMINING REGIONS ARE UNDERLINED
QSLEESGGRLVTPGTPLTLTCTVSGFTISS<u>NAMS</u>WVRQAPGKGLEWIG<u>VITGRDITYYANWAKG</u>RFTISKTSSTTVDLKMTSLTAEDS
ATYFCAR<u>DGSSAITSNNI</u>WGPGTLVTVSS

SEQ ID NO: 17
480C8 CHIMERIC LIGHT CHAIN FULL-LENGTH NUCLEOTIDE SEQUENCE
GATGTCGTGATGACCCAGACTCCATCCTCCGTGTCTGCAGCTGTGGGAGGCACAGTCACCATCAATTGCCAAGCCAGTGAGAGCATTA
GCAGTTGGTTAGCCTGGTATCAGCAGAAACCAGGGCAGCCTCCCAAGCTCCTGATCTACGAAGCATCCAAACTGGCATCTGGGGTCCC
ATCGCGGTTCAGTGGCAGTGGATCTGGGACAGAGTTCACTCTCACCATCAGCGACCTGGAGTGTGCCGATGCTGCCACTTACTACTGT
CAAGGCTATTTTTATTTTATTAGTCGTACTTATGTAAATGCTTTCGGCGGAGGGACCGAGGTGGAGTTCAAACGTACGGTGGCTGCAC
CATCTGTCTTCATCTTCCCGCCATCTGATGAGCAGTTGAAATCTGGAACTGCCTCTGTTGTGTGCCTGCTGAATAACTTCTATCCCAG
AGAGGCCAAAGTACAGTGGAAGGTGGATAACGCCCTCCAATCGGGTAACTCCCAGGAGAGTGTCACAGAGCAGGACAGCAAGGACAGC
ACCTACAGCCTCAGCAGCACCCTGACGCTGAGCAAAGCAGACTACGAGAAACACAAAGTCTACGCCTGCGAAGTCACCCATCAGGGCC
TGAGCTCGCCCGTCACAAAGAGCTTCAACAGGGGAGAGTGT

SEQ ID NO: 18
480C8 CHIMERIC LIGHT CHAIN VARIABLE LIGHT CHAIN NUCLEOTIDE SEQUENCE
GATGTCGTGATGACCCAGACTCCATCCTCCGTGTCTGCAGCTGTGGGAGGCACAGTCACCATCAATTGCCAAGCCAGTGAGAGCATTA
GCAGTTGGTTAGCCTGGTATCAGCAGAAACCAGGGCAGCCTCCCAAGCTCCTGATCTACGAAGCATCCAAACTGGCATCTGGGGTCCC
ATCGCGGTTCAGTGGCAGTGGATCTGGGACAGAGTTCACTCTCACCATCAGCGACCTGGAGTGTGCCGATGCTGCCACTTACTACTGT
CAAGGCTATTTTTATTTTATTAGTCGTACTTATGTAAATGCTTTCGGCGGAGGGACCGAGGTGGAGTTCAAA

SEQ ID NO: 19
480C8 CHIMERIC LIGHT CHAIN FULL-LENGTH AMINO ACID SEQUENCE. HUMAN KAPPA CONSTANT
DOMAIN IS UNDERLINED
DVVMTQTPSSVSAAVGGTVTINCQASESISSWLAWYQQKPGQPPKLLIYEASKLASGVPSRFSGSGSGTEFTLTISDLECADAATYYC
QGYFYFISRTYVNAFGGGTEVEFK<u>RTVAAPSVFIFPPSDEQLKSGTASVVCLLNNFYPREAKVQWKVDNALQSGNSQESVTEQDSKDS
TYSLSSTLTLSKADYEKHKVYACEVTHQGLSSPVTKSFNRGEC</u>

SEQ ID NO: 20
480C8 CHIMERIC LIGHT CHAIN VARIABLE LIGHT CHAIN AMINO ACID SEQUENCE. COMPLIMENTARITY
DETERMINING REGIONS ARE UNDERLINED
DVVMTQTPSSVSAAVGGTVTINC<u>QASESISSWLA</u>WYQQKPGQPPKLLIY<u>EASKLAS</u>GVPSRFSGSGSGTEFTLTISDLECADAATYYC
<u>QGYFYFISRTYVNA</u>FGGGTEVEFK

SEQ ID NO: 21
480C8 CHIMERIC HEAVY CHAIN FULL-LENGTH NUCLEOTIDE SEQUENCE
CAGTCGCTGGAGGAGTCCGGGGGTCGCCTGGTCACGCCTGGGACGCCCCTGACACTCACCTGCACAGTCTCTGGAATCGACCTCAGTA
GCAATGCAATGAGCTGGGTCCGCCAGGCTCCAGGGAAGGGGCTGGAGTGGATCGGAGTCATTACTGGTCGTGATATCACATACTACGC
GAGCTGGGCGAAAGGCCGATTCACCATCTCCAAAACCTCGTCGACCACGGTGGATCTGAAAATGACCAGTCTGACAGCCGAGGACTCG
GCCACCTATTTCTGTGCCAGAGACGGTGGTTCTTCTGCTATTAATAGTAAGAACATTTGGGGCCAAGGCACCCTGGTCACCGTCTCGA
GCGCTAGCACCAAGGGCCCATCGGTCTTCCCCCTGGCACCCTCCTCCAAGAGCACCTCTGGGGGCACAGCGGCCCTGGGCTGCCTGGT
CAAGGACTACTTCCCCGAACCGGTGACGGTGTCGTGGAACTCAGGCGCCCTGACCAGCGGCGTGCACACCTTCCCGGCTGTCCTACAG
TCCTCAGGACTCTACTCCCTCAGCAGCGTGGTGACCGTGCCCTCCAGCAGCTTGGGCACCCAGACCTACATCTGCAACGTGAATCACA
AGCCCAGCAACACCAAGGTGGACAAGAGAGTTGAGCCCAAATCTTGTGACAAAACTCACACATGCCCACCGTGCCCAGCACCTGAAGC
CGCGGGGGCACCGTCAGTCTTCCTCTTCCCCCCAAAACCCAAGGACACCCTCATGATCTCCCGGACCCCTGAGGTCACATGCGTGGTG
GTGGACGTGAGCCACGAAGACCCTGAGGTCAAGTTCAACTGGTACGTGGACGGCGTGGAGGTGCATAATGCCAAGACAAAGCCGCGGG
AGGAGCAGTACAACAGCACGTACCGTGTGGTCAGCGTCCTCACCGTCCTGCACCAGGACTGGCTGAATGGCAAGGAGTACAAGTGCGC
GGTCTCCAACAAAGCCCTCCCAGCCCCCATCGAGAAAACCATCTCCAAAGCCAAAGGGCAGCCCCGAGAACCACAGGTGTACACCCTG
CCCCCATCCCGGGATGAGCTGACCAAGAACCAGGTCAGCCTGACCTGCCTGGTCAAAGGCTTCTATCCCAGCGACATCGCCGTGGAGT
GGGAGAGCAATGGGCAGCCGGAGAACAACTACAAGACCACGCCTCCCGTGCTGGACTCCGACGGCTCCTTCTTCCTCTATAGCAAGCT
CACCGTGGACAAGAGCAGGTGGCAGCAGGGGAACGTCTTCTCATGCTCCGTGATGCATGAGGCTCTGCACAACCACTACACGCAGAAG
AGCCTCTCCCTGTCTCCGGGT

SEQ ID NO: 22
480C8 CHIMERIC HEAVY CHAIN VARIABLE HEAVY CHAIN NUCLEOTIDE SEQUENCE
CAGTCGCTGGAGGAGTCCGGGGGTCGCCTGGTCACGCCTGGGACGCCCCTGACACTCACCTGCACAGTCTCTGGAATCGACCTCAGTA
GCAATGCAATGAGCTGGGTCCGCCAGGCTCCAGGGAAGGGGCTGGAGTGGATCGGAGTCATTACTGGTCGTGATATCACATACTACGC
GAGCTGGGCGAAAGGCCGATTCACCATCTCCAAAACCTCGTCGACCACGGTGGATCTGAAAATGACCAGTCTGACAGCCGAGGACTCG
GCCACCTATTTCTGTGCCAGAGACGGTGGTTCTTCTGCTATTAATAGTAAGAACATTTGGGGCCAAGGCACCCTGGTCACCGTCTCGA
GC

SEQ ID NO: 23
480C8 CHIMERIC HEAVY CHAIN FULL-LENGTH AMINO ACID SEQUENCE. HUMAN GAMMA-1 CONSTANT
DOMAIN IS UNDERLINED
QSLEESGGRLVTPGTPLTLTCTVSGIDLSSNAMSWVRQAPGKGLEWIGVITGRDITYYASWAKGRFTISKTSSTTVDLKMTSLTAEDS
ATYFCARDGGSSAINSKNIWGQGTLVTVSS<u>ASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKRVEPKSCDKTHTCPPCPAPEAAGAPSVFLFPPKPKDTLMISRTPEVTCVV
VDVSHEDPEVKFNWYVDGVEVHNAKTKPREEQYNSTYRVVSVLTVLHQDWLNGKEYKCAVSNKALPAPIEKTISKAKGQPREPQVYTL
PPSRDELTKNQVSLTCLVKGFYPSDIAVEWESNGQPENNYKTTPPVLDSDGSFFLYSKLTVDKSRWQQGNVFSCSVMHEALHNHYTQK
SLSLSPG</u>

SEQUENCE LISTING

SEQ ID NO: 24
480C8 CHIMERIC HEAVY CHAIN VARIABLE HEAVY CHAIN AMINO ACID SEQUENCE. COMPLIMENTARITY
DETERMINING REGIONS ARE UNDERLINED
QSLEESGGRLVTPGTPLTLTCTVSGIDLS<u>SNAMS</u>WVRQAPGKGLEWIG<u>VITGRDITYYASWAKG</u>RFTISKTSSTTVDLKMTSLTAEDS
ATYFCAR<u>DGGSSAINSKNI</u>WGQGTLVTVSS

SEQ ID NO: 25
295E9 CHIMERIC LIGHT CHAIN FULL-LENGTH NUCLEOTIDE SEQUENCE
GATGTCGTGATGACCCAGACTCCAGCCTCCGTGGAGGCAGCTGTGGGAGGCACAGTCACAATCAATTGCCAAGCCAGTGAGAGCATTA
GCAGTTGGTTAGCCTGGTATCAGCAGAGACCAGGGCAGCCTCCCAAACTCCTGATCTACGAAGCATCCAAACTGGCGTCTGGGGTCCC
ATCGCGGTTCAAAGGCAGTGGATCTGGGACAGAGTTCACTCTCACCATCAGCGACCTGGAGTGTGCCGATGCTGCCACTTACTACTGT
CAAGGCTATTTTTATTTTATTAGTCGTAGTTATGTAAATGCTTTCGGCGGAGGGACCGAGGTGGTGGTCAAACGTACGGTGGCTGCAC
CATCTGTCTTCATCTTCCCGCCATCTGATGAGCAGTTGAAATCTGGAACTGCCTCTGTTGTGTGCCTGCTGAATAACTTCTATCCCAG
AGAGGCCAAAGTACAGTGGAAGGTGGATAACGCCCTCCAATCGGGTAACTCCCAGGAGAGTGTCACAGAGCAGGACAGCAAGGACAGC
ACCTACAGCCTCAGCAGCACCCTGACGCTGAGCAAAGCAGACTACGAGAAACACAAAGTCTACGCCTGCGAAGTCACCCATCAGGGCC
TGAGCTCGCCCGTCACAAAGAGCTTCAACAGGGGAGAGTGT

SEQ ID NO: 26
295E9 CHIMERIC LIGHT CHAIN VARIABLE LIGHT CHAIN NUCLEOTIDE SEQUENCE
GATGTCGTGATGACCCAGACTCCAGCCTCCGTGGAGGCAGCTGTGGGAGGCACAGTCACAATCAATTGCCAAGCCAGTGAGAGCATTA
GCAGTTGGTTAGCCTGGTATCAGCAGAGACCAGGGCAGCCTCCCAAACTCCTGATCTACGAAGCATCCAAACTGGCGTCTGGGGTCCC
ATCGCGGTTCAAAGGCAGTGGATCTGGGACAGAGTTCACTCTCACCATCAGCGACCTGGAGTGTGCCGATGCTGCCACTTACTACTGT
CAAGGCTATTTTTATTTTATTAGTCGTAGTTATGTAAATGCTTTCGGCGGAGGGACCGAGGTGGTGGTCAAA

SEQ ID NO: 27
295E9 CHIMERIC LIGHT CHAIN FULL-LENGTH AMINO ACID SEQUENCE. HUMAN KAPPA CONSTANT
DOMAIN IS UNDERLINED
DVVMTQTPASVEAAVGGTVTINCQASESISSWLAWYQQRPGQPPKLLIYEASKLASGVPSRFKGSGSGTEFTLTISDLECADAATYYC
QGYFYFISRSYVNAFGGGTEVVVK<u>RTVAAPSVFIFPPSDEQLKSGTASVVCLLNNFYPREAKVQWKVDNALQSGNSQESVTEQDSKDS
TYSLSSTLTLSKADYEKHKVYACEVTHQGLSSPVTKSFNRGEC</u>

SEQ ID NO: 28
295E9 CHIMERIC LIGHT CHAIN VARIABLE LIGHT CHAIN AMINO ACID SEQUENCE. COMPIMENTARITY
DETERMINING REGIONS ARE UNDERLINED
DVVMTQTPASVEAAVGGTVTINC<u>QASESISSWLA</u>WYQQRPGQPPKLLIY<u>EASKLAS</u>GVPSRFKGSGSGTEFTLTISDLECADAATYYC
<u>QGYFYFISRSYVNA</u>FGGGTEVVVK

SEQ ID NO: 29
295E9 CHIMERIC HEAVY CHAIN FULL-LENGTH NUCLEOTIDE SEQUENCE
CAGTCACTGGAGGAGTCCGGGGGTCGCCTGGTCACGCCTGGGACACCCCTGACACTCACCTGCACAGTCTCTGGAATCGACCTCAGTA
GTAATGCAATGAGCTGGGTCCGCCAGGCTCCAGGGAAGGGGCTGGAGTGGATCGGAGTCATTACTGGTCGTGATATTAATTACTACGC
GAGCTGGGCGAAAGGCCGATTCACCATCTCCAAAACCTCGTCGACCACGGTGGATCTGAAAATGACCAGTCTGACAGCCGAGGACTCG
GCCACCTATTTCTGTGCCAGAGACGGTGGTTCTTCTGCTATTACTAGTAAGAACATTTGGGGCCCAGGCACCCTGGTCACCGTCTCGA
GCGCTAGCACCAAGGGCCCATCGGTCTTCCCCCTGGCACCCTCCTCCAAGAGCACCTCTGGGGGCACAGCGGCCCTGGGCTGCCTGGT
CAAGGACTACTTCCCCGAACCGGTGACGGTGTCGTGGAACTCAGGCGCCCTGACCAGCGGCGTGCACACCTTCCCGGCTGTCCTACAG
TCCTCAGGACTCTACTCCCTCAGCAGCGTGGTGACCGTGCCCTCCAGCAGCTTGGGCACCCAGACCTACATCTGCAACGTGAATCACA
AGCCCAGCAACACCAAGGTGGACAAGAGAGTTGAGCCCAAATCTTGTGACAAAACTCACACATGCCCACCGTGCCCAGCACCTGAAGC
CGCGGGGGCACCGTCAGTCTTCCTCTTCCCCCCAAAACCCAAGGACACCCTCATGATCTCCCGGACCCCTGAGGTCACATGCGTGGTG
GTGGACGTGAGCCACGAAGACCCTGAGGTCAAGTTCAACTGGTACGTGGACGGCGTGGAGGTGCATAATGCCAAGACAAAGCCGCGGG
AGGAGCAGTACAACAGCACGTACCGTGTGGTCAGCGTCCTCACCGTCCTGCACCAGGACTGGCTGAATGGCAAGGAGTACAAGTGCGC
GGTCTCCAACAAAGCCCTCCCAGCCCCCATCGAGAAAACCATCTCCAAAGCCAAAGGGCAGCCCCGAGAACCACAGGTGTACACCCTG
CCCCCATCCCGGGATGAGCTGACCAAGAACCAGGTCAGCCTGACCTGCCTGGTCAAAGGCTTCTATCCCAGCGACATCGCCGTGGAGT
GGGAGAGCAATGGGCAGCCGGAGAACAACTACAAGACCACGCCTCCCGTGCTGGACTCCGACGGCTCCTTCTTCCTCTATAGCAAGCT
CACCGTGGACAAGAGCAGGTGGCAGCAGGGGAACGTCTTCTCATGCTCCGTGATGCATGAGGCTCTGCACAACCACTACACGCAGAAG
AGCCTCTCCCTGTCTCCGGGT

SEQ ID NO: 30
295E9 CHIMERIC HEAVY CHAIN VARIABLE HEAVY CHAIN NUCLEOTIDE SEQUENCE
CAGTCACTGGAGGAGTCCGGGGGTCGCCTGGTCACGCCTGGGACACCCCTGACACTCACCTGCACAGTCTCTGGAATCGACCTCAGTA
GTAATGCAATGAGCTGGGTCCGCCAGGCTCCAGGGAAGGGGCTGGAGTGGATCGGAGTCATTACTGGTCGTGATATTAATTACTACGC
GAGCTGGGCGAAAGGCCGATTCACCATCTCCAAAACCTCGTCGACCACGGTGGATCTGAAAATGACCAGTCTGACAGCCGAGGACTCG
GCCACCTATTTCTGTGCCAGAGACGGTGGTTCTTCTGCTATTACTAGTAAGAACATTTGGGGCCCAGGCACCCTGGTCACCGTCTCGA
GC

SEQ ID NO: 31
295E9 CHIMERIC HEAVY CHAIN FULL-LENGTH AMINO ACID SEQUENCE. HUMAN GAMMA-1 CONSTANT
DOMAIN IS UNDERLINED
QSLEESGGRLVTPGTPLTLTCTVSGIDLSSNAMSWVRQAPGKGLEWIGVITGRDINYYASWAKGRFTISKTSSTTVDLKMTSLTAEDS
ATYFCARDGGSSAITSKNIWGPGTLVTVSS<u>ASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKRVEPKSCDKTHTCPPCPAPEAAGAPSVFLFPPKPKDTLMISRTPEVTCVV
VDVSHEDPEVKFNWYVDGVEVHNAKTKPREEQYNSTYRVVSVLTVLHQDWLNGKEYKCAVSNKALPAPIEKTISKAKGQPREPQVYTL
PPSRDELTKNQVSLTCLVKGFYPSDIAVEWESNGQPENNYKTTPPVLDSDGSFFLYSKLTVDKSRWQQGNVFSCSVMHEALHNHYTQK
SLSLSPG</u>

SEQUENCE LISTING

SEQ ID NO: 32
295E9 CHIMERIC HEAVY CHAIN VARIABLE HEAVY CHAIN AMINO ACID SEQUENCE. COMPLIMENTARITY
DETERMINING REGIONS ARE UNDERLINED
QSLEESGGRLVTPGTPLTLTCTVSGIDLS<u>SNAMS</u>WVRQAPGKGLEWIG<u>VITGRDINYYASWAKG</u>RFTISKTSSTTVDLKMTSLTAEDS
ATYFCAR<u>DGSSAITSKNI</u>WGPGTLVTVSS

SEQ ID NO: 33
480A7 CHIMERIC LIGHT CHAIN FULL-LENGTH NUCLEOTIDE SEQUENCE
GATGTCGTGATGACCCAGACTCCAGCCTCCGTGGAGGCAGCTGTGGGAGGCACAGTCACCATCAATTGCCAAGCCAGTGAGAGCATTA
GCAGTTGGTTAGCCTGGTATCAGCAGAGACCAGGGCAGCCTCCCAAGCTCCTGATCTACGAAGCATCCAAACTGGCATCTGGGGTCCC
ATCGCGGTTCAGTGGCAGTGGATCTGGGACAGAGTTCACTCTCACCATCAGCGACCTGGAGTGTGCCGATGCTGCCACTTACTACTGT
CAGGGCTATTTTTATTTTATTAGTCGTAGTTATGTAAATGCTTTCGGCGGAGGGACCGAGGTGGTGTTCAAACGTACGGTGGCTGCAC
CATCTGTCTTCATCTTCCCGCCATCTGATGAGCAGTTGAAATCTGGAACTGCCTCTGTTGTGTGCCTGCTGAATAACTTCTATCCCAG
AGAGGCCAAAGTACAGTGGAAGGTGGATAACGCCCTCCAATCGGGTAACTCCCAGGAGAGTGTCACAGAGCAGGACAGCAAGGACAGC
ACCTACAGCCTCAGCAGCACCCTGACGCTGAGCAAAGCAGACTACGAGAAACACAAAGTCTACGCCTGCGAAGTCACCCATCAGGGCC
TGAGCTCGCCCGTCACAAAGAGCTTCAACAGGGGAGAGTGT

SEQ ID NO: 34
480A7 CHIMERIC LIGHT CHAIN VARIABLE LIGHT CHAIN NUCLEOTIDE SEQUENCE
GATGTCGTGATGACCCAGACTCCAGCCTCCGTGGAGGCAGCTGTGGGAGGCACAGTCACCATCAATTGCCAAGCCAGTGAGAGCATTA
GCAGTTGGTTAGCCTGGTATCAGCAGAGACCAGGGCAGCCTCCCAAGCTCCTGATCTACGAAGCATCCAAACTGGCATCTGGGGTCCC
ATCGCGGTTCAGTGGCAGTGGATCTGGGACAGAGTTCACTCTCACCATCAGCGACCTGGAGTGTGCCGATGCTGCCACTTACTACTGT
CAGGGCTATTTTTATTTTATTAGTCGTAGTTATGTAAATGCTTTCGGCGGAGGGACCGAGGTGGTGTTCAAA

SEQ ID NO: 35
480A7 CHIMERIC LIGHT CHAIN FULL-LENGTH AMINO ACID SEQUENCE. HUMAN KAPPA CONSTANT
DOMAIN IS UNDERLINED
DVVMTQTPASVEAAVGGTVTINCQASESISSWLAWYQQRPGQPPKLLIYEASKLASGVPSRFSGSGSGTEFTLTISDLECADAATYYC
QGYFYFISRSYVNAFGGGTEVVFK<u>RTVAAPSVFIFPPSDEQLKSGTASVVCLLNNFYPREAKVQWKVDNALQSGNSQESVTEQDSKDS</u>
<u>TYSLSSTLTLSKADYEKHKVYACEVTHQGLSSPVTKSFNRGEC</u>

SEQ ID NO: 36
480A7 CHIMERIC LIGHT CHAIN VARIABLE LIGHT CHAIN AMINO ACID SEQUENCE. COMPLIMENTARITY
DETERMINING REGIONS ARE UNDERLINED
DVVMTQTPASVEAAVGGTVTINC<u>QASESISSWLA</u>WYQQRPGQPPKLLIY<u>EASKLAS</u>GVPSRFSGSGSGTEFTLTISDLECADAATYYC
<u>QGYFYFISRSYVNA</u>FGGGTEVVFK

SEQ ID NO: 37
480A7 CHIMERIC HEAVY CHAIN FULL-LENGTH NUCLEOTIDE SEQUENCE
CAGTCGCTGGAGGAGTCCGGGGGTCGCCTGGTCACGCCTGGGACACCCCTGACACTCACCTGCACAGTCTCTGGAATCGACCTCAGTA
GCAATGCAATGAGCTGGGTCCGCCAGGCTCCAGGGAAGGGGCTGGAGTGGATCGGAGTCATTACTGGTCGTGATATCACATACTACGC
GAGCTGGGCGAAAGGCCGATTCACCATCTCCAAAACCTCGTCGACCACGGTGGATCTGAAAATGACCAGTCTGACAGCCGAGGACTCG
GCCACCTATTTCTGTGCCAGAGACGGTGGTTCTTCTGCTATTACTAGTAAGAACATTTGGGGCCCGGGCACCCTGGTCACCGTCTCGA
GCGCTAGCACCAAGGGCCCATCGGTCTTCCCCCTGGCACCCTCCTCCAAGAGCACCTCTGGGGGCACAGCGGCCCTGGGCTGCCTGGT
CAAGGACTACTTCCCCGAACCGGTGACGGTGTCGTGGAACTCAGGCGCCCTGACCAGCGGCGTGCACACCTTCCCGGCTGTCCTACAG
TCCTCAGGACTCTACTCCCTCAGCAGCGTGGTGACCGTGCCCTCCAGCAGCTTGGGCACCCAGACCTACATCTGCAACGTGAATCACA
AGCCCAGCAACACCAAGGTGGACAAGAGAGTTGAGCCCAAATCTTGTGACAAAACTCACACATGCCCACCGTGCCCAGCACCTGAAGC
CGCGGGGGCACCGTCAGTCTTCCTCTTCCCCCCAAAACCCAAGGACACCCTCATGATCTCCCGGACCCCTGAGGTCACATGCGTGGTG
GTGGACGTGAGCCACGAAGACCCTGAGGTCAAGTTCAACTGGTACGTGGACGGCGTGGAGGTGCATAATGCCAAGACAAAGCCGCGGG
AGGAGCAGTACAACAGCACGTACCGTGTGGTCAGCGTCCTCACCGTCCTGCACCAGGACTGGCTGAATGGCAAGGAGTACAAGTGCGC
GGTCTCCAACAAAGCCCTCCCAGCCCCCATCGAGAAAACCATCTCCAAAGCCAAAGGGCAGCCCCGAGAACCACAGGTGTACACCCTG
CCCCCATCCCGGGATGAGCTGACCAAGAACCAGGTCAGCCTGACCTGCCTGGTCAAAGGCTTCTATCCCAGCGACATCGCCGTGGAGT
GGGAGAGCAATGGGCAGCCGGAGAACAACTACAAGACCACGCCTCCCGTGCTGGACTCCGACGGCTCCTTCTTCCTCTATAGCAAGCT
CACCGTGGACAAGAGCAGGTGGCAGCAGGGGAACGTCTTCTCATGCTCCGTGATGCATGAGGCTCTGCACAACCACTACACGCAGAAG
AGCCTCTCCCTGTCTCCGGGT

SEQ ID NO: 38
480A7 CHIMERIC HEAVY CHAIN VARIABLE HEAVY CHAIN NUCLEOTIDE SEQUENCE
CAGTCGCTGGAGGAGTCCGGGGGTCGCCTGGTCACGCCTGGGACACCCCTGACACTCACCTGCACAGTCTCTGGAATCGACCTCAGTA
GCAATGCAATGAGCTGGGTCCGCCAGGCTCCAGGGAAGGGGCTGGAGTGGATCGGAGTCATTACTGGTCGTGATATCACATACTACGC
GAGCTGGGCGAAAGGCCGATTCACCATCTCCAAAACCTCGTCGACCACGGTGGATCTGAAAATGACCAGTCTGACAGCCGAGGACTCG
GCCACCTATTTCTGTGCCAGAGACGGTGGTTCTTCTGCTATTACTAGTAAGAACATTTGGGGCCCGGGCACCCTGGTCACCGTCTCGA
GC

SEQ ID NO: 39
480A7 CHIMERIC HEAVY CHAIN FULL-LENGTH AMINO ACID SEQUENCE. HUMAN GAMMA-1 CONSTANT
DOMAIN IS UNDERLINED
QSLEESGGRLVTPGTPLTLTCTVSGIDLSSNAMSWVRQAPGKGLEWIGVITGRDITYYASWAKGRFTISKTSSTTVDLKMTSLTAEDS
ATYFCARDGSSAITSKNIWGPGTLVTVSS<u>ASTKGPSVFPLAPSSKSTSGGTAALGCLVKDYFPEPVTVSWNSGALTSGVHTFPAVLQ</u>
<u>SSGLYSLSSVVTVPSSSLGTQTYICNVNHKPSNTKVDKRVEPKSCDKTHTCPPCPAPEAAGAPSVFLFPPKPKDTLMISRTPEVTCVV</u>
<u>VDVSHEDPEVKFNWYVDGVEVHNAKTKPREEQYNSTYRVVSVLTVLHQDWLNGKEYKCAVSNKALPAPIEKTISKAKGQPREPQVYTL</u>
<u>PPSRDELTKNQVSLTCLVKGFYPSDIAVEWESNGQPENNYKTTPPVLDSDGSFFLYSKLTVDKSRWQQGNVFSCSVMHEALHNHYTQK</u>
<u>SLSLSPG</u>

SEQUENCE LISTING

SEQ ID NO: 40
480A7 CHIMERIC HEAVY CHAIN VARIABLE HEAVY CHAIN AMINO ACID SEQUENCE. COMPLIMENTARITY
DETERMINING REGIONS ARE UNDERLINED
QSLEESGGRLVTPGTPLTLTCTVSGIDLS<u>SNAMS</u>WVRQAPGKGLEWIG<u>VITGRDITYYASWAKG</u>RFTISKTSSTTVDLKMTSLTAEDS
ATYFCAR<u>DGGSSAITSKNI</u>WGPGTLVTVSS

SEQ ID NO: 41
485H6 CHIMERIC LIGHT CHAIN FULL-LENGTH NUCLEOTIDE SEQUENCE
GATGTCGTGATGACCCAGACTCCAGCCTCCGTGTCTGAACCTGTGGGAGGCACAGTCACCATCAAGTGCCAGGCCAGTGAGAGCATTA
ATAGTAATGTAGCCTGGTATCAGCAGAAACCAGGGCAGCGTCCCAAGCTCCTGATCTATGATTCATCCACTCTGGAATCTGGGGTCCC
ATCGCGGTTCAAAGGCAGTAGATCTGGGACAGAGTTCACTCTCACCATCAGCGACCTGGAGTGTGCCGATGCCGCCACTTACTACTGT
CAATGTAGTAGTTATGGTAGTAGTTATGTTGGTGGTTTCGGCGGAGGGACCGAGGTGGTGTTCAAACGTACGGTGGCTGCACCATCTG
TCTTCATCTTCCCGCCATCTGATGAGCAGTTGAAATCTGGAACTGCCTCTGTTGTGTGCCTGCTGAATAACTTCTATCCCAGAGAGGC
CAAAGTACAGTGGAAGGTGGATAACGCCCTCCAATCGGGTAACTCCCAGGAGAGTGTCACAGAGCAGGACAGCAAGGACAGCACCTAC
AGCCTCAGCAGCACCCTGACGCTGAGCAAAGCAGACTACGAGAAACACAAAGTCTACGCCTGCGAAGTCACCCATCAGGGCCTGAGCT
CGCCCGTCACAAAGAGCTTCAACAGGGGAGAGTGT

SEQ ID NO: 42
485H6 CHIMERIC LIGHT CHAIN VARIABLE LIGHT CHAIN NUCLEOTIDE SEQUENCE
GATGTCGTGATGACCCAGACTCCAGCCTCCGTGTCTGAACCTGTGGGAGGCACAGTCACCATCAAGTGCCAGGCCAGTGAGAGCATTA
ATAGTAATGTAGCCTGGTATCAGCAGAAACCAGGGCAGCGTCCCAAGCTCCTGATCTATGATTCATCCACTCTGGAATCTGGGGTCCC
ATCGCGGTTCAAAGGCAGTAGATCTGGGACAGAGTTCACTCTCACCATCAGCGACCTGGAGTGTGCCGATGCCGCCACTTACTACTGT
CAATGTAGTAGTTATGGTAGTAGTTATGTTGGTGGTTTCGGCGGAGGGACCGAGGTGGTGTTCAAA

SEQ ID NO: 43
485H6 CHIMERIC LIGHT CHAIN FULL-LENGTH AMINO ACID SEQUENCE. HUMAN KAPPA CONSTANT
DOMAIN IS UNDERLINED
DVVMTQTPASVSEPVGGTVTIKCQASESINSNVAWYQQKPGQRPKLLIYDSSTLESGVPSRFKGSRSGTEFTLTISDLECADAATYYC
QCSSYGSSYVGGFGGGTEVVFK<u>RTVAAPSVFIFPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC</u>

SEQ ID NO: 44
485H6 CHIMERIC LIGHT CHAIN VARIABLE LIGHT CHAIN AMINO ACID SEQUENCE. COMPLIMENTARITY
DETERMINING REGIONS ARE UNDERLINED
DVVMTQTPASVSEPVGGTVTIKC<u>QASESINSNVA</u>WYQQKPGQRPKLLIY<u>DSSTLES</u>GVPSRFKGSRSGTEFTLTISDLECADAATYYC
<u>QCSSYGSSYVGG</u>FGGGTEVVFK

SEQ ID NO: 45
485H6 CHIMERIC HEAVY CHAIN FULL-LENGTH NUCLEOTIDE SEQUENCE
CAGTCGCTGGAGGAGTCCGGGGGTCGCCTGGTCACGCCTGGGACACCCCTGACACTCACCTGCACAGTCTCTGGAATCGACCTCAGTA
GCAATGCAATGAGCTGGGTCCGCCAGGCTCCAGGGAAGGGGCTGGAGTGGATCGGAGTCATTACTGGTCGTGATATCACATACTACGC
GAGCTGGGCGAAAGGCCGATTCACCATCTCCAAAACCTCGTCGACCACGGTGGATCTGAAAATGCCCAGTCTGACAGCCGAGGACTCG
GCCACCTATTTCTGTGCCAGAGACGGTGGTTCTTCTGCTATTACTAGTAAGAACATTTGGGGCCAGGGGACCCTCGTCACCGTCTCGA
GCGCTAGCACCAAGGGCCCATCGGTCTTCCCCCTGGCACCCTCCTCCAAGAGCACCTCTGGGGGCACAGCGGCCCTGGGCTGCCTGGT
CAAGGACTACTTCCCCGAACCGGTGACGGTGTCGTGGAACTCAGGCGCCCTGACCAGCGGCGTGCACACCTTCCCGGCTGTCCTACAG
TCCTCAGGACTCTACTCCCTCAGCAGCGTGGTGACCGTGCCCTCCAGCAGCTTGGGCACCCAGACCTACATCTGCAACGTGAATCACA
AGCCCAGCAACACCAAGGTGGACAAGAGAGTTGAGCCCAAATCTTGTGACAAAACTCACACATGCCCACCGTGCCCAGCACCTGAAGC
CGCGGGGGCACCGTCAGTCTTCCTCTTCCCCCCAAAACCCAAGGACACCCTCATGATCTCCCGGACCCCTGAGGTCACATGCGTGGTG
GTGGACGTGAGCCACGAAGACCCTGAGGTCAAGTTCAACTGGTACGTGGACGGCGTGGAGGTGCATAATGCCAAGACAAAGCCGCGGG
AGGAGCAGTACAACAGCACGTACCGTGTGGTCAGCGTCCTCACCGTCCTGCACCAGGACTGGCTGAATGGCAAGGAGTACAAGTGCGC
GGTCTCCAACAAAGCCCTCCCAGCCCCCATCGAGAAAACCATCTCCAAAGCCAAAGGGCAGCCCCGAGAACCACAGGTGTACACCCTG
CCCCCATCCCGGGATGAGCTGACCAAGAACCAGGTCAGCCTGACCTGCCTGGTCAAAGGCTTCTATCCCAGCGACATCGCCGTGGAGT
GGGAGAGCAATGGGCAGCCGGAGAACAACTACAAGACCACGCCTCCCGTGCTGGACTCCGACGGCTCCTTCTTCCTCTATAGCAAGCT
CACCGTGGACAAGAGCAGGTGGCAGCAGGGGAACGTCTTCTCATGCTCCGTGATGCATGAGGCTCTGCACAACCACTACACGCAGAAG
AGCCTCTCCCTGTCTCCGGGT

SEQ ID NO: 46
485H6 CHIMERIC HEAVY CHAIN VARIABLE HEAVY CHAIN NUCLEOTIDE SEQUENCE
CAGTCGCTGGAGGAGTCCGGGGGTCGCCTGGTCACGCCTGGGACACCCCTGACACTCACCTGCACAGTCTCTGGAATCGACCTCAGTA
GCAATGCAATGAGCTGGGTCCGCCAGGCTCCAGGGAAGGGGCTGGAGTGGATCGGAGTCATTACTGGTCGTGATATCACATACTACGC
GAGCTGGGCGAAAGGCCGATTCACCATCTCCAAAACCTCGTCGACCACGGTGGATCTGAAAATGCCCAGTCTGACAGCCGAGGACTCG
GCCACCTATTTCTGTGCCAGAGACGGTGGTTCTTCTGCTATTACTAGTAAGAACATTTGGGGCCAGGGGACCCTCGTCACCGTCTCGA
GC

SEQ ID NO: 47
485H6 CHIMERIC HEAVY CHAIN FULL-LENGTH AMINO ACID SEQUENCE. HUMAN GAMMA-1 CONSTANT
DOMAIN IS UNDERLINED
QSLEESGGRLVTPGTPLTLTCTVSGIDLSSNAMSWVRQAPGKGLEWIGVITGRDITYYASWAKGRFTISKTSSTTVDLKMPSLTAEDS
ATYFCARDGGSSAITSKNIWGQGTLVTVSS<u>ASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKRVEPKSCDKTHTCPPCPAPEAAGAPSVFLFPPKPKDTLMISRTPEVTCVV
VDVSHEDPEVKFNWYVDGVEVHNAKTKPREEQYNSTYRVVSVLTVLHQDWLNGKEYKCAVSNKALPAPIEKTISKAKGQPREPQVYTL
PPSRDELTKNQVSLTCLVKGFYPSDIAVEWESNGQPENNYKTTPPVLDSDGSFFLYSKLTVDKSRWQQGNVFSCSVMHEALHNHYTQK
SLSLSPG</u>

SEQUENCE LISTING

SEQ ID NO: 48
485H6 CHIMERIC HEAVY CHAIN VARIABLE HEAVY CHAIN AMINO ACID SEQUENCE. COMPLIMENTARITY
DETERMINING REGIONS ARE UNDERLINED
QSLEESGGRLVTPGTPLTLTCTVSGIDLS<u>SNAMS</u>WVRQAPGKGLEWIG<u>VITGRDITYYASWAKG</u>RFTISKTSSTTVDLKMPSLTAEDS
ATYFCAR<u>DGSSAITSKNI</u>WGQGTLVTVSS

SEQ ID NO: 49
284A10 HUMANIZED LIGHT CHAIN FULL-LENGTH NUCLEOTIDE SEQUENCE
GACGTCGTGATGACCCAGTCTCCTTCCACCCTGTCTGCATCTGTAGGAGACAGAGTCACCATCAATTGCCAAGCCAGTGAGAGCATTA
GCAGTTGGTTAGCCTGGTATCAGCAGAAACCAGGGAAAGCCCCTAAGCTCCTGATCTATGAAGCATCCAAACTGGCATCTGGGGTCCC
ATCAAGGTTCAGCGGCAGTGGATCTGGGACAGAATTCACTCTCACCATCAGCAGCCTGCAGCCTGATGATTTTGCAACTTATTACTGC
CAAGGCTATTTTTATTTTATTAGTCGTACTTATGTAAATTCTTTCGGCGGAGGGACCAAGGTGGAGATCAAACGTACGGTGGCTGCAC
CATCTGTCTTCATCTTCCCGCCATCTGATGAGCAGTTGAAATCTGGAACTGCCTCTGTTGTGTGCCTGCTGAATAACTTCTATCCCAG
AGAGGCCAAAGTACAGTGGAAGGTGGATAACGCCCTCCAATCGGGTAACTCCCAGGAGAGTGTCACAGAGCAGGACAGCAAGGACAGC
ACCTACAGCCTCAGCAGCACCCTGACGCTGAGCAAAGCAGACTACGAGAAACACAAAGTCTACGCCTGCGAAGTCACCCATCAGGGCC
TGAGCTCGCCCGTCACAAAGAGCTTCAACAGGGGAGAGTGT

SEQ ID NO: 50
284A10 HUMANIZED LIGHT CHAIN VARIABLE LIGHT CHAIN NUCLEOTIDE SEQUENCE
GACGTCGTGATGACCCAGTCTCCTTCCACCCTGTCTGCATCTGTAGGAGACAGAGTCACCATCAATTGCCAAGCCAGTGAGAGCATTA
GCAGTTGGTTAGCCTGGTATCAGCAGAAACCAGGGAAAGCCCCTAAGCTCCTGATCTATGAAGCATCCAAACTGGCATCTGGGGTCCC
ATCAAGGTTCAGCGGCAGTGGATCTGGGACAGAATTCACTCTCACCATCAGCAGCCTGCAGCCTGATGATTTTGCAACTTATTACTGC
CAAGGCTATTTTTATTTTATTAGTCGTACTTATGTAAATTCTTTCGGCGGAGGGACCAAGGTGGAGATCAAA

SEQ ID NO: 51
284A10 HUMANIZED LIGHT CHAIN FULL-LENGTH AMINO ACID SEQUENCE. HUMAN KAPPA CONSTANT
DOMAIN IS UNDERLINED
DVVMTQSPSTLSASVGDRVTINCQASESISSWLAWYQQKPGKAPKLLIYEASKLASGVPSRFSGSGSGTEFTLTISSLQPDDFATYYC
QGYFYFISRTYVNSFGGGTKVEIK<u>RTVAAPSVFIFPPSDEQLKSGTASVVCLLNNFYPREAKVQWKVDNALQSGNSQESVTEQDSKDS
TYSLSSTLTLSKADYEKHKVYACEVTHQGLSSPVTKSFNRGEC</u>

SEQ ID NO: 52
284A10 HUMANIZED LIGHT CHAIN VARIABLE LIGHT CHAIN AMINO ACID SEQUENCE.
COMPIMENTARITY DETERMINING REGIONS ARE UNDERLINED
DVVMTQSPSTLSASVGDRVTINC<u>QASESISSWLA</u>WYQQKPGKAPKLLIY<u>EASKLAS</u>GVPSRFSGSGSGTEFTLTISSLQPDDFATYYC
<u>QGYFYFISRTYVNS</u>EGGGTKVEIK

SEQ ID NO: 53
284A10 HUMANIZED HEAVY CHAIN FULL-LENGTH NUCLEOTIDE SEQUENCE
GAGGTGCAGCTGGTGGAGTCTGGGGGAGGCTTGGTCCAGCCTGGGGGGTCCCTGAGACTCTCCTGTGCAGCCTCTGGATTCACCATCA
GTACCAATGCAATGAGCTGGGTCCGCCAGGCTCCAGGGAAGGGGCTGGAGTGGATCGGAGTCATTACTGGTCGTGATATCACATACTA
CGCGAGCTGGGCGAAAGGCAGATTCACCATCTCCAGAGACAATTCCAAGAACACGCTGTATCTTCAAATGAACAGCCTGAGAGCCGAG
GACACGGCTGTGTATTACTGTGCGAGAGACGGTGGTTCTTCTGCTATTACTAGTAACAACATTTGGGGCCAGGGAACCCTGGTCACCG
TCTCGAGCGCTAGCACCAAGGGCCCATCGGTCTTCCCCCTGGCACCCTCCTCCAAGAGCACCTCTGGGGGCACAGCGGCCCTGGGCTG
CCTGGTCAAGGACTACTTCCCCGAACCGGTGACGGTGTCGTGGAACTCAGGCGCCCTGACCAGCGGCGTGCACACCTTCCCGGCTGTC
CTACAGTCCTCAGGACTCTACTCCCTCAGCAGCGTGGTGACCGTGCCCTCCAGCAGCTTGGGCACCCAGACCTACATCTGCAACGTGA
ATCACAAGCCCAGCAACACCAAGGTGGACAAGAGAGTTGAGCCCAAATCTTGTGACAAAACTCACACATGCCCACCGTGCCCAGCACC
TGAAGCCGCGGGGGCACCGTCAGTCTTCCTCTTCCCCCCAAAACCCAAGGACACCCTCATGATCTCCCGGACCCCTGAGGTCACATGC
GTGGTGGTGGACGTGAGCCACGAAGACCCTGAGGTCAAGTTCAACTGGTACGTGGACGGCGTGGAGGTGCATAATGCCAAGACAAAGC
CGCGGGAGGAGCAGTACAACAGCACGTACCGTGTGGTCAGCGTCCTCACCGTCCTGCACCAGGACTGGCTGAATGGCAAGGAGTACAA
GTGCGCGGTCTCCAACAAAGCCCTCCCAGCCCCCATCGAGAAAACCATCTCCAAAGCCAAAGGGCAGCCCCGAGAACCACAGGTGTAC
ACCCTGCCCCCATCCCGGGATGAGCTGACCAAGAACCAGGTCAGCCTGACCTGCCTGGTCAAAGGCTTCTATCCCAGCGACATCGCCG
TGGAGTGGGAGAGCAATGGGCAGCCGGAGAACAACTACAAGACCACGCCTCCCGTGCTGGACTCCGACGGCTCCTTCTTCCTCTATAG
CAAGCTCACCGTGGACAAGAGCAGGTGGCAGCAGGGGAACGTCTTCTCATGCTCCGTGATGCATGAGGCTCTGCACAACCACTACACG
CAGAAGAGCCTCTCCCTGTCTCCGGGT

SEQ ID NO: 54
284A10 HUMANIZED HEAVY CHAIN VARIABLE HEAVY CHAIN NUCLEOTIDE SEQUENCE
GAGGTGCAGCTGGTGGAGTCTGGGGGAGGCTTGGTCCAGCCTGGGGGGTCCCTGAGACTCTCCTGTGCAGCCTCTGGATTCACCATCA
GTACCAATGCAATGAGCTGGGTCCGCCAGGCTCCAGGGAAGGGGCTGGAGTGGATCGGAGTCATTACTGGTCGTGATATCACATACTA
CGCGAGCTGGGCGAAAGGCAGATTCACCATCTCCAGAGACAATTCCAAGAACACGCTGTATCTTCAAATGAACAGCCTGAGAGCCGAG
GACACGGCTGTGTATTACTGTGCGAGAGACGGTGGTTCTTCTGCTATTACTAGTAACAACATTTGGGGCCAGGGAACCCTGGTCACCG
TCTCGAGC

SEQ ID NO: 55
284A10 HUMANIZED HEAVY CHAIN FULL-LENGTH AMINO ACID SEQUENCE. HUMAN GAMMA-1
CONSTANT DOMAIN ISUNDERLINED
EVQLVESGGGLVQPGGSLRLSCAASGFTISTNAMSWVRQAPGKGLEWIGVITGRDITYYASWAKGRFTISRDNSKNTLYLQMNSLRAE
DTAVYYCARDGGSSAITSNNIWGQGTLVTVSS<u>ASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKRVEPKSCDKTHTCPPCPAPEAAGAPSVFLFPPKPKDTLMISRTPEVTC
VVVDVSHEDPEVKFNWYVDGVEVHNAKTKPREEQYNSTYRVVSVLTVLHQDWLNGKEYKCAVSNKALPAPIEKTISKAKGQPREPQVY
TLPPSRDELTKNQVSLTCLVKGFYPSDIAVEWESNGQPENNYKTTPPVLDSDGSFFLYSKLTVDKSRWQQGNVFSCSVMHEALHNHYT
QKSLSLSPG</u>

SEQUENCE LISTING

SEQ ID NO: 56
284A10 HUMANIZED HEAVY CHAIN VARIABLE HEAVY CHAIN AMINO ACID SEQUENCE.
COMPLIMENTARITY DETERMINING REGIONS ARE UNDERLINED
EVQLVESGGGLVQPGGSLRLSCAASGFTIS<u>TNAMS</u>WVRQAPGKGLEWIG<u>VITGRDITYYASWAKG</u>RFTISRDNSKNTLYLQMNSLRAE
DTAVYYCARD<u>GGSSAITSNNI</u>WGQGTLVTVSS

SEQ ID NO: 57
299F6 HUMANIZED LIGHT CHAIN FULL-LENGTH NUCLEOTIDE SEQUENCE
GACATCCAGATGACCCAGTCTCCTTCCACCCTGTCTGCATCTGTAGGAGACAGAGTCACCATCACTTGCCAAGCCAGTGAGAGCATTA
GCAGTTGGTTAGCCTGGTATCAGCAGAAACCAGGGAAAGCCCCTAAGCTCCTGATCTATGAAGCATCCAAACTGGCATCTGGGGTCCC
ATCAAGGTTCAGCGGCAGTGGATCTGGGACAGAATTCACTCTCACCATCAGCAGCCTGCAGCCTGATGATTTTGCAACTTATTACTGC
CAAGGCTATTTTTATTTTATTAGTCGTAGTTATGTAAATGCTTTCGGCGGAGGGACCAAGGTGGAGATCAAACGTACGGTGGCTGCAC
CATCTGTCTTCATCTTCCCGCCATCTGATGAGCAGTTGAAATCTGGAACTGCCTCTGTTGTGTGCCTGCTGAATAACTTCTATCCCAG
AGAGGCCAAAGTACAGTGGAAGGTGGATAACGCCCTCCAATCGGGTAACTCCCAGGAGAGTGTCACAGAGCAGGACAGCAAGGACAGC
ACCTACAGCCTCAGCAGCACCCTGACGCTGAGCAAAGCAGACTACGAGAAACACAAAGTCTACGCCTGCGAAGTCACCCATCAGGGCC
TGAGCTCGCCCGTCACAAAGAGCTTCAACAGGGGAGAGTGT

SEQ ID NO: 58
299F6 HUMANIZED LIGHT CHAIN VARIABLE LIGHT CHAIN NUCLEOTIDE SEQUENCE
GACATCCAGATGACCCAGTCTCCTTCCACCCTGTCTGCATCTGTAGGAGACAGAGTCACCATCACTTGCCAAGCCAGTGAGAGCATTA
GCAGTTGGTTAGCCTGGTATCAGCAGAAACCAGGGAAAGCCCCTAAGCTCCTGATCTATGAAGCATCCAAACTGGCATCTGGGGTCCC
ATCAAGGTTCAGCGGCAGTGGATCTGGGACAGAATTCACTCTCACCATCAGCAGCCTGCAGCCTGATGATTTTGCAACTTATTACTGC
CAAGGCTATTTTTATTTTATTAGTCGTAGTTATGTAAATGCTTTCGGCGGAGGGACCAAGGTGGAGATCAAA

SEQ ID NO: 59
299F6 HUMANIZED LIGHT CHAIN FULL-LENGTH AMINO ACID SEQUENCE. HUMAN KAPPA CONSTANT
DOMAIN IS UNDERLINED
DIQMTQSPSTLSASVGDRVTITCQASESISSWLAWYQQKPGKAPKLLIYEASKLASGVPSRFSGSGSGTEFTLTISSLQPDDFATYYC
QGYFYFISRSYVNAFGGGTKVEIK<u>RTVAAPSVFIFPPSDEQLKSGTASVVCLLNNFYPREAKVQWKVDNALQSGNSQESVTEQDSKDS
TYSLSSTLTLSKADYEKHKVYACEVTHQGLSSPVTKSFNRGEC</u>

SEQ ID NO: 60
299F6 HUMANIZED LIGHT CHAIN VARIABLE LIGHT CHAIN AMINO ACID SEQUENCE. COMPIMENTARITY
DETERMINING REGIONS ARE UNDERLINED
DIQMTQSPSTLSASVGDRVTITC<u>QASESISSWLA</u>WYQQKPGKAPKLLIY<u>EASKLAS</u>GVPSRFSGSGSGTEFTLTISSLQPDDFATYYC
<u>QGYFYFISRSYVNA</u>FGGGTKVE1K

SEQ ID NO: 61
299F6 HUMANIZED HEAVY CHAIN FULL-LENGTH NUCLEOTIDE SEQUENCE
GAGGTGCAGCTGGTGGAGTCTGGGGGAGGCTTGGTCCAGCCTGGGGGGTCCCTGAGACTCTCCTGTGCAGCCTCTGGATTCACCATCA
GTAGCAATGCAATGAGCTGGGTCCGCCAGGCTCCAGGGAAGGGGCTGGAGTGGATCGGAGTCATTACTGGTCGTGATATCACATACTA
CGCGAACTGGGCGAAAGGCAGATTCACCATCTCCAGAGACAATTCCAAGAACACGCTGTATCTTCAAATGAACAGCCTGAGAGCCGAG
GACACGGCTGTGTATTACTGTGCGAGAGACGGTGGTTCTTCTGCTATTACTAGTAACAACATTTGGGGCCAGGGAACCCTGGTCACCG
TCTCGAGCGCTAGCACCAAGGGCCCATCGGTCTTCCCCCTGGCACCCTCCTCCAAGAGCACCTCTGGGGGCACAGCGGCCCTGGGCTG
CCTGGTCAAGGACTACTTCCCCGAACCGGTGACGGTGTCGTGGAACTCAGGCGCCCTGACCAGCGGCGTGCACACCTTCCCGGCTGTC
CTACAGTCCTCAGGACTCTACTCCCTCAGCAGCGTGGTGACCGTGCCCTCCAGCAGCTTGGGCACCCAGACCTACATCTGCAACGTGA
ATCACAAGCCCAGCAACACCAAGGTGGACAAGAGAGTTGAGCCCAAATCTTGTGACAAAACTCACACATGCCCACCGTGCCCAGCACC
TGAAGCCGCGGGGGCACCGTCAGTCTTCCTCTTCCCCCCAAAACCCAAGGACACCCTCATGATCTCCCGGACCCCTGAGGTCACATGC
GTGGTGGTGGACGTGAGCCACGAAGACCCTGAGGTCAAGTTCAACTGGTACGTGGACGGCGTGGAGGTGCATAATGCCAAGACAAAGC
CGCGGGAGGAGCAGTACAACAGCACGTACCGTGTGGTCAGCGTCCTCACCGTCCTGCACCAGGACTGGCTGAATGGCAAGGAGTACAA
GTGCGCGGTCTCCAACAAAGCCCTCCCAGCCCCCATCGAGAAAACCATCTCCAAAGCCAAAGGGCAGCCCCGAGAACCACAGGTGTAC
ACCCTGCCCCCATCCCGGGATGAGCTGACCAAGAACCAGGTCAGCCTGACCTGCCTGGTCAAAGGCTTCTATCCCAGCGACATCGCCG
TGGAGTGGGAGAGCAATGGGCAGCCGGAGAACAACTACAAGACCACGCCTCCCGTGCTGGACTCCGACGGCTCCTTCTTCCTCTATAG
CAAGCTCACCGTGGACAAGAGCAGGTGGCAGCAGGGGAACGTCTTCTCATGCTCCGTGATGCATGAGGCTCTGCACAACCACTACACG
CAGAAGAGCCTCTCCCTGTCTCCGGGT

SEQ ID NO: 62
299F6 HUMANIZED HEAVY CHAIN VARIABLE HEAVY CHAIN NUCLEOTIDE SEQUENCE
GAGGTGCAGCTGGTGGAGTCTGGGGGAGGCTTGGTCCAGCCTGGGGGGTCCCTGAGACTCTCCTGTGCAGCCTCTGGATTCACCATCA
GTAGCAATGCAATGAGCTGGGTCCGCCAGGCTCCAGGGAAGGGGCTGGAGTGGATCGGAGTCATTACTGGTCGTGATATCACATACTA
CGCGAACTGGGCGAAAGGCAGATTCACCATCTCCAGAGACAATTCCAAGAACACGCTGTATCTTCAAATGAACAGCCTGAGAGCCGAG
GACACGGCTGTGTATTACTGTGCGAGAGACGGTGGTTCTTCTGCTATTACTAGTAACAACATTTGGGGCCAGGGAACCCTGGTCACCG
TCTCGAGC

SEQ ID NO: 63
299F6 HUMANIZED HEAVY CHAIN FULL-LENGTH AMINO ACID SEQUENCE. HUMAN GAMMA-1
CONSTANT DOMAIN IS UNDERLINED
EVQLVESGGGLVQPGGSLRLSCAASGFTISSNAMSWVRQAPGKGLEWIGVITGRDITYYANWAKGRFTISRDNSKNTLYLQMNSLRAE
DTAVYYCARDGGSSAITSNNIWGQGTLVTVSS<u>ASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKRVEPKSCDKTHTCPPCPAPEAAGAPSVFLFPPKPKDTLMISRTPEVTC
VVVDVSHEDPEVKFNWYVDGVEVHNAKTKPREEQYNSTYRVVSVLTVLHQDWLNGKEYKCAVSNKALPAPIEKTISKAKGQPREPQVY
TLPPSRDELTKNQVSLTCLVKGFYPSDIAVEWESNGQPENNYKTTPPVLDSDGSFFLYSKLTVDKSRWQQGNVFSCSVMHEALHNHYT
QKSLSLSPG</u>

SEQUENCE LISTING

SEQ ID NO: 64
299F6 HUMANIZED HEAVY CHAIN VARIABLE HEAVY CHAIN AMINO ACID SEQUENCE.
COMPLIMENTARITY DETERMINING REGIONS ARE UNDERLINED
EVQLVESGGGLVQPGGSLRLSCAASGFTIS<u>SNAMS</u>WVRQAPGKGLEWIG<u>VITGRDITYYANWAKG</u>RFTISRDNSKNTLYLQMNSLRAE
DTAVYYCAR<u>DGSSAITSNNI</u>WGQGTLVTVSS

SEQ ID NO: 65
480C8 HUMANIZED LIGHT CHAIN FULL-LENGTH NUCLEOTIDE SEQUENCE
GACATCCAGATGACCCAGTCTCCTTCCACCCTGTCTGCATCTGTAGGAGACAGAGTCACCATCACTTGCCAAGCCAGTGAGAGCATTA
GCAGTTGGTTAGCCTGGTATCAGCAGAAACCAGGGAAAGCCCCTAAGCTCCTGATCTATGAAGCATCCAAACTGGCATCTGGGGTCCC
ATCAAGGTTCAGCGGCAGTGGATCTGGGACAGAATTCACTCTCACCATCAGCAGCCTGCAGCCTGATGATTTTGCAACTTATTACTGC
CAAGGCTATTTTTATTTTATTAGTCGTACTTATGTAAATGCTTTCGGCGGAGGGACCAAGGTGGAGATCAAACGTACGGTGGCTGCAC
CATCTGTCTTCATCTTCCCGCCATCTGATGAGCAGTTGAAATCTGGAACTGCCTCTGTTGTGTGCCTGCTGAATAACTTCTATCCCAG
AGAGGCCAAAGTACAGTGGAAGGTGGATAACGCCCTCCAATCGGGTAACTCCCAGGAGAGTGTCACAGAGCAGGACAGCAAGGACAGC
ACCTACAGCCTCAGCAGCACCCTGACGCTGAGCAAAGCAGACTACGAGAAACACAAAGTCTACGCCTGCGAAGTCACCCATCAGGGCC
TGAGCTCGCCCGTCACAAAGAGCTTCAACAGGGGAGAGTGT

SEQ ID NO: 66
480C8 HUMANIZED LIGHT CHAIN VARIABLE LIGHT CHAIN NUCLEOTIDE SEQUENCE
GACATCCAGATGACCCAGTCTCCTTCCACCCTGTCTGCATCTGTAGGAGACAGAGTCACCATCACTTGCCAAGCCAGTGAGAGCATTA
GCAGTTGGTTAGCCTGGTATCAGCAGAAACCAGGGAAAGCCCCTAAGCTCCTGATCTATGAAGCATCCAAACTGGCATCTGGGGTCCC
ATCAAGGTTCAGCGGCAGTGGATCTGGGACAGAATTCACTCTCACCATCAGCAGCCTGCAGCCTGATGATTTTGCAACTTATTACTGC
CAAGGCTATTTTTATTTTATTAGTCGTACTTATGTAAATGCTTTCGGCGGAGGGACCAAGGTGGAGATCAAA

SEQ ID NO: 67
480C8 HUMANIZED LIGHT CHAIN FULL-LENGTH AMINO ACID SEQUENCE. HUMAN KAPPA CONSTANT
DOMAIN IS UNDERLINED
DIQMTQSPSTLSASVGDRVTITCQASESISSWLAWYQQKPGKAPKLLIYEASKLASGVPSRFSGSGSGTEFTLTISSLQPDDFATYYC
QGYFYFISRTYVNAFGGGTKVEIK<u>RTVAAPSVFIFPPSDEQLKSGTASVVCLLNNFYPREAKVQWKVDNALQSGNSQESVTEQDSKDS
TYSLSSTLTLSKADYEKHKVYACEVTHQGLSSPVTKSFNRGEC</u>

SEQ ID NO: 68
480C8 HUMANIZED LIGHT CHAIN VARIABLE LIGHT CHAIN AMINO ACID SEQUENCE. COMPIMENTARITY
DETERMINING REGIONS ARE UNDERLINED
DIQMTQSPSTLSASVGDRVTITC<u>QASESISSWLA</u>WYQQKPGKAPKLLIY<u>EASKLAS</u>GVPSRFSGSGSGTEFTLTISSLQPDDFATYYC
<u>QGYFYFISRTYVNA</u>FGGGTKVE1K

SEQ ID NO: 69
480C8 HUMANIZED HEAVY CHAIN FULL-LENGTH NUCLEOTIDE SEQUENCE
GAGGTGCAGCTGGTGGAGTCTGGGGGAGGCTTGGTCCAGCCTGGGGGGTCCCTGAGACTCTCCTGTGCAGCCTCTGGAATCGACCTCA
GTAGCAATGCAATGAGCTGGGTCCGCCAGGCTCCAGGGAAGGGGCTGGAGTGGATCGGAGTCATTACTGGTCGTGATATCACATACTA
CGCGAGCTGGGCGAAAGGCAGATTCACCATCTCCAGAGACAATTCCAAGAACACGCTGTATCTTCAAATGAACAGCCTGAGAGCCGAG
GACACGGCTGTGTATTACTGTGCGAGAGACGGTGGTTCTTCTGCTATTAATAGTAAGAACATTTGGGGCCAGGGAACCCTGGTCACCG
TCTCGAGCGCTAGCACCAAGGGCCCATCGGTCTTCCCCCTGGCACCCTCCTCCAAGAGCACCTCTGGGGGCACAGCGGCCCTGGGCTG
CCTGGTCAAGGACTACTTCCCCGAACCGGTGACGGTGTCGTGGAACTCAGGCGCCCTGACCAGCGGCGTGCACACCTTCCCGGCTGTC
CTACAGTCCTCAGGACTCTACTCCCTCAGCAGCGTGGTGACCGTGCCCTCCAGCAGCTTGGGCACCCAGACCTACATCTGCAACGTGA
ATCACAAGCCCAGCAACACCAAGGTGGACAAGAGAGTTGAGCCCAAATCTTGTGACAAAACTCACACATGCCCACCGTGCCCAGCACC
TGAAGCCGCGGGGGCACCGTCAGTCTTCCTCTTCCCCCCAAAACCCAAGGACACCCTCATGATCTCCCGGACCCCTGAGGTCACATGC
GTGGTGGTGGACGTGAGCCACGAAGACCCTGAGGTCAAGTTCAACTGGTACGTGGACGGCGTGGAGGTGCATAATGCCAAGACAAAGC
CGCGGGAGGAGCAGTACAACAGCACGTACCGTGTGGTCAGCGTCCTCACCGTCCTGCACCAGGACTGGCTGAATGGCAAGGAGTACAA
GTGCGCGGTCTCCAACAAAGCCCTCCCAGCCCCCATCGAGAAAACCATCTCCAAAGCCAAAGGGCAGCCCCGAGAACCACAGGTGTAC
ACCCTGCCCCCATCCCGGGATGAGCTGACCAAGAACCAGGTCAGCCTGACCTGCCTGGTCAAAGGCTTCTATCCCAGCGACATCGCCG
TGGAGTGGGAGAGCAATGGGCAGCCGGAGAACAACTACAAGACCACGCCTCCCGTGCTGGACTCCGACGGCTCCTTCTTCCTCTATAG
CAAGCTCACCGTGGACAAGAGCAGGTGGCAGCAGGGGAACGTCTTCTCATGCTCCGTGATGCATGAGGCTCTGCACAACCACTACACG
CAGAAGAGCCTCTCCCTGTCTCCGGGT

SEQ ID NO: 70
480C8 HUMANIZED HEAVY CHAIN VARIABLE HEAVY CHAIN NUCLEOTIDE SEQUENCE
GAGGTGCAGCTGGTGGAGTCTGGGGGAGGCTTGGTCCAGCCTGGGGGGTCCCTGAGACTCTCCTGTGCAGCCTCTGGAATCGACCTCA
GTAGCAATGCAATGAGCTGGGTCCGCCAGGCTCCAGGGAAGGGGCTGGAGTGGATCGGAGTCATTACTGGTCGTGATATCACATACTA
CGCGAGCTGGGCGAAAGGCAGATTCACCATCTCCAGAGACAATTCCAAGAACACGCTGTATCTTCAAATGAACAGCCTGAGAGCCGAG
GACACGGCTGTGTATTACTGTGCGAGAGACGGTGGTTCTTCTGCTATTAATAGTAAGAACATTTGGGGCCAGGGAACCCTGGTCACCG
TCTCGAGC

SEQ ID NO: 71
480C8 HUMANIZED HEAVY CHAIN FULL-LENGTH AMINO ACID SEQUENCE. HUMAN GAMMA-1
CONSTANT DOMAIN IS UNDERLINED
EVQLVESGGGLVQPGGSLRLSCAASGIDLSSNAMSWVRQAPGKGLEWIGVITGRDITYYASWAKGRFTISRDNSKNTLYLQMNSLRAE
DTAVYYCARDGSSAINSKNIWGQGTLVTVSS<u>ASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKRVEPKSCDKTHTCPPCPAPEAAGAPSVFLFPPKPKDTLMISRTPEVTC
VVVDVSHEDPEVKFNWYVDGVEVHNAKTKPREEQYNSTYRVVSVLTVLHQDWLNGKEYKCAVSNKALPAPIEKTISKAKGQPREPQVY
TLPPSRDELTKNQVSLTCLVKGFYPSDIAVEWESNGQPENNYKTTPPVLDSDGSFFLYSKLTVDKSRWQQGNVFSCSVMHEALHNHYT
QKSLSLSPG</u>

SEQUENCE LISTING

SEQ ID NO: 72
480C8 HUMANIZED HEAVY CHAIN VARIABLE HEAVY CHAIN AMINO ACID SEQUENCE.
COMPLIMENTARITY DETERMINING REGIONS ARE UNDERLINED
EVQLVESGGGLVQPGGSLRLSCAASGIDLS<u>SNAMS</u>WVRQAPGKGLEWIG<u>VITGRDITYYASWAKG</u>RFTISRDNSKNTLYLQMNSLRAE
DTAVYYCAR<u>DGGSSAINSKNI</u>WGQGTLVTVSS

What is claimed is:

1. An isolated monoclonal antibody (mAb) or antigen-binding fragment thereof having a binding specificity to human CD3, wherein the isolated mAb or antigen-binding fragment comprises an amino acid sequence of SEQ ID NO: 56.

2. The isolated mAb or antigen-binding fragment according to claim 1, having a binding affinity to human CD3 with a Kd not greater than 70 nM.

3. The isolated mAb or antigen-binding fragment according to claim 1, wherein the isolated mAb or antigen-binding fragment is capable of high affinity binding to CD3, enhancing T cell activation, stimulating antibody response, or reversing the suppressive function of an immunosuppressive cell.

4. The isolated mAb or antigen-binding fragment according to claim 3, wherein the immunosuppressive cell comprises a T regulatory cell.

5. The isolated mAb or an antigen-binding fragment thereof according to claim 1, wherein the isolated mAb is a humanized antibody, a chimeric antibody, or a recombinant antibody.

6. The isolated mAb or an antigen-binding fragment thereof according to claim 1, wherein the isolated mAb comprises an IgG.

7. The isolated mAb or an antigen-binding fragment thereof according to claim 1, wherein the antigen-binding fragment comprises a Fv, a Fab, a F(ab')2, a scFV, a scFV2 fragment, or a combination thereof.

8. The isolated mAb or an antigen-binding fragment thereof according to claim 1, wherein the isolated mAb is a bispecific antibody, tri-specific antibody, or multi-specific antibody.

9. An IgG1 heavy chains for an isolated mAb having a binding specificity to human CD3, comprising an amino acid sequence SEQ ID NO: 55.

10. A kappa light chain for an isolated mAb having a binding specificity to human CD3, comprising an amino acid sequence of SEQ ID NO: 51.

11. A variable light chain for an isolated mAb having a binding specificity to human CD3, comprising an amino acid sequence of SEQ ID NO: 52.

12. A variable heavy chain for an isolated mAb having a binding specificity to human CD3, comprising an amino acid sequence of SEQ ID NO: 56.

13. An isolated nucleic acid encoding the isolated mAb or an antigen-binding fragment according to claim 1.

14. An expression vector comprising the isolated nucleic acid of claim 13.

15. A host cell comprising the nucleic acid of claim 13, wherein the host cell is a prokaryotic cell or a eukaryotic cell.

16. A method of producing an antibody comprising culturing the host cell of claim 15 so that the antibody is produced.

17. A pharmaceutical composition, comprising the isolated mAb or an antigen-binding fragment thereof according to claim 1 and a pharmaceutically acceptable carrier.

* * * * *